United States Patent
Hutchinson et al.

(10) Patent No.: US 9,193,710 B2
(45) Date of Patent: Nov. 24, 2015

(54) BENZODIAZEPINONES AS MODULATORS OF METABOTROPIC GLUTAMATE RECEPTOR FUNCTIONS AND NEUROLOGICAL USES THEREOF

(75) Inventors: John Howard Hutchinson, San Diego, CA (US); Leo Bleicher, San Diego, CA (US); Nick Cosford, La Jolla, CA (US); Robert John Ardecky, La Jolla, CA (US); Jiwen Zou, La Jolla, CA (US)

(73) Assignee: SANFORD-BURNHAM MEDICAL RESEARCH INSTITUTE, La Jolla, CA (US)

(*) Notice: Subject to any disclaimer, the term of this patent is extended or adjusted under 35 U.S.C. 154(b) by 0 days.

(21) Appl. No.: 14/342,339

(22) PCT Filed: Aug. 29, 2012

(86) PCT No.: PCT/US2012/052904
§ 371 (c)(1),
(2), (4) Date: Sep. 11, 2014

(87) PCT Pub. No.: WO2013/033246
PCT Pub. Date: Mar. 7, 2013

(65) Prior Publication Data
US 2015/0025064 A1   Jan. 22, 2015

Related U.S. Application Data

(60) Provisional application No. 61/528,639, filed on Aug. 29, 2011.

(51) Int. Cl.
| | |
|---|---|
| *C07D 403/04* | (2006.01) |
| *C07D 409/14* | (2006.01) |
| *C07D 243/14* | (2006.01) |
| *A61K 31/551* | (2006.01) |
| *A61K 45/06* | (2006.01) |
| *C07D 243/12* | (2006.01) |
| *C07D 417/04* | (2006.01) |

(52) U.S. Cl.
CPC ............ *C07D 403/04* (2013.01); *A61K 31/551* (2013.01); *A61K 45/06* (2013.01); *C07D 243/12* (2013.01); *C07D 243/14* (2013.01); *C07D 409/14* (2013.01); *C07D 417/04* (2013.01)

(58) Field of Classification Search
CPC ... C07D 403/04; C07D 409/14; C07D 243/14
USPC .............. 540/495, 517; 514/220, 221
See application file for complete search history.

(56) References Cited

U.S. PATENT DOCUMENTS 6,960,578 B2 * 11/2005 Adam et al. ............ 514/221

FOREIGN PATENT DOCUMENTS

| EP | 2137167 A1 | 12/2009 |
|---|---|---|
| WO | 01/29012 A2 | 4/2001 |
| WO | 02/083652 A1 | 10/2002 |
| WO | 03/066623 A1 | 8/2003 |
| WO | 2008/128889 A1 | 10/2008 |
| WO | 2013033246 A2 | 3/2013 |

OTHER PUBLICATIONS

Ried et al. (Chemische Berichte (1972), 105(1), 337-52). Abstract.*
Chmilenko et al. (Khimiya Geterotsiklicheskikh Soedinenii (1977), (4), 525-8). Abstract.*
Hamdi et al. (Journal of Heterocyclic Chemistry (1994), 31(2), 509-11). Abstract.*
Extended European Search Report dated Mar. 6, 2015 for related EP Patent Application No. 12827691.2 in 8 pages.

* cited by examiner

*Primary Examiner* — Bruck Kifle
(74) *Attorney, Agent, or Firm* — Procopio, Cory, Hargreaves & Savitch LLP

(57) ABSTRACT

The present invention relates to novel benzodiazepinone compounds of Formulae (I)

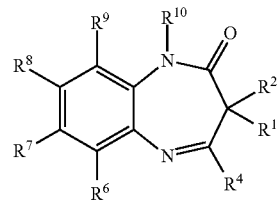

wherein $R^1$, $R^2$, $R^4$, $R^6$, $R^7$, $R^8$, $R^9$, and $R^{10}$ are as defined herein. The invention also relates to pharmaceutical compositions containing such compounds, methods of use of such compounds and compositions, and methods for preparing the compounds and compositions. The compounds are Group II metabotropic glutamate antagonists or allosteric modulators and are useful for the treatment of a variety of CNS disorders.

9 Claims, 1 Drawing Sheet

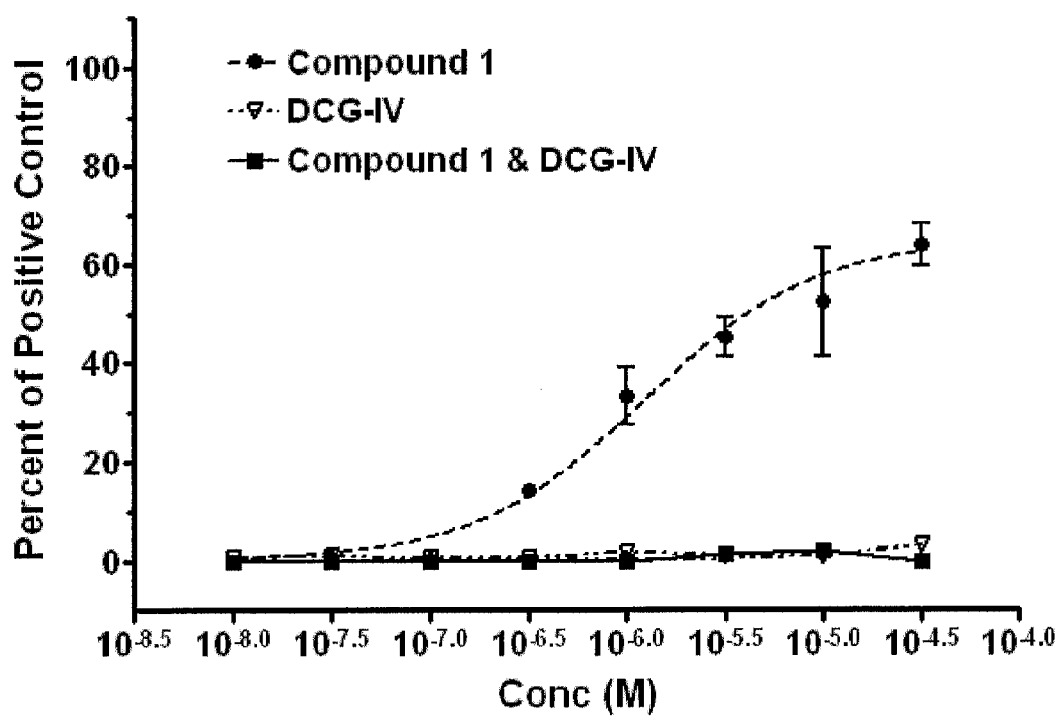

BENZODIAZEPINONES AS MODULATORS OF METABOTROPIC GLUTAMATE RECEPTOR FUNCTIONS AND NEUROLOGICAL USES THEREOF

CROSS-REFERENCE TO RELATED APPLICATIONS

This application is a national phase application of International Application No. PCT/US2012/052904, filed on Aug. 29, 2012, which claims priority under 35 U.S.C. 119(e) to U.S. Provisional Patent Application No. 61/528,639, filed on Aug. 29, 2011. The contents of each of the above patent applications are incorporated herein by reference in their entirety.

FIELD OF THE INVENTION

This invention relates to novel benzodiazepinone compounds, pharmaceutical compositions containing such compounds, and methods for preparing the compounds and compositions. These compounds are Group II metabotropic glutamate allosteric modulators and are useful for the treatment of a variety of central and peripheral nervous system disorders and cancers.

BACKGROUND OF THE INVENTION

The amino acid, glutamate is the major excitatory neurotransmitter in the central and peripheral nervous system and exerts its effects mainly through ionotropic glutamate receptors (iGluRs) and metabotropic glutamate receptors (mGluRs). The mGluRs are seven-transmembrane helix G protein-coupled receptors (GPCRs). The eight known members of the mGluR family are divided into three sub-groups (i.e., Groups I, II, and III) based on sequence homology, signal transduction and pharmacology. mGluR1 and mGluR5 belong to Group I, mGluR2 and mGluR3 belong to Group II, and mGluR4, mGluR6, mGluR7 and mGluR8 belong to Group III.

The orthosteric binding site of the mGluRs, which consists of a large bi-lobed extracellular amino terminal domain, is highly conserved, particularly within each group. For this reason it has been difficult to develop subtype-specific ligands (agonists and antagonists) for these receptors. Recently, advances have been made to develop highly selective compounds which modulate the activity of these receptors by binding within the receptors transmembrane heptahelical domain. These allosteric modulators are compounds that bind receptors at a non-active or non-orthosteric site and thereby can modulate receptor function even if the endogenous ligand is also bound to the receptor (orthosteric site). As a result, an allosteric modulator does not have to compete with the ligand to impact the receptor's function and permits a different approach to designing receptor modulators. As an example, the binding of an allosteric modulator may have a lower affinity to the site and still be effective unlike most conventional antagonists that must block ligand-receptor interactions. Moreover, the modulation of the allosteric site permits the natural processes of the endogenous ligand and associated receptor to continue. One type of allosteric modulator is a negative allosteric modulator (NAM) in which the modulator acts to decrease the signal sent by the endogenous ligand via the receptor. Another type of modulator is the positive allosteric modulator (PAM) which does not exhibit intrinsic agonism of the receptor but facilitates or potentiates agonist-mediated receptor activity. In some instances the modulator may be classified as an allosteric agonist in that it alone, without the effects of the natural ligand, induces receptor activity.

The GPCR contains two distinct domains; a large extracellular domain which binds glutamate at the orthosteric binding site and a heptahelical transmembrane domain, which has been found to bind a variety of ligands at one or more allosteric binding sites. Recent experimental findings show that GPCRs, form homodimers, heterodimers and in some cases hetero-oligomers with members of their own class as well as with other unrelated GPCRs and impacts their trafficking, signaling, and pharmacology (Milligan *Drug Discov Today* 2006, 11(11-12): 541-549). Although a GPCR monomer is sufficient to activiate a G protein, it is believed that dimerization leads to stabilization of the active conformation and enhancement of G protein activation. It has been clearly established that mGluRs exist as constitutive dimers with the two subunits being linked by a disulfide bridge (Romano et al. *J Biol Chem* 1996, 271(45):28612-28616). Recent studies have found that activation or inhibition of either monomer of the dimer complex facilitates a change in the activity or function of the adjoining monomer. As an example, it was found that $G_{i/o}$ protein regulation, which is necessary for the effects of hallucinogens, is enhanced by the formation of the $5HT_{2A}$/mGluR2 dimer complex and that activation of the mGluR2 monomer suppresses hallucinogen-specific signaling, while by contrast, the affinity of $mGluR_{2/3}$ agonists was reduced in the presence of an hallucinogen (Gonzalez-Maeso et al. *Nature* 2008, 452(7183):93-97).

The neuropsychological effects of hallucinogens present commonalities with the psychosis of schizophrenia, and both conditions are accompanied by disruptions of cortical sensory processing. Comparing the densities of $5HT_{2A}$ and mGluR2/3 binding sites in the cortex of schizophrenic subjects and controls, it was found that schizophrenic subjects had increased $5HT_{2A}$ and reduced mGluR2/3 receptor levels. It was found through mRNA assays that expression of mGluR2, but not mGluR3, was reduced in the cortex of schizophrenic subjects (Gonzalez-Maeso et al. *Nature* 2008, 452(7183):93-97).

Other various CNS disorders have been associated with the mGluR2 and/or mGluR3 receptors, and specific modulators of such receptors might be effective in the treatment of these acute and chronic diseases and conditions. Such acute and chronic diseases and conditions include Alzheimer's disease (Kim et al., *J. Neurosci.* 2010, 30:3870; Caraci et al., *Mol Pharmacol.* 2011, 79, 618), schizophrenia (Patil et al., *Nature Med* 2007, 13:1102), Parkinson's disease (Samadi et al., *J. Neuropathol. Exp. Neurol* 2009, 68:374), anxiety (Yoshimizu et al., *Psychopharmacology* 2006; 186:587-593), depression (Yoshimizu et al., *Psychopharmacology* 2006; 186:587-5930), obsessive-compulsive disorders, addiction (Beveridge et al., *Neurosci Letts* 2011, in press; Baptista et al *J. Neurosci* 2004, 33:4723; Dhanya et al., *J. Med. Chem,* 2011, 54:342; Tsunoka et al *Prog. Neuropsychopharmacol Biol Psychiatry* 2010, 34:639), epilepsy (Kinon et al., *J. Clin Psychopharmacol* 2011, 31:349), insomnia (Kinon et al., *J. Clin. Psychopharmacol.* 2011; 31 (3):349-355; Supplemental Table SDC3), peripheral pain (Carlton et al., *Brain Res* 2009, 1248: 86; Zhang et al., *Brain Res. Bulletin* 2009, 79:219-223), and cognitive and/or memory deficiencies due to diseases or aging, and the like (Nikiforuk et al., *JPET* 2010, 335:665). The efficacious treatment of such diseases may be through the activation or inhibition of the glutamate binding site or through a process regulating the activity of the mGluR2 and/or mGluR3 such as by an allosteric modulator. Antagonism of the mGluR2 and/or mGluR3 receptor may also prove beneficial as a therapy for treatment resistant depression, as orthosteric antagonists have been shown to activate the mTOR signaling pathway similar to the downstream effects of a subanesthetic dose of ketamine thus enabling synaptic plasticity (Karasawa et al., *Brain Res.* 2005, 1042(1): 92-98; Li et al., *Science* 2010, 329 (5994): 959-964; Koike et al., *Neuropharm.* 2011, 61(8):1419-1423; Dwyer et al., *Int. J. Neuropsychopharmacol.* 2012, 15(4):429-434). Other disorders and conditions associated with metabotropic glutamate receptors are cancers directly or indirectly linked to mGluR2/3, including but not limited to glioblastoma (D'Inofrio et al., *J. Neurochem* 2003, 84:1288-1295; Arcella et al., *Neuro-Oncology* 2005, 7:236-245), melanoma (Prickett et al., Nature Genetics 2011, 43:1119-1126), colon cancer, esophageal cancer (Chattopadhyay et al., *Oncology Reports* 2009, 21:1135-1146), pancreatic cancer and breast cancer.

The efficacious treatment of such diseases may be through the activation or inhibition of the glutamate binding site or through a process regulating the activity of the mGluR2 and/or mGluR3 such as by an allosteric modulator. Antagonism of the mGluR2 and/or mGluR3 receptor may also prove beneficial as a more rapid treatment for major depressive disorder and a therapy for treatment resistant depression, as orthosteric antagonists have been shown to activate the mTOR signaling pathway similar to the downstream effects of a subanesthetic dose of ketamine thus enabling synaptic plasticity (Karasawa et al., *Brain Res.* 2005, 1042(1): 92-98; Li et al., *Science* 2010, 329 (5994): 959-964; Koike et al., *Neuropharm.* 2011, 61(8): 1419-1423; Dwyer et al., *Int. J. Neuropsychopharmacol.* 2012, 15(4):429-434).

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

A need still exists for new drug therapies having greater receptor selectivity for the treatment of subjects suffering from or susceptible to the above diseases, disorders or conditions. In particular, a need still exists for new drugs having one or more improved properties either alone or when combined with other agents (such as safety profile, efficacy, or physical properties) relative to those therapies currently available.

SUMMARY OF THE INVENTION

In accordance with the purpose of the invention, as embodied and broadly described herein, the invention, in one aspect, relates to compounds useful as Group II metabotropic glutamate allosteric modulators (referred to herein as "mGluR2 agents" and/or "mGluR3 agents"). Additional aspects of the present invention include methods for making the invention mGluR2 and/or mGluR3 agents, pharmaceutical compositions containing these compounds, and methods of treating diseases, disorders and conditions associated with glutamate dysfunction using these compounds.

In accordance with the present invention, there are provided compounds having the structure of Formula (I), or a pharmaceutically acceptable salt, solvate, analog, prodrug, isomer or tautomer thereof: wherein:

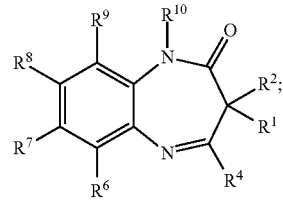

$R^1$ and $R^2$ are independently H, halogen, $C_1$-$C_8$ alkyl, —$NR^{11}R^{12}$, —$SR^{13}$, $C_3$-$C_6$ heteroalkyl, aryl or a monocyclic heteroaryl; or $R^1$ and $R^2$ together with the carbon to which they are attached form a $C_3$-$C_8$ cycloalkyl or heterocycloalkyl;

$R^4$ is $L^4$, $M^4$ or $T^4$; wherein $L^4$ is

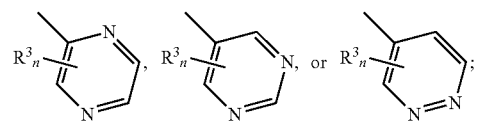

wherein, n is 1 or 2;

$M^4$ is a substituted or unsubstituted bicyclic heteroaryl or a substituted or unsubstituted bicyclic heterocycle, optionally substituted with 1 to 2 $R^3$ substituents;

$T^4$ is substituted or unsubstituted aryl or substituted or unsubstituted monocyclic heteroaryl containing 1 heteroatom selected from O or N optionally substituted with 1 to 2 $R^3$ substituents;

$R^3$ is H, halogen, —$OR^{11}$, —$NR^{11}R^{12}$, —$SR^{11}$, $S(O)R^{11}$, —$S(O)_2R^{12}$, —$S(O)_2NR^{11}R^{12}$, $C_1$-$C_8$ haloalkyl, $C_1$-$C_8$ alkyl, $C_1$-$C_8$ alkynyl, $C_1$-$C_8$ alkoxy, cyano, $C_1$-$C_8$ alkylamino, $C_1$-$C_8$ alkoxyamino, aryl, monocyclic heteroaryl or monocyclic heterocycle; and $R^6$ and $R^9$ each are independently selected from H, hydroxy, halogen, cyano, —$SR^{11}$, —$S(O)R^{11}$, —$S(O)_2R^{12}$, —$S(O)_2NR^{11}R^{12}$, $C_1$-$C_8$ haloalkyl, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)—$OR^{12}$, -alkylC(O)$NR^{11}R^{12}$, -alkenylC(O)$OR^{12}$, -alkenylC(O)$NR^{11}R^{12}$, -aryl(CH$_2$)$_m$C(O)$OR^{12}$, -aryl(CH$_2$)$_m$C(O)$NR^{11}R^{12}$, —$NR^{11}R^{12}$, —(CH$_2$)$_m$C(O)$NR^{11}S(O)_2R^{12}$, -aryl(CH$_2$)$_m$—C(O)$NR^{11}S(O)_2R^{12}$, —(CH$_2$)$_m$S(O)$_2NR^{11}C(O)$$R^{12}$, -aryl(CH$_2$)$_m$S(O)$_2NR^{11}C(O)R^{12}$, —XZ, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

$R^7$ is hydrogen;

if $R^4$ is $L^4$ or $M^4$, then $R^8$ is selected from H, hydroxy, halogen, $CF_3$, cyano, —$SR^{11}$, —$S(O)R^{11}$, —(CH$_2$)$_m$C(O)—$OR^{12}$, —(CH$_2$)$_m$C(O)$NR^{11}R^{12}$—$S(O)_2R^{12}$, $S(O)_2NR^{11}R^{12}$, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$C(O)(CH_2)_m$aryl, —$C(=NR^{11})NR^{11}R^{12}$, —$NR^{11}C(NR^{11})NR^{11}R^{12}$, —$C_1$-$C_8$ haloalkyl, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)$OR^{12}$, -alkylC(O)$NR^{11}R^{12}$, -alkenylC(O)$OR^{12}$, -alkenylC(O)$NR^{11}R^{12}$, -aryl(CH$_2$)$_m$C(O)$OR^{12}$, -aryl(CH$_2$)$_m$C(O)

NR$^{11}$R$^{12}$, —NR$^{11}$R$^{12}$, —(CH$_2$)$_m$C(O)NR$^{11}$S(O)$_2$R$^{12}$, -aryl (CH$_2$)$_m$C(O)NR$^{11}$S(O)$_2$R$^{12}$, —(CH$_2$)$_m$S(O)$_2$NR$^{11}$C(O)R$^{12}$, -aryl(CH$_2$)$_m$S(O)$_2$NR$^{11}$C(O)R$^{12}$, —XZ, or alkynyl-phenyl optionally substituted with halogen, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, CF$_3$, C$_1$-C$_8$ alkyl, C$_1$-C$_8$ alkoxy, cyano, amino, C$_1$-C$_8$ alkylamino, and C$_1$-C$_8$ alkoxyC$_1$-C$_8$ alkylamino; and when R$^4$ is T$^4$ then R$^8$ is selected from —C(O)OH, —C(O)NR$^{11}$R$^{12}$, —C(O)R$^{12}$, —NR$^{11}$C(O)R$^{12}$, —NR$^{11}$C(O)OR$^{12}$, -alkylC(O)OH, -alkenylC(O)OH, -aryl(CH$_2$)$_m$C(O)OH, -aryl(CH$_2$)$_m$C(O)OR$^{12}$, -alkylC(O)NR$^{11}$R$^{12}$, -aryl(CH$_2$)$_m$C(O)NR$^{11}$R$^{12}$, —B(OH)$_2$, tetrazole, carboxylic acid biostere, —NR$^{11}$R$^{12}$; —S(O)$_2$R$^{12}$, —S(O)$_2$NR$^{11}$R$^{12}$, —(CH$_2$)$_m$C(O)NR$^{11}$S(O)$_2$R$^{12}$, -aryl(CH$_2$)$_m$C(O)NR$^{11}$S(O)$_2$R$^{12}$, —(CH$_2$)$_m$S(O)$_2$NR$^{11}$C(O)R$^{12}$, and -aryl-(CH$_2$)$_m$S(O)$_2$NR$^{11}$C(O)R$^{12}$ or C$_3$-C$_6$ heterocycle or monocyclic heteroaryl, optionally substituted with halogen;

X is C$_1$-C$_8$ alkylene, C$_2$-C$_8$ alkenylene, C$_2$-C$_8$ alkynylene, —C(O) or —S(O)$_2$;

Z is H, CF$_3$, —C$_1$-C$_8$ alkyl, C$_3$-C$_8$ cycloalkyl, C$_1$-C$_8$ alkoxy, amino, C$_1$-C$_8$ alkylthio, aryl, or C$_3$-C$_6$ heterocycle or monocyclic heteroaryl, optionally substituted with halogen;

m is 0, 1, 2, 3, or 4;

R$^{10}$ is H, CF$_3$, C$_1$-C$_8$ alkyl, C$_3$-C$_8$ cycloalkyl, C$_2$-C$_8$ alkenyl, C$_2$-C$_8$ alkynyl, aryl, C$_5$-C$_{10}$ heterocycle each of which is optionally substituted with halogen, —OR$^{11}$, —NR$^{11}$R$^{12}$, —SR$^{11}$, —S(O)R$^{11}$, —S(O)$_2$R$^{12}$, or —S(O)$_2$NR$^{11}$R$^{12}$;

R$^{11}$, R$^{12}$, and a K are independently H, C$_1$-C$_8$ alkyl, C$_1$-C$_8$ fluoroalkyl, aryl, benzyl, C$_{2-8}$ alkenyl, C$_{2-8}$ alkynyl, -alkyl-C(O)OR$^{14}$, -alkenyl-C(O)OR$^{14}$C(O)R$^{14}$, monocylic heteroaryl, or monocylic heterocycle; and R$^{14}$ is H, C$_1$-C$_8$ alkyl, C$_1$-C$_8$ haloalkyl, aryl, or benzyl.

In some embodiments, the compound of Formula (I) has the structure of Formula (II)

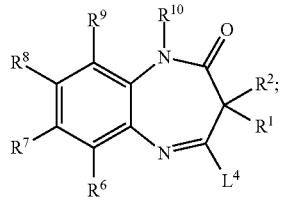

wherein,

R$^1$ and R$^2$ are independently H, halogen, C$_1$-C$_8$ alkyl, —NR$^{11}$R$^{12}$, C$_3$-C$_6$ heteroalkyl, aryl or a monocyclic heteroaryl; or R$^1$ and R$^2$ together with the carbon to which they are attached form a C$_3$-C$_8$ cycloalkyl or heterocycloalkyl;

L$^4$ is

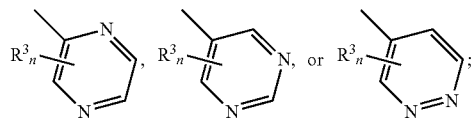

wherein, n is 1 or 2;

R$^3$ is H, halogen, —OR$^{11}$, —NR$^{11}$R$^{12}$, —S(O)R$^{11}$, —S(O)$_2$NR$^{11}$R$^{12}$, —S(O)$_2$NR$^{11}$R$^{12}$, C$_1$-C$_8$ haloalkyl, C$_1$-C$_8$ alkyl, C$_1$-C$_8$ alkoxy, cyano, C$_1$-C$_8$ alkylamino, C$_1$-C$_8$ alkoxyamino, aryl, monocyclic heteroaryl or monocyclic heterocycle; and R$^6$ and R$^9$ each are independently selected from H, hydroxy, halogen, cyano, —SR$^{11}$, —S(O)R$^{11}$, —S(O)$_2$R$^{12}$, —S(O)$_2$NR$^{11}$R$^{12}$, C$_1$-C$_8$ haloalkyl, —C(O)OR$^{12}$, —C(O)NR$^{11}$R$^{12}$, —C(O)R$^{12}$, —NR$^{11}$C(O)R$^{12}$, —NR$^{11}$S(O)$_2$R$^{12}$, —NR$^{11}$C(O)OR$^{12}$, —B(OH)$_2$, tetrazole, carboxylic acid biostere, C$_1$-C$_8$ alkyl, C$_3$-C$_8$ cycloalkyl, C$_2$-C$_8$ alkenyl, C$_1$-C$_8$ alkoxy, substituted or unsubstituted aryl, -alkylC(O)—OR$^{12}$, -alkylC(O)NR$^{11}$R$^{12}$, -alkenylC(O)OR$^{12}$, -alkenylC(O)NR$^{11}$R$^{12}$, -aryl(CH$_2$)$_m$C(O)OR$^{12}$, -aryl(CH$_2$)$_m$C(O)NR$^{11}$R$^{12}$, —NR$^{11}$R$^{12}$, —(CH$_2$)$_m$C(O)NR$^{11}$S(O)$_2$R$^{12}$, -aryl(CH$_2$)$_m$—C(O)NR$^{11}$S(O)$_2$R$^{12}$, —(CH$_2$)$_m$S(O)$_2$NR$^{11}$C(O)R$^{12}$, -aryl(CH$_2$)$_m$S(O)$_2$NR$^{11}$C(O)R$^{12}$, —XZ, or substituted or unsubstituted monocyclic heterocycle or unsubstituted monocyclic heteroaryl containing 1 to 4 heteroatoms, optionally substituted with 1 to 2 substituents selected from the group consisting of H, hydroxyl, halogen, CF$_3$, C$_1$-C$_8$ alkyl, C$_1$-C$_8$ alkoxy, cyano, amino, C$_1$-C$_8$ alkylamino, and C$_1$-C$_8$ alkoxyC$_1$-C$_8$ alkylamino;

R$^7$ is hydrogen;

R$^8$ is selected from H, hydroxy, halogen, CF$_3$, cyano, —SR$^{11}$, —S(O)R$^{11}$, —(CH$_2$)$_m$C(O)—OR$^{12}$, —(CH$_2$)$_m$C(O)NR$^{11}$R$^{12}$, —S(O)$_2$R$^{12}$, —S(O)$_2$NR$^{11}$R$^{12}$, —C(O)OR$^{12}$, —C(O)NR$^{11}$R$^{12}$, —C(O)R$^{12}$, —NR$^{11}$C(O)R$^{12}$, —NR$^{11}$S(O)$_2$R$^{12}$, —NR$^{11}$C(O)OR$^{12}$, —C(O)(CH$_2$)$_m$aryl, —C(=NR$^{11}$)NR$^{11}$R$^{12}$, —NR$^{11}$C(=NR$^{11}$)NR$^{11}$R$^{12}$, —C$_1$-C$_8$ haloalkyl, —B(OH)$_2$, tetrazole, carboxylic acid biostere, C$_1$-C$_8$ alkyl, C$_3$-C$_8$ cycloalkyl, C$_2$-C$_8$ alkenyl, C$_1$-C$_8$ alkoxy, substituted or unsubstituted aryl, -alkylC(O)OR$^{12}$, -alkylC(O)NR$^{11}$R$^{12}$, -alkenylC(O)OR$^{12}$, -alkenylC(O)NR$^{11}$R$^{12}$, -aryl(CH$_2$)$_m$C(O)OR$^{12}$, -aryl(CH$_2$)$_m$C(O)NR$^{11}$R$^{12}$, —NR$^{11}$R$^{12}$, —(CH$_2$)$_m$C(O)NR$^{11}$S(O)$_2$R$^{12}$, -aryl(CH$_2$)$_m$C(O)NR$^{11}$S(O)$_2$R$^{12}$, —(CH$_2$)$_m$S(O)$_2$NR$^{11}$C(O)R$^{12}$, -aryl(CH$_2$)$_m$S(O)$_2$NR$^{11}$C(O)R$^{12}$, —XZ, or alkynyl-phenyl optionally substituted with halogen, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, CF$_3$, C$_1$-C$_8$ alkyl, C$_1$-C$_8$ alkoxy, cyano, amino, C$_1$-C$_8$ alkylamino, and C$_1$-C$_8$ alkoxyC$_1$-C$_8$ alkylamino;

X is C$_1$-C$_8$ alkylene, C$_2$-C$_8$ alkenylene, C$_2$-C$_8$ alkynylene, —C(O) or —S(O)$_2$;

Z is H, CF$_3$, —C$_1$-C$_8$ alkyl, C$_3$-C$_8$ cycloalkyl, C$_1$-C$_8$ alkoxy, amino, C$_1$-C$_8$ alkylthio, aryl, C$_3$-C$_6$ heterocycle or monocyclic heteroaryl, optionally substituted with halogen;

m is 0, 1, 2, 3, or 4;

R$^{10}$ is H, CF$_3$, C$_1$-C$_8$ alkyl, —C$_3$-C$_8$ cycloalkyl, C$_2$-C$_8$ alkenyl, C$_2$-C$_8$ alkynyl, C$_5$-C$_{10}$ aryl, C$_5$-C$_{10}$ heterocycle each of which is optionally substituted with halogen, —OR$^{11}$, —NR$^{11}$R$^{12}$, —SR$^{11}$, —S(O)R$^{11}$, S(O)$_2$R$^{12}$, or —S(O)$_2$NR$^{11}$R$^{12}$;

R$^{11}$, R$^{12}$, and R$^{13}$ are independently H, C$_1$-C$_8$ alkyl, C$_1$-C$_8$ fluoroalkyl, aryl, benzyl, C$_{2-8}$ alkenyl, C$_{2-8}$ alkynyl, -alkyl-C(O)OR$^{14}$, -alkenyl-C(O)OR$^{14}$—C(O)R$^{14}$, monocylic heteroaryl, or monocylic heterocycle; and R$^{14}$ is H, C$_1$-C$_8$ alkyl, C$_1$-C$_8$ fluoroalkyl, aryl, or benzyl.

In various embodiments when the compound is of Formula (II), R$^3$ is H, OR$^{11}$, —C$_1$-C$_8$ alkylfluoro, —C$_1$-C$_8$ alkyl, or C$_1$-C$_8$ alkoxy.

In other embodiments when the compound is of Formula (II), $R^1$, $R^2$ and $R^{10}$ are H; $L^4$ is

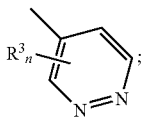

$R^8$ is halogen, $CF_3$, cyano, thiophene, imidazole, tetrazole, —$(CH_2)_mC(O)OR^{12}$, —$(CH_2)_mC(O)NR^{11}R^{12}$, -aryl$(CH_2)_m$C(O)OR^{12}$, -aryl$(CH_2)_mC(O)NR^{11}R^{12}$, —$NR^{11}R^{12}$, phenyl optionally substituted with halogen or alkynyl-phenyl optionally substituted with halogen; wherein m is 0, 1, 2, or 3; and $R^{12}$ is H or $C_1$-$C_6$ alkyl.

In yet other embodiments when the compound is of Formula (II), $R^1$, $R^2$ and $R^{10}$ are H; $L^4$ is

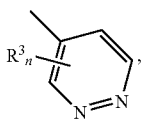

wherein, $R^3$ is hydrogen; $R^8$ is halogen, $CF_3$, cyano, thiophene, imidazole, tetrazole, —$(CH_2)_mC(O)OR^{12}$, —$(CH_2)_mC(O)NR^{11}R^{12}$, -aryl$(CH_2)_mC(O)OR^{12}$, -aryl$(CH_2)_mC(O)NR^{11}R^{12}$, —$NR^{11}R^{12}$, phenyl optionally substituted with halogen or alkynyl-phenyl optionally substituted with halogen; wherein m is 0, 1, 2, or 3; $R^{12}$ is H or $C_1$-$C_6$ alkyl; and $R^6$ and $R^9$ are hydrogen.

In still other embodiments when the compound is of Formula (II), $R^1$, $R^2$ and $R^{10}$ are H; $L^4$ is

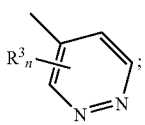

wherein, $R^3$ is hydrogen; $R^8$ is halogen, $CF_3$, cyano, thiophene, imidazole, tetrazole, —$(CH_2)_mC(O)$—$OR^{12}$, —$(CH_2)_mC(O)NR^{11}R^{12}$, aryl$(CH_2)_mC(O)OR^{12}$, aryl$(CH_2)_m$C(O)NR^{11}R^{12}$, —$NR^{11}R^{12}$, phenyl optionally substituted with halogen or alkynyl-phenyl optionally substituted with halogen; wherein m is 0, 1, 2, or 3; and $R^{12}$ is H or $C_1$-$C_6$ alkyl.

In some embodiments, the compound of Formula (I) has the structure of Formula (III):

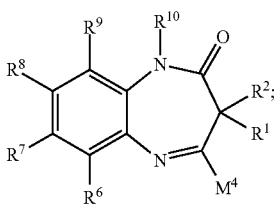

wherein $R^1$ and $R^2$ are independently H, halogen, $C_1$-$C_8$ alkyl, —$NR^{11}R^{12}$, —$SR^{13}$, $C_3$-$C_6$ heteroalkyl, aryl or a monocyclic heteroaryl; or $R^1$ and $R^2$ together with the carbon to which they are attached form a $C_3$-$C_8$ cycloalkyl or heterocycloalkyl;

$M^4$ is a substituted or unsubstituted bicyclic heteroaryl or a substituted or unsubstituted bicyclic heterocycle, optionally substituted with 1 to 2 $R^3$ substituents;

$R^3$ is H, halogen, —$OR^{11}$, —$NR^{11}R^{12}$, —$SR^{11}$, —$S(O)_2R^{12}$, $S(O)_2NR^{11}R^{12}$, $C_1$-$C_8$ haloalkyl, $C_1$-$C_8$ alkyl, $C_1$-$C_8$ alkoxy, cyano, $C_1$-$C_8$ alkylamino, $C_1$-$C_8$ alkoxyamino, aryl, monocyclic heteroaryl or monocyclic heterocycle; and $R^6$ and $R^9$ each are independently selected from H, hydroxy, halogen, cyano, —$SR^{11}$, —$S(O)R^{11}$, —$S(O)_2R^{12}$, —$S(O)_2NR^{11}R^{12}$, $C_1$-$C_8$ haloalkyl, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)—$OR^{12}$, -alkylC(O)NR^{11}R^{12}$, alkenylC(O)OR^{12}$, -alkenylC(O)NR^{11}R^{12}$, aryl$(CH_2)_mC(O)OR^{12}$, -aryl$(CH_2)_mC(O)NR^{11}R^{12}$, $NR^{11}R^{12}$, —$(CH_2)_mC(O)NR^{11}S(O)_2R^{12}$, -aryl$(CH_2)_m$—C(O)NR^{11}S(O)_2R^{12}$, —$(CH_2)_mS(O)_2NR^{11}C(O)R^{12}$, -aryl$(CH_2)_mS(O)_2NR^{11}C(O)R^{12}$, —XZ, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

$R^7$ is hydrogen;

$R^8$ is selected from H, hydroxy, halogen, $CF_3$, cyano, —$SR^{11}$, —$S(O)R^{11}$, —$(CH_2)_mC(O)$—$OR^{12}$, —$(CH_2)_mC(O)NR^{11}R^{12}$—$S(O)_2R^{12}$, —$S(O)_2NR^{11}R^{12}$, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$C(O)(CH_2)_m$aryl, —$C(=NR^{11})NR^{11}R^{12}$, —$NR^{11}C(=NR^{11})NR^{11}R^{12}$, —$C_1$-$C_8$ haloalkyl, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)OR^{12}$, -alkylC(O)NR^{11}R^{12}$, -alkenylC(O)OR^{12}$, -alkenylC(O)NR^{11}R^{12}$, -aryl$(CH_2)_mC(O)OR^{12}$, -aryl$(CH_2)_mC(O)NR^{11}R^{12}$, —$NR^{11}R^{12}$, —$(CH_2)_mC(O)NR^{11}S(O)_2R^{12}$, -aryl$(CH_2)_mC(O)NR^{11}S(O)_2R^{12}$, —$(CH_2)_mS(O)_2NR^{11}C(O)R^{12}$, -aryl$(CH_2)_mS(O)_2NR^{11}C(O)R^{12}$, —XZ, or alkynyl-phenyl optionally substituted with halogen, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

X is $C_1$-$C_8$ alkylene, $C_2$-$C_8$ alkenylene, $C_2$-$C_8$ alkynylene, —C(O) or —$S(O)_2$;

Z is H, $CF_3$, —$C_1$-$C_8$ alkyl, $C_3$-$C_8$ cycloalkyl, $C_1$-$C_8$ alkoxy, amino, $C_1$-$C_8$ alkylthio, aryl, $C_3$-$C_6$ heterocycle or monocyclic heteroaryl, optionally substituted with halogen;

m is 0, 1, 2, 3, or 4;

$R^{10}$ is H, $CF_3$, $C_1$-$C_8$ alkyl, —$C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{11}$, —$NR^{11}R^{12}$, —$SR^{11}$, —$S(O)R^{11}$, —$S(O)_2R^{12}$, or —$S(O)_2NR^{11}R^{12}$;

$R^{11}$, $R^{12}$, and $R^{13}$ are independently H, $C_1$-$C_8$ alkyl, $C_1$-$C_8$ fluoroalkyl, aryl, benzyl, $C_{2-8}$ alkenyl, $C_{2-8}$ alkynyl, -alkylC(O)OR^{14}$, -alkenylC(O)OR^{14}$—$C(O)R^{14}$, monocylic heteroaryl, or monocylic heterocycle; and $R^{14}$ is H, $C_1$-$C_8$ alkyl, $C_1$-$C_8$ fluoroalkyl, aryl, or benzyl.

In some embodiments when the compound is of Formula (III), $R^1$, $R^2$ and $R^{10}$ are hydrogen; $R^3$ is hydrogen; $R^8$ is halogen, $CF_3$, cyano, thiophene, imidazole, tetrazole, —$(CH_2)_mC(O)$—$OR^{12}$, —$(CH_2)_mC(O)NR^{11}R^{12}$, -aryl- $(CH_2)_mC(O)OR^{12}$, -aryl$(CH_2)_mC(O)NR^{11}R^{12}$, —$NR^{11}R^{12}$, or phenyl optionally substituted with halogen; wherein m is 0, 1, 2, or 3; $R^{12}$ is H or $C_1$-$C_6$ alkyl.

In other embodiments when the compound is of Formula (III), $R^1$, $R^2$ and $R^{10}$ are hydrogen; $M^4$ is

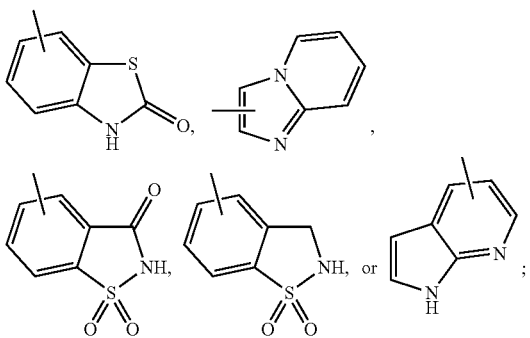

$R^8$ is halogen, $CF_3$, cyano, thiophene, imidazole, tetrazole, —$(CH_2)_mC(O)OR^{12}$, —$(CH_2)_mC(O)NR^{11}R^{12}$, -aryl$(CH_2)_m C(O)OR^{12}$, -aryl$(CH_2)_mC(O)NR^{11}R^{12}$, —$NR^{11}R^{12}$, phenyl optionally substituted with halogen or alkynyl-phenyl optionally substituted with halogen; wherein m is 0, 1, 2, or 3; $R^{12}$ is H or $C_1$-$C_6$ alkyl; and $R^6$ and $R^9$ are hydrogen.

In still other embodiments when the compound is of Formula (III), $R^1$, $R^2$ and $R^{10}$ are hydrogen; $M^4$ is

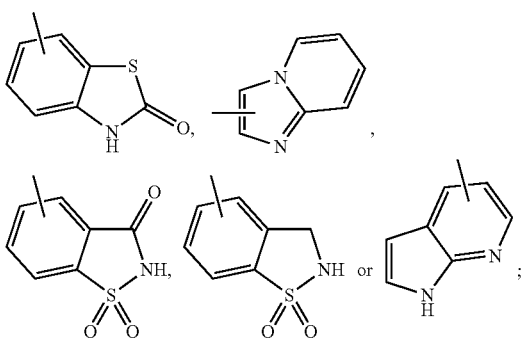

$R^6$ and $R^9$ are hydrogen; $R^8$ is halogen, $CF_3$, cyano, thiophene, imidazole, tetrazole, —$(CH_2)_mC(O)OR^{12}$, —$(CH_2)_mC(O)NR^{11}R^{12}$, aryl$(CH_2)_mC(O)OR^{12}$, aryl$(CH_2)_m C(O)NR^{11}R^{12}$, —$NR^{11}R^{12}$, phenyl optionally substituted with halogen or alkynyl-phenyl optionally substituted with halogen; wherein m is 0, 1, 2, or 3; and $R^{12}$ is H or $C_1$-$C_6$ alkyl.

In some embodiments, the compound of Formula (I) has the structure of Formula (IV):

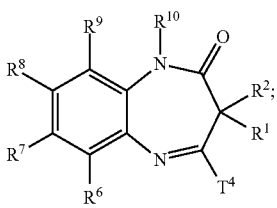

wherein $R^1$ and $R^2$ are independently H, halogen, $C_1$-$C_8$ alkyl, —$NR^{11}R^{12}$, —$SR^{13}$, $C_3$-$C_6$ heteroalkyl, aryl or a monocyclic heteroaryl; or $R^1$ and $R^2$ together with the carbon to which they are attached form a $C_3$-$C_8$ cycloalkyl or heterocycloalkyl;

$T^4$ is substituted or unsubstituted aryl or substituted or unsubstituted monocyclic heteroaryl containing 1 heteroatom selected from O or N optionally substituted with 1 to 2 $R^3$ substituents;

$R^3$ is H, halogen, —$OR^{11}$, —$NR^{11}R^{12}$, —$SR^{11}$, —$S(O)R^{11}$, —$S(O)_2R^{12}$, $C_1$-$C_8$ haloalkyl, $C_1$-$C_8$ alkyl, $C_1$-$C_8$ alkynyl, $C_1$-$C_8$ alkoxy, cyano, $C_1$-$C_8$ alkylamino, $C_1$-$C_8$ alkoxyamino, aryl, monocyclic heteroaryl or monocyclic heterocycle; and $R^6$ and $R^9$ each are independently selected from H, hydroxy, halogen, cyano, —$SR^{11}$, —$S(O)R^{11}$, —$S(O)_2R^{12}$, —$S(O)_2NR^{11}R^{12}$, $C_1$-$C_8$ haloalkyl, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)—$OR^{12}$, -alkylC(O)$NR^{11}R^{12}$, -alkenylC(O)$OR^{12}$, -alkenylC(O) $NR^{11}R^{12}$, -aryl$(CH_2)_mC(O)OR^{12}$, -aryl$(CH_2)_mC(O)$ $NR^{11}R^{12}$, —$NR^{11}R^{12}$, —$(CH_2)_mC(O)NR^{11}S(O)_2R^{12}$, -aryl $(CH_2)_m$—$C(O)NR^{11}S(O)_2R^{12}$, —$(CH_2)_mS(O)_2NR^{11}C(O)$ $R^{12}$, -aryl$(CH_2)_mS(O)_2NR^{11}C(O)R^{12}$, —XZ, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

$R^7$ is hydrogen;

$R^8$ is selected from —$C(O)OH$, —$C(O)NR^{11}R^{12}$, —$C(O)$ $R^{12}$, —$NR^{11}$—$C(O)R^{12}$, —$NR^{11}$—$C(O)R^{12}$, —$NR^{11}C(O)$ $OR^{12}$, -alkylC(O)OH, -alkenylC(O)OH, -aryl$(CH_2)_mC(O)$ OH, -alkylC(O)$NR^{11}R^{12}$, -aryl$(CH_2)_mC(O)NR^{11}R^{12}$, —$B(OH)_2$, tetrazole, carboxylic acid biostere, —$NR^{11}R^{12}$, —$S(O)_2R^{12}$, —$S(O)_2NR^{11}R^{12}$, —$(CH_2)_mC(O)NR^{11}S(O)_2$ $R^{12}$, -aryl$(CH_2)_mC(O)NR^{11}S(O)_2R^{12}$, —$(CH_2)_mS(O)_2$— $NR^{11}C(O)R^{12}$ and -aryl$(CH_2)_mS(O)_2NR^{11}C(O)R^{12}$;

X is $C_1$-$C_8$ alkylene, $C_2$-$C_8$ alkenylene, $C_2$-$C_8$ alkynylene, —$C(O)$ or —$S(O)_2$;

Z is H, $CF_3$, —$C_1$-$C_8$ alkyl, $C_3$-$C_8$ cycloalkyl, $C_1$-$C_8$ alkoxy, amino, $C_1$-$C_8$ alkylthio, aryl, $C_3$-$C_6$ heterocycle or monocyclic heteroaryl, optionally substituted with halogen;

m is 0, 1, 2, 3, or 4;

$R^{10}$ is H, $CF_3$, $C_1$-$C_8$ alkyl, $C_3$-$C_8$ cycloalkyl, $C_2$-$C_8$ alkenyl, $C_2$-$C_8$ alkynyl, aryl, $C_5$-$C_{10}$ heterocycle each of which is optionally substituted with halogen, $OR^{11}$, —$NR^{11}R^{12}$, $SR^{11}$, —$S(O)R^{11}$, —$S(O)_2R^{12}$ or —$S(O)_2NR^{11}R^{12}$;

$R^{11}$, $R^{12}$, and $R^{13}$ are independently H, $C_1$-$C_8$ alkyl, $C_1$-$C_8$ fluoroalkyl, aryl, benzyl, $C_{2-8}$ alkenyl, $C_{2-8}$ alkynyl, -alkylC (O)$OR^{14}$, -alkenylC(O)$OR^{14}$C(O)$R^{14}$, monocylic heteroaryl, or monocylic heterocycle; and $R^{14}$ is H, $C_1$-$C_8$ alkyl, $C_1$-$C_8$ fluoroalkyl, aryl, or benzyl.

In various embodiments when the compound is of Formula (IV), $R^1$, $R^2$ and $R^{10}$ are hydrogen; $T^4$ is

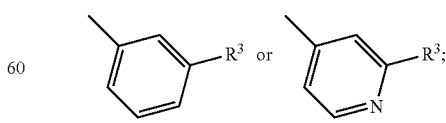

$R^3$ is H, halogen, $OR^{11}$, $C_1$-$C_8$ alkylfluoro, $C_1$-$C_8$ alkyl, $C_1$-$C_8$ alkynyl, $C_1$-$C_8$ alkoxy, cyano, aryl, monocyclic heteroaryl or monocyclic heterocycle; and m is 0, 1, 2, or 3; and $R^{12}$ is H or $C_1$-$C_6$ alkyl.

In other embodiments when the compound is of Formula (IV), $R^1$, $R^2$ and $R^{10}$ are hydrogen; $T^4$ is

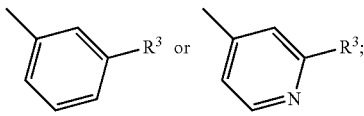

$R^3$ is H, Cl, cyano, aryl, or monocyclic heteroaryl; and $R^8$ is -alkylC(O)OH, -alkenylC(O)OH, -aryl$(CH_2)_mC$(O)OH, -alkylC(O)$NR^{11}R^{12}$, -aryl$(CH_2)_mC$(O)$NR^{11}R^{12}$, $B(OH)_2$, tetrazole, or —S$(O)_2R^{12}$; wherein m is 0, 1, 2, or 3; $R^6$ and $R^9$ are hydrogen; and $R^{12}$ is H or $C_1$-$C_6$ alkyl.

Also provided herein are pharmaceutical compositions comprising a therapeutically effective amount of a compound of Formula (I), Formula (II), Formula (III) or Formula (IV), or a pharmaceutically acceptable salt, solvate, analog, prodrug, isomer or tautomer thereof, and at least one pharmaceutically acceptable inactive ingredient selected from pharmaceutically acceptable diluents, pharmaceutically acceptable excipients, and pharmaceutically acceptable carriers. In some embodiments the pharmaceutical composition further comprises one or more additional therapeutically active agents selected from but not limited to an SSRI, an SNRI, a NDRI, a triple uptake inhibitor, an NMDA antagonist, a cholinesterase inhibitor, a monoamine oxidase inhibitor, lithium or an anticonvulsant. The additional therapeutically active agent may be used to enhance the activity of the compound of Formula (I), Formula (II), Formula (III) or Formula (IV).

Also provided herein is a method for treating one or more mGluR 2/3-dependent or mGluR 2/3-mediated disease or condition in a subject by administering to the subject a therapeutically effective amount of a compound of Formula (I), Formula (II), Formula (III) or Formula (IV). In some embodiments the mGluR 2/3-dependent or mGluR 2/3-mediated disease or condition is a central or peripheral nervous system disorder or disease. These central and peripheral nervous system disorders or diseases include but are not limited to Alzheimer's disease, schizophrenia, Parkinson's disease, anxiety, depression, treatment resistant depression, obsessive-compulsive disorders, psychosis, addiction, epilepsy, insomnia, brain or central nervous system trauma and/or recovery therefrom, ischemia of the central and/or peripheral nervous systems, pain, learning and memory disorders and cognitive and memory deficiencies due to disease or aging and cancer. In other embodiments, the disclosed compounds and methods are useful for improving cognitive outcomes and mood disorders.

In another embodiment, there are provided methods of treating a nervous system disorder related to cellular degeneration, a psychiatric condition, cognitive impairment, cellular trauma or injury, or another neurologically related condition in a subject or patient. The method includes administering a compound of Formula (I), Formula (II), Formula (III) or Formula (IV), which may be neurogenic, optionally in combination with one or more neurogenic or neurogenic sensitizing agents to a subject or patient in need thereof, wherein the compound or composition is effective to treat the nervous system disorder in the subject or patient. In some embodiments, the nervous system disorder related to cellular degeneration is a neurodegenerative disorder, a neural stem cell disorder, a neural progenitor cell disorder, an ischemic disorder, a toxicity disorder or a combination thereof. In other embodiments, the nervous system disorder is a neurodegenerative disorder selected from a degenerative disease of the retina, lissencephaly syndrome, cerebral palsy, or a combination thereof. In other embodiments, the nervous system disorder is a psychiatric condition selected from a neuropsychiatric disorder, an affective disorder, or a combination thereof. In some embodiments, the neuropsychiatric disorder is schizophrenia. In other embodiments, the affective disorder is selected from a mood disorder, an anxiety disorder or a combination thereof. In one aspect, the mood disorder is a depressive disorder. In certain embodiments, the depressive disorder is depression, major depressive disorder, treatment-resistant depression, depression due to drug and/or alcohol abuse, post-pain depression, post-partum depression, seasonal mood disorder, and combinations thereof. In a further embodiment, the nervous system disorder is an anxiety disorder selected from general anxiety disorder, post-traumatic stress-disorder (PTSD), obsessive-compulsive disorder, panic attacks, and combinations thereof. In still other embodiments, the nervous system disorder is a cognitive impairment due to a memory disorder, memory loss separate from dementia, mild cognitive impairment (MCI), age related cognitive decline, age-associated memory impairment, cognitive decline resulting from use of general anesthetics, chemotherapy, radiation treatment, post-surgical trauma, therapeutic intervention, cognitive decline associated with Alzheimer's disease or epilepsy, dementia, delirium, or a combination thereof. In yet opther embodiments, the nervous system disorder is a cellular trauma or injury selected from neurological trauma or injury, brain or spinal cord trauma or injury related to surgery, retinal injury or trauma, injury related to epilepsy, brain or spinal cord related injury or trauma, brain or spinal cord injury related to cancer treatment, brain or spinal cord injury related to infection, brain or spinal cord injury related to inflammation, brain or spinal cord injury related to environmental toxin, and combinations thereof. In yet another embodiment, the nervous system disorder is a neurologically-related condition selected from a learning disorder, autism, attention deficit disorder, narcolepsy, sleep disorder, epilepsy, temporal lobe epilepsy, or a combination thereof.

Other disorders and conditions associated with metabotropic glutamate receptors are cancers directly or indirectly linked to mGluR2/3, including but not limited to glioblastoma (D'Inofrio et al., *J. Neurochem* 2003, 84:1288-1295; Arcella et al., *Neuro-Oncology* 2005, 7:236-245), melanoma (Prickett et al., *Nature Genetics* 2011, 43:1119-1126), colon cancer, esophageal cancer (Chattopadhyay et al., *Oncology Reports* 2009; 21:1135-1146), pancreatic cancer and breast cancer.

The details of additional embodiments are set forth in the accompanying drawings and the description below. Other features, objects, and advantages of the embodiments will be apparent from the drawings and detailed description, and from the claims.

BRIEF DESCRIPTION OF THE DRAWINGS

FIG. 1 is a dose-response curve showing the effect of Compound 1 (8-bromo-4-(pyridazin-4-yl)-1H-benzo[b][1,4]diazepin-2(3H)-one) and DCG-IV, an mGluR2/3 agonist, alone and in combination on neuronal differentiation of cultured human neural stem cells (hNSCs). When run independently, each compound was tested in a concentration response curve ranging from 0.01 μM to 31.6 μM. Data are presented as the percentage of the neuronal positive control, with basal media values subtracted. The calculated $EC_{50}$ for the Compound 1 dose-response curve was 2.53 μM while the $EC_{50}$ for the positive control was calculated to be 1.8 μM. DCG-IV showed no effect on hNSCs. In combination, the compounds were combined at equal concentrations at each point (for example, the first point in the combined curve consisted of a test of 0.01 μM Compound 1 and 0.01 μM DCG-IV). When used in combination, there was no noted neurogenesis, with the combination curve overlapping the DCG-IV curve.

DETAILED DESCRIPTION OF THE INVENTION

Compositions

A compound of Formula (I), or a pharmaceutically acceptable salt, solvate, analog, prodrug, isomer or tautomer thereof:

wherein,
$R^1$ and $R^2$ are independently H, halogen, $C_1$-$C_8$ alkyl, —$NR^{11}R^{12}$, —$SR^{13}$, $C_3$-$C_6$ heteroalkyl, aryl or a monocyclic heteroaryl; or
$R^1$ and $R^2$ together with the carbon to which they are attached form a $C_3$-$C_8$ cycloalkyl or heterocycloalkyl;
$R^4$ is $L^4$, $M^4$ or $T^4$; wherein
$L^4$ is wherein, n is 1 or 2;
$M^4$ is a substituted or unsubstituted bicyclic heteroaryl or a substituted or unsubstituted bicyclic heterocycle, optionally substituted with 1 to 2 $R^3$ substituents;
$T^4$ is substituted or unsubstituted aryl or substituted or unsubstituted monocyclic heteroaryl containing 1 heteroatom selected from 0 or N optionally substituted with 1 to 2 $R^3$ substituents;
$R^3$ is H, halogen, —$OR^{11}$, —$NR^{11}R^{12}$, —$SR^{11}$, —S(O)$R^{11}$, —$S(O)_2R^{12}$, —$S(O)_2NR^{11}R^{12}$, $C_1$-$C_8$ haloalkyl, $C_1$-$C_8$ alkyl, $C_1$-$C_8$ alkynyl, $C_1$-$C_8$ alkoxy, cyano, $C_1$-$C_8$ alkylamino, $C_1$-$C_8$ alkoxyamino, aryl, monocyclic heteroaryl or monocyclic heterocycle; and
$R^6$ and $R^9$ each are independently selected from H, hydroxy, halogen, cyano, —$SR^{11}$, —$S(O)R^{11}$, —$S(O)_2R^{12}$, —$S(O)_2NR^{11}R^{12}$, $C_1$-$C_8$ haloalkyl, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)—$OR^{12}$, -alkylC(O)$NR^{11}R^{12}$, -alkenylC(O)$OR^{12}$, -alkenylC(O)$NR^{11}R^{12}$, -aryl(CH$_2$)$_m$C(O)$OR^{12}$, -aryl(CH$_2^1$)$_m$C(O)$NR^{11}R^{12}$, —$NR^{11}R^{12}$, —(CH$_2$)$_m$C(O)$NR^{11}S(O)_2R^{12}$, -aryl(CH$_2$)$_m$—C(O)$NR^{11}S(O)_2R^{12}$, —(CH$_2$)$_m$S(O)$_2NR^{11}C(O)R^{12}$, -aryl(CH$_2$)$_m$S(O)$_2NR^{11}C(O)R^{12}$, —XZ, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxyC$_1$-$C_8$ alkylamino;

$R^7$ is hydrogen;

When $R^4$ is $L^4$ or $M^4$, $R^8$ is selected from H, hydroxy, halogen, $CF_3$, cyano, —$SR^{11}$, —$S(O)R^{11}$, —(CH$_2$)$_m$C(O)—$OR^{12}$, —(CH$_2$)$_m$C(O)$NR^{11}R^{12}$—$S(O)_2R^{12}$, —$S(O)_2NR^{11}R^{12}$, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$C(O)(CH_2)_m$aryl, —$C(=NR^{11})NR^{11}R^{12}$, —$NR^{11}C(=NR^{11})NR^{11}R^{12}$, —$C_1$-$C_8$ haloalkyl, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)$OR^{12}$, -alkylC(O)$NR^{11}R^{12}$, -alkenylC(O)$OR^{12}$, -alkenylC(O)$NR^{11}R^{12}$, -aryl(CH$_2$)$_m$C(O)$OR^{12}$, -aryl(CH$_2$)$_m$C(O)$NR^{11}R^{12}$, —$NR^{11}R^{12}$, —(CH$_2$)$_m$C(O)$NR^{11}S(O)_2R^{12}$, -aryl(CH$_2$)$_m$C(O)$NR^{11}S(O)_2R^{12}$, —(CH$_2$)$_m$S(O)$_2NR^{11}C(O)R^{12}$, -aryl(CH$_2$)$_m$S(O)$_2NR^{11}C(O)R^{12}$, —XZ, or alkynyl-phenyl optionally substituted with halogen, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxyC$_1$-$C_8$ alkylamino; or When $R^4$ is $T^4$, $R^8$ is selected from —C(O)OH, —C(O)$NR^{11}R^{12}$, $C(O)R^{12}$, —$NR^{11}C(O)R^{12}$, —$NR^{11}C(O)OR^{12}$, -alkylC(O)OH, -alkenylC(O)OH, -aryl(CH$_2$)$_m$C(O)OH, -aryl(CH$_2$)$_m$C(O)$OR^{12}$, -alkylC(O)$NR^{11}R^{12}$, -aryl(CH$_2$)$_m$C(O)$NR^{11}R^{12}$, —$B(OH)_2$, tetrazole, carboxylic acid biostere, —$NR^{11}R^{12}$, —$S(O)_2R^{12}$, —$S(O)_2NR^{11}R^{12}$, —(CH$_2$)$_m$C(O)$NR^{ii}S(O)R$ aryl(CH$_2$)$_m$C(O)$NR^{11}S(O)_2R^{12}$, —(CH$_2$)$_m$S(O)$_2NR^{11}C(O)R^{12}$, and -aryl-(CH$_2$)$_m$S(O)$_2NR^{11}C(O)R^{12}$ or $C_3$-$C_6$ heterocycle or monocyclic heteroaryl, optionally substituted with halogen;

X is $C_1$-$C_8$ alkylene, $C_2$-$C_8$ alkenylene, $C_2$-$C_8$ alkynylene, —C(O) or —S(O)$_2$;

Z is H, $CF_3$, —$C_1$-$C_8$ alkyl, $C_3$-$C_8$ cycloalkyl, $C_1$-$C_8$ alkoxy, amino, $C_1$-$C_8$ alkylthio, aryl, or $C_3$-$C_6$ heterocycle or monocyclic heteroaryl, optionally substituted with halogen;

m is 0, 1, 2, 3, or 4;

$R^{10}$ is H, $CF_3$, $C_1$-$C_8$ alkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{11}$, —$NR^{11}R^{12}$, —$SR^{11}$, —$S(O)R^{11}$, —$S(O)_2R^{12}$, or —$S(O)_2NR^{11}R^{12}$;

$R^{11}$, $R^{12}$, and $R^{13}$ are independently H, $C_1$-$C_8$ alkyl, $C_1$-$C_8$ fluoroalkyl, aryl, benzyl, $C_{2-8}$ alkenyl, $C_{2-8}$ alkynyl, -alkyl-C(O)$OR^{14}$, -alkenyl-C(O)$OR^{14}$C(O)$R^{14}$, monocylic heteroaryl, or monocylic heterocycle; and $R^{14}$ is H, $C_1$-$C_8$ alkyl, $C_1$-$C_8$ haloalkyl, aryl, or benzyl.

In some embodiments, a compound of Formula (I) has the structure of Formula (II):

wherein, $R^1$ and $R^2$ are independently H, halogen, $C_1$-$C_8$ alkyl, —$NR^{11}R^{12}$, —$SR^{13}$, $C_3$-$C_6$ heteroalkyl, aryl or a monocyclic heteroaryl; or $R^1$ and $R^2$ together with the carbon to which they are attached form a $C_3$-$C_8$ cycloalkyl or heterocycloalkyl;

$L^4$ is

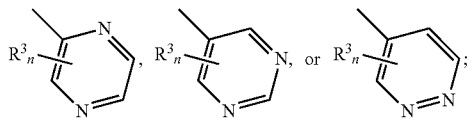

wherein, n is 1 or 2;

$R^3$ is H, halogen, —$OR^{11}$, —$NR^{11}R^{12}$, —$S(O)R^{11}$, —$S(O)_2 R^{12}$, —$S(O)_2NR^{11}R^{12}$, $C_1$-$C_8$ haloalkyl, $C_1$-$C_8$ alkyl, $C_1$-$C_8$ alkoxy, cyano, $C_1$-$C_8$ alkylamino, $C_1$-$C_8$ alkoxyamino, aryl, monocyclic heteroaryl or monocyclic heterocycle; and $R^6$ and $R^9$ each are independently selected from H, hydroxy, halogen, cyano, —$SR^{11}$, —$S(O)R^{11}$, —$S(O)_2R^{12}$, —$S(O)_2NR^{11}R^{12}$, $C_1$-$C_8$ haloalkyl, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)—$OR^{12}$, -alkylC(O)$NR^{11}R^{12}$, -alkenylC(O)$OR^{12}$, -alkenylC(O)$NR^{11}R^{12}$, -aryl$(CH_2)_mC(O)OR^{12}$, -aryl$(CH_2)_mC(O)NR^{11}R^{12}$, —$NR^{11}R^{12}$, —$(CH_2)_mC(O)NR^{11}S(O)R^{12}$, -aryl$(CH_2)_m$—$C(O)NR^{11}S(O)_2R^{12}$, —$(CH_2)_mS(O)_2NR^{11}C(O)R^{12}$, -aryl$(CH_2)_mS(O)_2NR^{11}C(O)R^{12}$, —XZ, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

$R^7$ is hydrogen;

$R^8$ is selected from H, hydroxy, halogen, $CF_3$, cyano, —$SR^{11}$, —$S(O)R^{11}$, —$(CH_2)_mC(O)$—$OR^{12}$, —$(CH_2)_mC(O)NR^{11}R^{12}$—$S(O)_2R^{12}$, —$S(O)_2NR^{11}R^{12}$, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$C(O)(CH_2)_m$aryl, —$C(=NR^{11})NR^{11}R^{12}$, —$NR^{11}C(=NR^{11})NR^{11}R^{12}$, —$C_1$-$C_8$ haloalkyl, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)$OR^{12}$, -alkylC(O)$NR^{11}R^{12}$, -alkenylC(O)$OR^{12}$, -alkenylC(O)$NR^{11}R^{12}$, -aryl$(CH_2)_mC(O)OR^{12}$, -aryl$(CH_2)_mC(O)NR^{11}R^{12}$, —$NR^{11}R^{12}$, —$(CH_2)_mC(O)NR^{11}S(O)_2R^{12}$, -aryl$(CH_2)_mC(O)NR^{11}S(O)_2R^{12}$, —$(CH_2)_mS(O)_2NR^{11}C(O)R^{12}$, -aryl$(CH_2)_mS(O)_2NR^{11}C(O)R^{12}$, —XZ, or alkynyl-phenyl optionally substituted with halogen, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

X is $C_1$-$C_8$ alkylene, $C_2$-$C_8$ alkenylene, $C_2$-$C_8$ alkynylene, —C(O) or —$S(O)_2$;

Z is H, $CF_3$, —$C_1$-$C_8$ alkyl, $C_3$-$C_8$ cycloalkyl, $C_1$-$C_8$ alkoxy, amino, $C_1$-$C_8$ alkylthio, aryl, $C_3$-$C_6$ heterocycle or monocyclic heteroaryl, optionally substituted with halogen;

m is 0, 1, 2, 3, or 4;

$R^{10}$ is H, $CF_3$, $C_1$-$C_8$ alkyl, —$C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{11}$, —$NR^{11}R^{12}$, —$SR^{11}$, —$S(O)R^{11}$, —$S(O)_2R^{12}$, or —$S(O)_2NR^{11}R^{12}$;

$R^{11}$, $R^{12}$, and $R^{13}$ are independently H, $C_1$-$C_8$ alkyl, $C_1$-$C_8$ fluoroalkyl, aryl, benzyl, $C_{2-8}$ alkenyl, $C_{2-8}$ alkynyl, -alkyl-C(O)$OR^{14}$, -alkenyl-C(O)$OR^{14}$—$C(O)R^{14}$, monocylic heteroaryl, or monocylic heterocycle; and $R^{14}$ is H, $C_1$-$C_8$ alkyl, $C_1$-$C_8$ fluoroalkyl, aryl, or benzyl.

In one embodiment of Formula (II), $R^3$ is H, $OR^{11}$, —$C_1$-$C_8$ alkylfluoro, —$C_1$-$C_8$ alkyl, or $C_1$-$C_8$ alkoxy.

In another embodiment of Formula (II), $R^1$, $R^2$ and $R^{10}$ are H; $L^4$ is

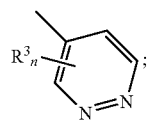

$R^8$ is halogen, $CF_3$, cyano, thiophene, imidazole, tetraazole, —$(CH_2)_mC(O)OR^{12}$, —$(CH_2)_mC(O)NR^{11}R^{12}$, -aryl$(CH_2)_mC(O)OR^{12}$, -aryl$(CH_2)_mC(O)NR^{11}R^{12}$, —$NR^{11}R^{12}$, phenyl optionally substituted with halogen or alkynyl-phenyl optionally substituted with halogen; wherein m is 0, 1, 2, or 3; and $R^{12}$ is H or $C_1$-$C_6$ alkyl.

In still another embodiment of Formula (II), $R^1$, $R^2$ and $R^{10}$ are H; $L^4$ is

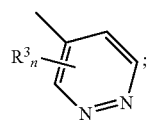

wherein, $R^3$ is hydrogen; $R^8$ is halogen, $CF_3$, cyano, thiophene, imidazole, tetrazole, —$(CH_2)_mC(O)OR^{12}$, —$(CH_2)_mC(O)NR^{11}R^{12}$, -aryl$(CH_2)_mC(O)OR^{12}$, -aryl$(CH_2)_mC(O)NR^{11}R^{12}$, —$NR^{11}R^{12}$, phenyl optionally substituted with halogen or alkynyl-phenyl optionally substituted with halogen; wherein m is 0, 1, 2, or 3; $R^{12}$ is H or $C_1$-$C_6$ alkyl; and $R^6$ and $R^9$ are hydrogen.

In other embodiments of Formula (II), $R^1$, $R^2$ and $R^{10}$ are H; $L^4$ is

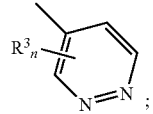

wherein, $R^3$ is hydrogen; $R^8$ is halogen, $CF_3$, cyano, thiophene, imidazole, tetrazole, —$(CH_2)_mC(O)$—$OR^{12}$, —$(CH_2)_mC(O)NR^{11}R^{12}$, aryl$(CH_2)_mC(O)OR^{12}$, aryl$(CH_2)_mC(O)NR^{11}R^{12}$, —$NR^{11}R^{12}$, phenyl optionally substituted with halogen or alkynyl-phenyl optionally substituted with halogen; wherein m is 0, 1, 2, or 3; and $R^{12}$ is H or $C_1$-$C_6$ alkyl.

In some embodiments, a compound of Formula (I) has the structure of Formula (III):

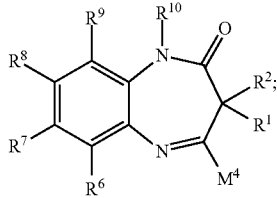

wherein:

$R^1$ and $R^2$ are independently H, halogen, $C_1$-$C_8$ alkyl, —$NR^{11}R^{12}$, —$SR^{13}$, $C_3$-$C_6$ heteroalkyl, aryl or a monocyclic heteroaryl; or $R^1$ and $R^2$ together with the carbon to which they are attached form a $C_3$-$C_8$ cycloalkyl or heterocycloalkyl;

$M^4$ is a substituted or unsubstituted bicyclic heteroaryl or a substituted or unsubstituted bicyclic heterocycle, optionally substituted with 1 to 2 $R^3$ substituents;

$R^3$ is H, halogen, —$OR^{11}$, —$NR^{11}R^{12}$, —$SR^{11}$, —$S(O)R^{11}$, —$S(O)_2R^{12}$, $C_1$-$C_8$ haloalkyl, $C_1$-$C_8$ alkyl, $C_1$-$C_8$ alkoxy, cyano, $C_1$-$C_8$ alkylamino, $C_1$-$C_8$ alkoxyamino, aryl, monocyclic heteroaryl or monocyclic heterocycle; and $R^6$ and $R^9$ each are independently selected from H, hydroxy, halogen, cyano, —$SR^{11}$, —$S(O)R^{11}$, —$S(O)_2R^{12}$, —$S(O)_2NR^{11}R^{12}$, $C_1$-$C_8$ haloalkyl, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)—$OR^{12}$, -alkylC(O)$NR^{11}R^{12}$, -alkenylC(O)$OR^{12}$, -alkenylC(O)$NR^{11}R^{12}$, -aryl(CH$_2$)$_m$C(O)$OR^{12}$, -aryl(CH$_2$)$_m$C(O)$NR^{11}R^{12}$, —$NR^{11}R^{12}$, —(CH$_2$)$_m$C(O)$NR^{11}S(O)_2R^{12}$, -aryl(CH$_2$)$_m$—C(O)$NR^{11}S(O)_2R^{12}$, —(CH$_2$)$_m$S(O)$_2NR^{11}C(O)R^{12}$, -aryl(CH$_2$)$_m$S(O)$_2NR^{11}C(O)R^{12}$, —XZ, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, CF$_3$, $C_1$-$C_8$ alkyl, $C_1$-$C_8$ alkoxy, cyano, amino, $C_1$-$C_8$ alkylamino, and $C_1$-$C_8$ alkoxyC$_1$-$C_8$ alkylamino;

$R^7$ is hydrogen;

$R^8$ is selected from H, hydroxy, halogen, CF$_3$, cyano, —$SR^{11}$, —$S(O)R^{11}$, —(CH$_2$)$_m$C(O)—$OR^{12}$, —(CH$_2$)$_m$C(O)$NR^{11}R^{12}$—$S(O)_2R^{12}$, —$S(O)_2NR^{11}R^{12}$, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$C(O)(CH_2)_m$aryl, —$C(=NR^{11})NR^{11}R^{12}$, —$NR^{11}C(=NR^{11})NR^{11}R^{12}$, —$C_1$-$C_8$ haloalkyl, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)$OR^{12}$, -alkylC(O)$NR^{11}R^{12}$, -alkenylC(O)$OR^{12}$, -alkenylC(O)$NR^{11}R^{12}$, -aryl(CH$_2$)$_m$C(O)$OR^{12}$, -aryl(CH$_2$)$_m$C(O)$NR^{11}R^{12}$, —$NR^{11}R^{12}$, —(CH$_2$)$_m$C(O)$NR^{11}S(O)_2R^{12}$, -aryl(CH$_2$)$_m$C(O)$NR^{11}S(O)_2R^{12}$, —(CH$_2$)$_m$S(O)$_2NR^{11}C(O)R^{12}$, -aryl(CH$_2$)$_m$S(O)$_2NR^{11}C(O)R^{12}$, —XZ, or alkynyl-phenyl optionally substituted with halogen, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, CF$_3$, $C_1$-$C_8$ alkyl, $C_1$-$C_8$ alkoxy, cyano, amino, $C_1$-$C_8$ alkylamino, and $C_1$-$C_8$ alkoxyC$_1$-$C_8$ alkylamino;

X is $C_1$-$C_8$ alkylene, $C_2$-$C_8$ alkenylene, $C_2$-$C_8$ alkynylene, —C(O) or —S(O)$_2$;

Z is H, CF$_3$, —$C_1$-$C_8$ alkyl, $C_3$-$C_8$ cycloalkyl, $C_1$-$C_8$ alkoxy, amino, $C_1$-$C_8$ alkylthio, aryl, $C_3$-$C_6$ heterocycle or monocyclic heteroaryl, optionally substituted with halogen;

m is 0, 1, 2, 3, or 4;

$R^{10}$ is H, CF$_3$, $C_1$-$C_8$ alkyl, —$C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{11}$, —$NR^{11}R^{12}$, —$SR^{11}$, —$S(O)R^{11}$, —$S(O)_2R^{12}$, or —$S(O)_2NR^{11}R^{12}$;

$R^{11}$, $R^{12}$, and $R^{13}$ are independently H, $C_1$-$C_8$ alkyl, $C_1$-$C_8$ fluoroalkyl, aryl, benzyl, $C_{2-8}$ alkenyl, $C_{2-8}$ alkynyl, -alkylC(O)$OR^{14}$, -alkenylC(O)$OR^{14}$—$C(O)R^{14}$, monocylic heteroaryl, or monocylic heterocycle; and $R^{14}$ is H, $C_1$-$C_8$ alkyl, $C_1$-$C_8$ fluoroalkyl, aryl, or benzyl.

In one embodiment of Formula (III), $R^1$, $R^2$ and $R^{10}$ are hydrogen; $R^3$ is hydrogen; $R^8$ is halogen, CF$_3$, cyano, thiophene, imidazole, tetrazole, —(CH$_2$)$_m$C(O)—$OR^{12}$, —(CH$_2$)$_m$C(O)$NR^{11}R^{12}$-aryl-(CH$_2$)$_m$C(O)$OR^{12}$, -aryl (CH$_2$)$_m$C(O)$NR^{11}R^{12}$, —$NR^{11}R^{12}$, or phenyl optionally substituted with halogen; wherein m is 0, 1, 2, or 3; $R^{12}$ is H or $C_1$-$C_6$ alkyl.

In various embodiments of Formula (III), $R^1$, $R^2$ and $R^{10}$ are hydrogen; $M^4$ is

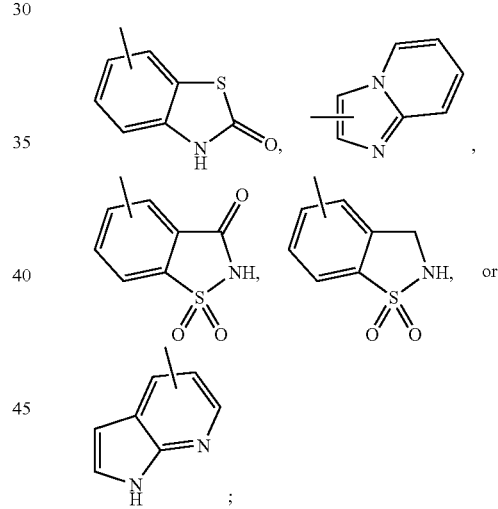

$R^8$ is halogen, CF$_3$, cyano, thiophene, imidazole, tetrazole, —(CH$_2$)$_m$C(O)$OR^{12}$, —(CH$_2$)$_m$C(O)$NR^{11}R^{12}$, -aryl(CH$_2$)$_m$C(O)$OR^{12}$, -aryl(CH$_2$)$_m$C(O)$NR^{11}R^{12}$, —$NR^{11}R^{12}$, phenyl optionally substituted with halogen or alkynyl-phenyl optionally substituted with halogen; wherein m is 0, 1, 2, or 3; $R^{12}$ is H or $C_1$-$C_6$ alkyl; and $R^6$ and $R^9$ are hydrogen.

In other embodiments of Formula (III), $R^1$, $R^2$ and $R^{10}$ are hydrogen; $M^4$ is

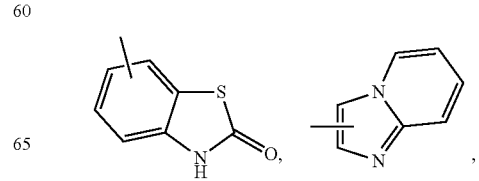

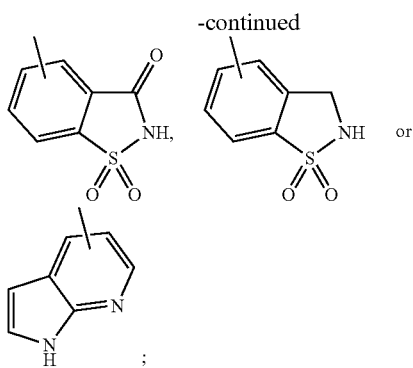

$R^6$ and $R^9$ are hydrogen; $R^8$ is halogen, $CF_3$, cyano, thiophene, imidazole, tetrazole, $-(CH_2)_mC(O)OR^{12}$, $-(CH_2)_mC(O)NR^{11}R^{12}$, aryl$(CH_2)_mC(O)OR^{12}$, aryl$(CH_2)_m$ $C(O)NR^{11}R^{12}$, $-NR^{11}R^{12}$, phenyl optionally substituted with halogen or alkynyl-phenyl optionally substituted with halogen; wherein m is 0, 1, 2, or 3; and $R^{12}$ is H or $C_1$-$C_6$ alkyl.

In some embodiments, a compound of Formula (I) has the structure of Formula (IV):

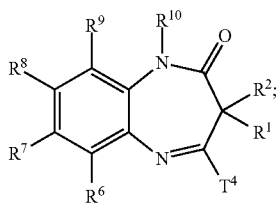

wherein $R^1$ and $R^2$ are independently H, halogen, $C_1$-$C_8$ alkyl, $-NR^{11}R^{12}$, $-SR^{13}$, $C_3$-$C_6$ heteroalkyl, aryl or a monocyclic heteroaryl; or $R^1$ and $R^2$ together with the carbon to which they are attached form a $C_3$-$C_8$ cycloalkyl or heterocycloalkyl;

$T^4$ is substituted or unsubstituted aryl or substituted or unsubstituted monocyclic heteroaryl containing 1 heteroatom selected from O or N optionally substituted with 1 to 2 $R^3$ substituents;

$R^3$ is H, halogen, $-OR^{11}$, $-NR^{11}R^{12}$, $-S(O)R^{11}$, $-S(O)_2R^{12}$, $S(O)_2NR^{11}R^{12}$, $C_1$-$C_8$ haloalkyl, $C_1$-$C_8$ alkyl, $C_1$-$C_8$ alkynyl, $C_1$-$C_8$ alkoxy, cyano, $C_1$-$C_8$ alkylamino, $C_1$-$C_8$ alkoxyamino, aryl, monocyclic heteroaryl or monocyclic heterocycle; and $R^6$ and $R^9$ each are independently selected from H, hydroxy, halogen, cyano, $-SR^{11}$, $-S(O)R^{11}$, $-S(O)_2R^{12}$, $-S(O)_2NR^{11}R^{12}$, $C_1$-$C_8$ haloalkyl, $-C(O)OR^{12}$, $-C(O)NR^{11}R^{12}$, $-C(O)R^{12}$, $-NR^{11}C(O)R^{12}$, $-NR^{11}S(O)_2R^{12}$, $-NR^{11}C(O)OR^{12}$, $-B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, substituted or unsubstituted aryl, -alkylC(O)—$OR^{12}$, -alkylC(O)$NR^{11}R^{12}$, -alkenylC(O)$OR^{12}$, -alkenylC(O)$NR^{11}R^{12}$, -aryl$(CH_2)_mC(O)OR^{12}$, -aryl$(CH_2)_mC(O)NR^{11}R^{12}$, $-NR^{11}R^{12}$, $-(CH_2)_mC(O)NR^{11}S(O)_2R^{12}$, -aryl$(CH_2)_m$—$C(O)NR^{11}S(O)_2R^{12}$, $-(CH_2)_mS(O)_2NR^{11}C(O)$ $R^{12}$, -aryl$(CH_2)_mS(O)_2NR^{11}C(O)R^{12}$, —XZ, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

$R^7$ is hydrogen;

$R^8$ is selected from $-C(O)OH$, $-C(O)NR^{11}R^{12}$, $-C(O)R^{12}$, $-NR^{11}-C(O)R^{12}$, $-NR^{11}-C(O)R^{12}$, $-NR^{11}C(O)$ $OR^{12}$, -alkylC(O)OH, -alkenylC(O)OH, -aryl$(CH_2)_mC(O)$ OH, -alkylC(O)$NR^{11}R^{12}$, -aryl$(CH_2)_mC(O)NR^{11}R^{12}$, $-B(OH)_2$, tetrazole, carboxylic acid biostere, $-NR^{11}R^{12}$, $-S(O)_2R^{12}$, $-S(O)_2NR^{11}R^{12}$, $-(CH_2)_mC(O)NR^{11}S(O)_2$ $R^{12}$, -aryl$(CH_2)_mC(O)NR^{11}S(O)_2R^{12}$, $-(CH_2)_nS(O)_2$— $NR^{11}C(O)R^{12}$ and -aryl$(CH_2)_mS(O)_2NR^{11}C(O)R^{12}$;

X is $C_1$-$C_8$ alkylene, $C_2$-$C_8$ alkenylene, $C_2$-$C_8$ alkynylene, $-C(O)$ or $-S(O)_2$;

Z is H, $CF_3$, $-C_1$-$C_8$ alkyl, $C_3$-$C_8$ cycloalkyl, $C_1$-$C_8$ alkoxy, amino, $C_1$-$C_8$ alkylthio, aryl, $C_3$-$C_6$ heterocycle or monocyclic heteroaryl, optionally substituted with halogen;

m is 0, 1, 2, 3, or 4;

$R^{10}$ is H, $CF_3$, $C_1$-$C_8$ alkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, $OR^{11}$, $-NR^{11}R^{12}$, $SR^{11}$, $-S(O)R^{11}$, $-S(O)_2R^{12}$, or $-S(O)_2$ $NR^{11}R^{12}$;

$R^{11}$, $R^{12}$, and $R^{13}$ are independently H, $C_1$-$C_8$ alkyl, $C_1$-$C_8$ fluoroalkyl, aryl, benzyl, $C_{2-8}$ alkenyl, $C_{2-8}$ alkynyl, -alkylC (O)$OR^{14}$, -alkenylC(O)$OR^{14}$C(O)$R^{14}$, monocyclic heteroaryl, or monocylic heterocycle; and $R^{14}$ is H, $C_1$-$C_8$ alkyl, $C_1$-$C_8$ fluoroalkyl, aryl, or benzyl.

In one embodiment of Formula (IV), $R^1$, $R^2$ and $R^{10}$ are hydrogen; $T^4$ is

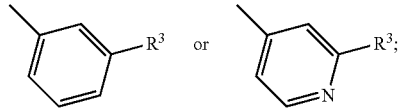

$R^3$ is H, halogen, $OR^{11}$, $C_1$-$C_8$ alkylfluoro, $C_1$-$C_8$ alkyl, $C_1$-$C_8$ alkynyl, $C_1$-$C_8$ alkoxy, cyano, aryl, monocyclic heteroaryl or monocyclic heterocycle; and m is 0, 1, 2, or 3; and $R^{12}$ is H or $C_1$-$C_6$ alkyl.

In one embodiment of Formula (IV), $R^1$, $R^2$ and $R^{10}$ are hydrogen; $T^4$ is

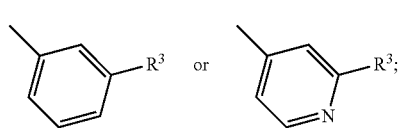

$R^3$ is H, Cl, cyano, aryl, or monocyclic heteroaryl; and $R^8$ is -alkylC(O)OH, -alkenylC(O)OH, -aryl$(CH_2)_mC(O)$OH, -alkylC(O)$NR^{11}R^{12}$, -aryl$(CH_2)_mC(O)NR^{11}R^{12}$, $B(OH)_2$, tetrazole, or $-S(O)_2R^{12}$; wherein m is 0, 1, 2, or 3; $R^6$ and $R^9$ are hydrogen; and $R^{12}$ is H or $C_1$-$C_6$ alkyl.

Specific examples of compounds useful in the invention described herein include: 8-Bromo-4-(pyridazin-4-yl)-1H-benzo[b][1,4]diazepin-2(3H)-one (Compound 1); 8-Trifluoromethyl-4-(pyridazin-4-yl)-1H-benzo[b][1,4]diazepin-2 (3H)-one (Compound 2); 8-Iodo-4-(pyridazin-4-yl)-1H-benzo[b][1,4]diazepin-2(3H)-one (Compound 3); Methyl 2-oxo-4-(pyridazin-4-yl)-2,3-dihydro-1H-benzo[b][1,4]diazepine-8-carboxylate (Compound 4); 8-Chloro-4-(pyridazin-4-yl)-1H-benzo[b][1,4]diazepin-2(3H)-one (Compound 5); 8-Fluoro-4-(pyridazin-4-yl)-1H-benzo[b][1,4] diazepin-2(3H)-one (Compound 6); 8-Bromo-4-(pyrimidin- 3-yl)-1H-benzo[b][1,4]diazepin-2(3H)-one (Compound 7); 8-Bromo-4-(pyrazin-2-yl)-1H-benzo[b][1,4]diazepin-2 (3H)-one (Compound 8); 8-Bromo-4-(5-methylpyridazin-2-yl)-1H-benzo[b][1,4]diazepin-2(3H)-one (Compound 9); 8-Bromo-4-(5-chloropyridazin-2-yl)-1H-benzo[b][1,4]diazepin-2(3H)-one (Compound 10); 8-Bromo-4-(5-hydroxypyridazin-4-yl)-1H-benzo[b][1,4]diazepin-2(3H)-one (Compound 11); 2-Oxo-4-(pyridazin-4-yl)-2,3-dihydro-1H-benzo[b][1,4]diazepine-8-carboxylic acid (Compound 12); 7,8-Dimethyl-4-(pyridazin-4-yl)-1H-benzo[b][1,4]diazepin-2(3H)-one (Compound 13); 8-Bromo-4-(pyridazin-4-yl)-1H-benzo[b][1,4]diazepin-2(3H)-one (Compound 14); 8-(Thiophen-2-yl)-4-(pyridazin-4-yl)-1H-benzo[b][1,4]diazepin-2(3H)-one (Compound 15); 8-(2-Fluorophenyl)-4-(pyridazin-4-yl)-1H-benzo[b][1,4]diazepin-2(3H)-one (Compound 16); 8-(3,4-Dimethoxyphenyl)-4-(pyridazin-4-yl)-1H-benzo[b][1,4]diazepin-2(3H)-one (Compound 17); 2-oxo-4-(pyridazin-4-yl)-2,3-dihydro-1H-benzo[b][1,4]diazepine-8-carbonitrile (Compound 18); 8-Benzoyl-4-(pyridazin-4-yl)-1H-benzo[b][1,4]diazepin-2(3H)-one (Compound 19); 8-Bromo-6-methyl-4-(pyridazin-4-yl)-1H-benzo[b][1,4]diazepin-2(3H)-one (Compound 20); 8-Bromo-7-chloro-4-(pyridazin-4-yl)-1H-benzo[b][1,4]diazepin-2(3H)-one (Compound 21); 8-Bromo-6-trifluoromethyl-4-(pyridazin-4-yl)-1H-benzo[b][1,4]diazepin-2(3H)-one (Compound 22); 8-Bromo-6-iodo-4-(pyridazin-4-yl)-1H-benzo[b][1,4]diazepin-2(3H)-one (Compound 23); 7,8-Dibromo-4-(pyridazin-4-yl)-1H-benzo[b][1,4]diazepin-2(3H)-one (Compound 24); 8-Bromo-7-methoxy-4-(pyridazin-4-yl)-1H-benzo[b][1,4]diazepin-2(3H)-one (Compound 25); 8-Bromo-7-trifluoromethyl-4-(pyridazin-4-yl)-1H-benzo[b][1,4]diazepin-2(3H)-one (Compound 26); 8-Bromo-7-hydroxy-4-(pyridazin-4-yl)-1H-benzo[b][1,4]diazepin-2(3H)-one (Compound 27); 7-Bromo-4-(pyridazin-4-yl)-1H-benzo[b][1,4]diazepin-2(3H)-one (Compound 28); 8-Bromo-7-methyl-4-(pyridazin-4-yl)-1H-benzo[b][1,4]diazepin-2(3H)-one (Compound 29); 8-Phenyl-4-(pyridazin-4-yl)-1H-benzo[b][1,4]diazepin-2(3H)-one (Compound 30); 8-(3,5-Difluorophenyl)-4-(pyridazin-4-yl)-1H-benzo[b][1,4]diazepin-2(3H)-one (Compound 31); 8-Bromo-4-(5-methylpyridazin-2-yl)-1H-benzo[b][1,4]diazepin-2(3H)-one (Compound 32); 8-Bromo-4-(6-hydroxypyridazin-3-yl)-1H-benzo[b][1,4]diazepin-2(3H)-one (Compound 33); 8-Bromo-4-(imidazo[1,2-a]pyridin-3-yl)-1H-benzo[b][1,4]diazepin-2(3H)-one (Compound 34); 6-(8-Bromo-2-oxo-2,3-dihydro-1H-benzo[b][1,4]diazepin-4-yl)benzo[d]thiazol-2(3H)-one (Compound 35); 648-((2-Fluorophenyl)ethynyl)-2-oxo-2,3-dihydro-1H-benzo[b][1,4]diazepin-4-yl)benzo[8]-thiazol-2(3H)-one (Compound 36); 8-(1H-Imidazol-1-yl)-4-(pyridazin-4-yl)-1H-benzo[b][1,4]diazepin-2(3H)-one (Compound 37); 8-Bromo-6-fluoro-4-(pyridazin-4-yl)-1H-benzo[b][1,4]diazepin-2(3H)-one (Compound 38); 4-(Pyridazin-4-yl)-8-(2,3,4-trifluorophenyl)-1H-benzo[b][1,4]diazepin-2(3H)-one (Compound 39); 4-(3-Cyanophenyl)-2-oxo-2,3-dihydro-1H-benzo[b][1,4]diazepine-8-carboxylic acid (Compound 40); 2-(4-(3-Cyanophenyl)-2-oxo-2,3-dihydro-1H-benzo[b][1,4]diazepin-8-yl)benzoic acid (Compound 41); Methyl 4-(3-cyanophenyl)-2-oxo-2,3-dihydro-1H-benzo[b][1,4]diazepine-8-carboxylate (Compound 42).

4-(4-(3-Cyanophenyl)-2-oxo-2,3-dihydro-1H-benzo[b][1,4]diazepin-8-yl)benzoic acid (Compound 43); 4-(3-Cyanophenyl)-2-oxo-N-propyl-2,3-dihydro-1H-benzo[b][1,4]diazepine-8-carboxamide (Compound 44); N-Benzyl-4-(3-cyanophenyl)-2-oxo-2,3-dihydro-1H-benzo[b][1,4]diazepine-8-carboxamide (Compound 45); 3-(4-(3-Cyanophenyl)-2-oxo-2,3-dihydro-1H-benzo[b][1,4]diazepin-8-yl)benzoic acid (Compound 46); 4-(3-Cyanophenyl)-N-methyl-2-oxo-2,3-dihydro-1H-benzo[b][1,4]diazepine-8-carboxamide (Compound 47); 4-(3-Cyanophenyl)-N,N-dimethyl-2-oxo-2,3-dihydro-1H-benzo[b][1,4]diazepine-8-carboxamide (Compound 48); 4-(3-Cyanophenyl)-2-oxo-N-(prop-2-yn-1-yl)-2,3-dihydro-1H-benzo[b][1,4]diazepine-8-carboxamide (Compound 49); Methyl 3-((4-(3-cyanophenyl)-2-oxo-2,3-dihydro-1H-benzo[b][1,4]diazepine-8-carboxamido)methyl)benzoate (Compound 50); Methyl 44(4-(3-cyanophenyl)-2-oxo-2,3-dihydro-1H-benzo[b][1,4]diazepine-8-carboxamido)methyl)benzoate (Compound 51); N-Allyl-4-(3-cyanophenyl)-2-oxo-2,3-dihydro-1H-benzo[b][1,4]diazepine-8-carboxamide (Compound 52); (E)-Methyl 3-(4-(3-cyanophenyl)-2-oxo-2,3-dihydro-1H-benzo[b][1,4]diazepin-8-yl)acrylate (Compound 53); 4-(3-Cyanophenyl)-2-oxo-2,3-dihydro-1H-benzo[b][1,4]diazepine-8-carboxamide (Compound 54); Methyl 2-(4-(3-cyanophenyl)-2-oxo-2,3-dihydro-1H-benzo[b][1,4]diazepine-8-carboxamido)acetate (Compound 55); 2-(4-(3-Cyanophenyl)-2-oxo-2,3-dihydro-1H-benzo[b][1,4]diazepine-8-carboxamido)acetic acid (Compound 56); 3-(8-(Methylsulfonyl)-2-oxo-2,3-dihydro-1H-benzo[b][1,4]diazepin-4-yl)benzonitrile (Compound 57); (E)-3-(4-(3-Cyanophenyl)-2-oxo-2,3-dihydro-1H-benzo[b][1,4]diazepin-8-yl)acrylic acid (Compound 58); 3-(8-Amino-2-oxo-2,3-dihydro-1H-benzo[b][1,4]diazepin-4-yl)benzonitrile (Compound 59); N-(4-(3-Cyanophenyl)-2-oxo-2,3-dihydro-1H-benzo[b][1,4]diazepin-8-yl)acetamide (Compound 60); 4-(3-Cyanophenyl)-2-oxo-N-phenyl-2,3-dihydro-1H-benzo[b][1,4]diazepine-8-carboxamide (Compound 61); N-(4-(3-Cyanophenyl)-2-oxo-2,3-dihydro-1H-benzo[b][1,4]diazepin-8-yl)methanesulfonamide (Compound 62); N-(4-(3-Cyanophenyl)-2-oxo-2,3-dihydro-1H-benzo[b][1,4]diazepin-8-yl)pivalamide (Compound 63); 3-(7-bromo-4-oxo-2,3,4,5-tetrahydro-1H-benzo[b][1,4]diazepin-2-yl)benzonitrile (Compound 64); 4-(2-Chloropyridin-4-yl)-2-oxo-2,3-dihydro-1H-benzo[b][1,4]diazepine-8-carboxylic acid (Compound 65); 4-(2-Cyanopyridin-4-yl)-2-oxo-2,3-dihydro-1H-benzo[b][1,4]diazepine-8-carboxylic acid (Compound 66); 4-(2-Chloropyridin-4-yl)-2-oxo-N-propyl-2,3-dihydro-1H-benzo[b][1,4]diazepine-8-carboxamide (Compound 67);

4-(2-Cyanopyridin-4-yl)-2-oxo-N-propyl-2,3-dihydro-1H-benzo[b][1,4]diazepine-8-carboxamide (Compound 68); 4-(2-Chloropyridin-4-yl)-2-oxo-N-(prop-2-yn-1-yl)-2,3-dihydro-1H-benzo[b][1,4]diazepine-8-carboxamide (Compound 69); 4-(2-Cyanopyridin-4-yl)-2-oxo-N-(prop-2-yn-1-yl)-2,3-dihydro-1H-benzo[b][1,4]diazepine-8-carboxamide (Compound 70); (4-(3-Cyanophenyl)-2-oxo-2,3-dihydro-1H-benzo[b][1,4]diazepin-8-yl)boronic acid (Compound 71); 4-(3-Cyanophenyl)-2-oxo-2,3-dihydro-1H-benzo[b][1,4]diazepine-8-carboximidamide (Compound 72); N-((4-(3-Cyanophenyl)-2-oxo-2,3-dihydro-1H-benzo[b][1,4]diazepin-8-yl)(imino)methyl)-acetamide (Compound 73); 2-Oxo-4-(pyridazin-4-yl)-2,3-dihydro-1H-benzo[b][1,4]diazepine-8-carboxamide (Compound 74); 2-oxo-N-propyl-4-(pyridazin-4-yl)-2,3-dihydro-1H-benzo[b][1,4]diazepine-8-carboxamide (Compound 75); N-Allyl-2-oxo-4-(pyridazin-4-yl)-2,3-dihydro-1H-benzo[b][1,4]diazepine-8-carboxamide (Compound 76).

N-(Methylsulfonyl)-2-oxo-4-(pyridazin-4-yl)-2,3-dihydro-1H-benzo[b][1,4]diazepine-8-carboxamide (Compound 77); 1-Methyl-2-oxo-4-(pyridazin-4-yl)-2,3-dihydro-1H-benzo[b][1,4]diazepine-8-carboxylic acid (Compound 78); 2-(2-oxo-4-(pyridazin-4-yl)-2,3-dihydro-1H-benzo[b][1,4]diazepin-8-yl)benzoic acid (Compound 79); 3-(7-(methylsulfonyl)-4-oxo-4,5-dihydro-1H-benzo[b][1,4]diazepin-2- yl)benzonitrile (Compound 80); 2-(3-cyanophenyl)-4-oxo-2,3,4,5-tetrahydro-1H-benzo[b][1,4]diazepine-7-carboxylic acid (Compound 81).

Other specific examples of compounds useful in the present invention include: 7,8-Dimethyl-4-(pyridazin-4-yl)-1H-benzo[b][1,4]diazepin-2(3H)-one; 8-Bromo-7-chloro-4-(pyridazin-4-yl)-1H-benzo[b][1,4]diazepin-2(3H)-one; 7,8-Dibromo-4-(pyridazin-4-yl)-1H-benzo[b][1,4]diazepin-2(3H)-one; 8-Bromo-7-methoxy-4-(pyridazin-4-yl)-1H-benzo[b][1,4]diazepin-2(3H)-one; 8-Bromo-7-trifluoromethyl-4-(pyridazin-4-yl)-1H-benzo[b][1,4]diazepin-2(3H)-one; 8-Bromo-7-hydroxy-4-(pyridazin-4-yl)-1H-benzo[b][1,4]diazepin-2(3H)-one; 7-Bromo-4-(pyridazin-4-yl)-1H-benzo[b][1,4]diazepin-2(3H)-one; and 8-Bromo-7-methyl-4-(pyridazin-4-yl)-1H-benzo[b][1,4]diazepin-2(3H)-one.

Also provided herein is a pharmaceutical composition comprising a therapeutically effective amount of a compound of Formula (I), Formula (II), Formula (III) or Formula (IV), or a pharmaceutically acceptable salt, solvate, analog, prodrug, isomer or tautomer thereof, and at least one pharmaceutically acceptable inactive ingredient selected from pharmaceutically acceptable diluents, pharmaceutically acceptable excipients, and pharmaceutically acceptable carriers. In some embodiments the pharmaceutical composition further comprises one or more additional therapeutically active agents selected from but not limited to an SSRI, an SNRI, a NDRI, a triple uptake inhibitor, an NMDA antagonist, a cholinesterase inhibitor, a monoamine oxidase inhibitor, lithium or an anticonvulsant. The additional therapeutically active agent may be used to enhance the activity of the compound of Formula (I), Formula (II), Formula (III) or Formula (IV).

DEFINITIONS

As used herein, the term "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. Preferred alk groups have 1-8 carbons. "Alkoxy" and other like terms include an oxygen bonded to an alkyl group. "Alkenyl" and other like terms include carbon chains containing at least one unsaturated carbon-carbon bond. "Alkynyl" and other like terms include carbon chains containing at least one carbon-carbon triple bond. An alkyl group, an alkenyl group and an alkynyl group may be substituted or unsubstituted.

As used herein, the term "cycloalkyl" means carbocycles containing no heteroatoms, and includes mono-, bi- and tri-cyclic saturated carbocycles, as well as fused ring systems. Examples of cycloalkyl include but are not limited today cyclopropyl, cyclobutyl, cyclopentyl, cyclohexyl, cycloheptyl, decahydronaphthalene, adamantyl, indanyl, indenyl, fluorenyl, 1,2,3,4-tetrahydronaphthalene and the like. Preferred cycloalkyls have 3 to 8 carbons. A cycloalkyl group may be substituted or unsubstituted.

As used herein, the term "aryl" means an aromatic substituent that is a single ring or multiple rings fused together. Exemplary aryl groups include, without limitation, phenyl, naphthyl, anthracenyl, pyridinyl, pyrazinyl, pyrimidinyl, triazinyl, thiophenyl, furanyl, pyrrolyl, oxazolyl, isoxazolyl, imidazolyl, thioimidazolyl, oxazolyl, isoxazolyl, triazyolyl, and tetrazolyl groups. Aryl groups that contain one or more heteroatoms (e.g., pyridinyl) are often referred to as "heteroaryl groups." When formed of multiple rings, at least one of the constituent rings is aromatic. In some embodiments, at least one of the multiple rings contain a heteroatom, thereby forming heteroatom-containing aryl groups. Heteroatom-containing aryl groups include, without limitation, benzoxazolyl, benzimidazolyl, quinoxalinyl, benzofuranyl, indolyl, indazolyl, benzimidazolyl, quinolinoyl, and 1H-benzo[δ][1,2,3]triazolyl groups and the like. Heteroatom-containing aryl groups also include aromatic rings fused to a heterocyclic ring comprising at least one heteroatom and at least one carbonyl group. Such groups include, without limitation, dioxo tetrahydroquinoxalinyl and dioxo tetrahydroquinazolinyl groups. An aryl group or a heteroaryl group may be substituted or unsubstituted.

As used herein, the term "arylalkoxy" means an aryl group bonded to an alkoxy group. An arylalkoxy group may be substituted or unsubstituted.

As used herein, the term "arylamidoalkyl" means an aryl-C(O)NR-alkyl or aryl-NRC(O)-alkyl. An arylamidoalkyl group may be substituted or unsubstituted.

As used herein, the term "arylalkylamidoalkyl" means an aryl-alkyl-C(O)NR-alkyl or aryl-alkyl-NRC(O)-alkyl, wherein R is any suitable group listed below. An arylalkylamidoalkyl group may be substituted or unsubstituted.

As used herein, the term "arylalkyl" refers to an aryl group bonded to an alkyl group. An arylalkyl group may be substituted or unsubstituted.

As used herein, the term "halogen" or "halo" refers to chlorine, bromine, fluorine or iodine.

As used herein, the term "haloalkyl" means an alkyl group having one or more halogen atoms (e.g., trifluoromethyl). A haloalkyl group may be substituted or unsubstituted.

As used herein, the term "heteroalkyl" refers to an alkyl moiety which comprises a heteroatom such as N, O, P, B, S, or Si. The heteroatom may be connected to the rest of the heteroalkyl moiety by a saturated or unsaturated bond. Thus, an alkyl substituted with a group, such as heterocycloalkyl, substituted heterocycloalkyl, heteroaryl, substituted heteroaryl, alkoxy, aryloxy, boryl, phosphino, amino, silyl, thio, or seleno, is within the scope of the term heteroalkyl. Examples of heteroalkyls include, but are not limited to, cyano, benzoyl, and substituted heteroaryl groups. For example, 2-pyridyl, 3-pyridyl, 4-pyridyl, and 2-furyl, 3-furyl, 4-furyl, 2-imidazolyl, 3-imidazolyl, 4-imidazolyl, 5-imidazolyl. A heteroalkyl group may be substituted or unsubstituted.

As used herein, the term "heteroarylalkyl" means a heteroaryl group to which an alkyl group is attached. A heteroarylalkyl group may be substituted or unsubstituted.

As used herein, the term "heterocycle" means a monocyclic or polycyclic ring comprising carbon and hydrogen atoms, having 1, 2 or more multiple bonds, and the ring atoms contain at least one heteroatom, specifically 1 to 4 heteroatoms, independently selected from nitrogen, oxygen, and sulfur. Heterocycle ring structures include, but are not limited to, mono-, bi-, and tri-cyclic compounds. Specific heterocycles are monocyclic or bicyclic. Representative heterocycles include cyclic ureas, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrazolyl, azabicyclo[3.2.1]octanyl, hexahydro-1H-quinolizinyl, and urazolyl. A heterocyclic ring may be unsubstituted or substituted.

As used herein, the term "heterocycloalkyl" refers to a cycloalkyl group in which at least one of the carbon atoms in the ring is replaced by a heteroatom (e.g., O, S or N). A heterocycloalkyl group may be substituted or unsubstituted.

As used herein, the term "heterocycloalkylalkyl" means a heterocycloalkyl group to which the an alkyl group is attached. A heterocycloalkylalkyl group may be substituted or unsubstituted.

As used herein, the term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halogen groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, arylalkyl or heteroarylalkyl groups, arylalkoxy or heteroarylalkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$C_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof. In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art.

The compounds described herein may contain one or more double bonds and may thus give rise to cis/trans isomers as well as other conformational isomers. The present invention includes all such possible isomers as well as mixtures of such "isomers".

Compounds described herein that contain a chiral center include all possible stereoisomers of the compound, including compositions comprising the racemic mixture of the two enantiomers, as well as compositions comprising each enantiomer individually, substantially free of the other enantiomer. Thus, for example, contemplated herein is a composition comprising the S enantiomer of a compound substantially free of the R enantiomer, or the R enantiomer substantially free of the S enantiomer. If the named compound comprises more than one chiral center, the scope of the present disclosure also includes compositions comprising mixtures of varying proportions between the diastereomers, as well as compositions comprising one or more diastereomers substantially free of one or more of the other diastereomers. By "substantially free" it is meant that the composition comprises less than 25%, 15%, 10%, 8%, 5%, 3%, or less than 1% of the minor enantiomer or diastereomer(s). Methods for synthesizing, isolating, preparing, and administering various stereoisomers are known in the art.

The present invention also comprises tautomeric forms of the compounds described. Where structural isomers are interconvertible via a low energy barrier, tautomeric isomerism can occur. This can take the form of proton tautomerism in the compounds disclosed for example those containing imino, keto, or oxime groups, or valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

The compounds of this invention may be used in the form of "salts" derived from inorganic or organic acids. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric with replacement of one or both protons, sulfamic, phosphoric with replacement of one or both protons, e.g. orthophosphoric, or metaphosphoric, or pyrophosphoric and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, embonic, nicotinic, isonicotinic and amino acid salts, cyclamate salts, fumaric, toluenesulfonic, methanesulfonic, N-substituted sulphamic, ethane disulfonic, oxalic, and isethionic, and the like. Also, such conventional non-toxic salts include those derived from inorganic acids such as non toxic metals derived from group Ia, Ib, IIa and IIb in the periodic table. For example, lithium, sodium, or potassium magnesium, calcium, zinc salts, or ammonium salts such as those derived from mono, di and trialkyl amines. For example methyl-, ethyl-, diethyl, triethyl, ethanol, diethanol- or triethanol amines or quaternary ammonium hydroxides.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile. Lists of suitable salts are found in *Remington's Pharmaceutical Sciences,* 17th ed., Mack Publishing Company, Easton, Pa., 1985, p. 1418.

As used herein, the term "solvate" means a compound, or a salt thereof, that further includes a stoichiometric or non-stoichiometric amount of solvent bound by non-covalent intermolecular forces. Where the solvent is water, the solvate is a hydrate.

As used herein, the term "analog thereof" in the context of the compounds disclosed herein includes diastereomers, hydrates, solvates, salts, prodrugs, and N-oxides or S-oxides of the compounds.

As used herein, the term "prodrug" in the context of the compounds disclosed herein includes alkoxycarbonyl, substituted alkoxycarbonyl, carbamoyl and substituted carbamoyl or a hydroxyl or other functionality that has been otherwise modified by an organic radical that can be removed under physiological conditions such that the cleavage products are bioavailable and/or active.

The present invention also includes isotopically labeled compounds, which are identical to those recited in the disclosure, but for the fact that one or more atoms are replaced by an atom having an atomic mass or mass number different from the atomic mass or mass number usually found in nature. These isotopically labeled compounds may show greater stability and/or may be used as imaging agents. Examples of isotopes that can be incorporated into compounds of the present invention include isotopes of hydrogen, carbon, nitrogen, oxygen, phosphorous, sulfur, fluorine, chlorine, bromine and iodine such as $^2$H, $^3$H, $^{11}$C, $^{13}$C, $^{14}$C, $^{15}$N, $^{11}$O, $^{17}$O, $^{18}$O, $^{31}$P, $^{32}$P, $^{35}$S, $^{16}$F, $^{18}$F, $^{36}$Cl, $^{76}$Br and $^{123}$I respectively.

"Neurogenesis" is defined herein as proliferation, differentiation, migration and/or survival of a neural cell in vivo or in vitro. In various embodiments, the neural cell is an adult, fetal, or embryonic neural stem cell or population of cells. The cells may be located in the central or peripheral nervous system or elsewhere in a subject or patient. The cells may also be in a tissue, such as neural tissue. In some embodiments, the neural cell is an adult, fetal, or embryonic progenitor cell or population of cells, or a population of cells comprising a mixture of stem cells and progenitor cells. Neural cells include all brain stem cells, all brain progenitor cells, and all brain precursor cells. Neurogenesis includes neurogenesis as it occurs during normal development, as well as neural regeneration that occurs following disease, damage or therapeutic intervention, such as by the treatment described herein.

A "neurogenic agent" is defined as a chemical agent or reagent that can promote, stimulate, or otherwise increase the amount or degree or nature of neurogenesis in vivo or ex vivo or in vitro relative to the amount, degree, or nature of neurogenesis in the absence of the agent or reagent. In some embodiments, treatment with a neurogenic agent increases neurogenesis if it promotes neurogenesis by about 5%, about 10%, about 25%, about 50%, about 100%, about 500%, or more in comparison to the amount, degree, and/or nature of neurogenesis in the absence of the agent, under the conditions of the method used to detect or determine neurogenesis. As described herein, an mGluR2 and/or mGluR3 agonist, antagonist, NAM, PAM or allosteric agonist that promotes, stimulates, or otherwise increases the amount or degree or nature of neurogenesis, by whatever mechanism, is a neurogenic agent. The disclosure further includes compositions comprising a combination of an mGluR2 and/or mGluR3 agonist, antagonist, NAM, PAM or allosteric agonist with one or more neurogenic or neurogenic sensitizing agents as described herein.

A "neurogenic sensitizing agent" is defined as a chemical, biological agent or reagent that when used alone may be neurogenic or non-neurogenic, but when used in combination with a neurogenic agent induces a neurogenic effect, which is greater than the effect of the neurogenic agent alone and is oftentimes synergistic with the neurogenic agent.

The terms "neurogenic modulators" or "neurogenic modulating agents" are defined as an agents when used alone or in combination with one or more other agents induces a change in neurogenesis. In some embodiments, administering "neurogenic modulators" or "neurogenic modulating agents" according to methods provided herein changes neurogenesis in a target tissue and/or cell-type by about 20%, about 25%, about 30%, about 40%, about 50%, about 75%, or about 90% or more in comparison to the absence of the combination. In further embodiments, neurogenesis is modulated by about 95% or by about 99% or more. Preferably the modulation noted is an increase in neurogenesis.

The term "stem cell" (or neural stem cell (NSC)), as used herein, refers to an undifferentiated cell that is capable of self-renewal and differentiation into neurons, astrocytes, and/or oligodendrocytes.

The term "progenitor cell" (e.g., neural progenitor cell), as used herein, refers to a cell derived from a stem cell that is not itself a stem cell. Some progenitor cells can produce progeny that are capable of differentiating into more than one cell type.

The term "mGluR2 and/or mGluR3 agent" refers to an mGluR2 and/or mGluR3 antagonist, PAM, allosteric agonist, or NAM.

The term "mGluR2 and/or mGluR3 PAM" or "PAM" are agents that bind to an allosteric site on the mGluR2 and/or mGluR3 receptor and increase or potentiate the downstream activity of the natural ligand.

The term "mGluR2 and/or mGluR3 allosteric agonist" are agents that bind to an allosteric site on the mGluR2 and/or mGluR3 receptor and activate the downstream activity of the receptor without the influence of the natural ligand.

The term "mGluR2 and/or mGluR3 NAM" or "NAM" includes both non-competitive antagonists and inverse agonists of the mGluR2 and/or mGluR3 receptor. Their utility in the methods described herein include compounds or agents that, under certain conditions, act to decrease or inhibit one or more characteristic responses of a mGlu2 and/or mGlu3 receptor. For example, such NAMs may act by binding to an allosteric site on the mGlu2 and/or mGlu3 receptor thus inhibiting the downstream activity of the natural ligand.

In some embodiments, the mGluR2 and/or mGluR3 agent used in the methods described herein has "selective" activity against one or more mGluR subtypes with respect to the degree and/or nature of activity against one or more other mGluR subtypes. For example, in some embodiments, an mGluR2 and/or mGluR3 antagonist has an antagonist effect against one or more subtypes, and a much weaker effect or substantially no effect against other subtypes. As another example, an mGluR2 and/or mGluR3 antagonist used in the methods described herein may act as an antagonist against one or more mGluR subtypes and as an agonist for one or more other mGluR subtypes. In some embodiments, the mGluR2 and/or mGluR3 agent has activity against mGluR2 and/or mGluR3, while having substantially lesser activity against one or more other mGluR subtypes. In certain embodiments, selective activity of one or more mGluR2 and/or mGluR3 agent results in enhanced efficacy, fewer side effects, lower effective dosages, less frequent dosing, or other desirable attributes.

In some embodiments the selectivity of the mGluR2 and/or mGluR3 agent for either the mGluR2 or mGluR3 is equal or is higher for one receptor over the other.

In some embodiments, the mGluR2 and/or mGluR3 agents are active against one or more additional receptor subtypes.

In other embodiments the mGluR2 and/or mGluR3 agent may affect receptor dimerization. If the mGluR2 and/or mGluR3 is a component of a dimer or heterodimer receptor complex, an mGluR2 and/or mGluR3 agent may affect receptor trafficking and/or affect the binding of other agents to the receptor complex. Additional affects include signaling of the complex as well as signaling of the individual monomers of the receptor complex.

In some embodiments, the term "subject" or "patient" refers to a non-human mammal, such as a primate, canine, or feline or a human being. In some embodiments, the terms refer to an animal that is domesticated (e.g. livestock) or otherwise subject to human care and/or maintenance (e.g. zoo animals and other animals for exhibition). In other non-limiting examples, the terms refer to ruminants or carnivores, such as dogs, cats, birds, horses, cattle, sheep, goats, marine animals and mammals, penguins, deer, elk, and foxes.

As used herein, "treating" includes prevention, amelioration, alleviation, and/or elimination of the disease, disorder, or condition being treated or one or more symptoms of the disease, disorder, or condition being treated, as well as improvement in the overall well being of a patient, as measured by objective and/or subjective criteria. In some embodiments, treating is used for reversing, attenuating, minimizing, suppressing, or halting undesirable or deleterious effects of, or effects from the progression of, a disease, disorder, or condition of the central and/or peripheral nervous systems. In other embodiments, the method of treating may be advantageously used in cases where additional neurogenesis would replace, replenish, or increase the numbers of cells lost due to injury or disease as non-limiting examples.

The term "pharmaceutically acceptable excipient" includes any excipient known in the field as suitable for pharmaceutical application.

Methods of Using the Compounds and Compositions

In some embodiments, the mGluR2 and/or mGluR3 agent may demonstrate synaptic plasticity (Choi, 2011; Zhou, 2011; Harrison, 2008; Mateo, 2007) or may be neurogenic as demonstrated herein. Methods for assessing the nature and/or degree of neurogenesis in vivo and in vitro, for detecting changes in the nature and/or degree of neurogenesis, for identifying neurogenesis modulating agents, for isolating and culturing neural stem cells, for preparing neural stem cells for transplantation or other purposes, and for treating diseases or conditions amenable to stimulating neurogenesis are disclosed, for example, in U.S. Publication Nos. 2010/0009983, 2010/0216734, 2008/0171750, 2007/0015138, 2005/0009742, 2005/0009847, 2005/0032702, 2005/0031538, 2005/0004046, 2004/0254152, 2004/0229291, and 2004/0185429, all of which are herein incorporated by reference in their entirety.

The disclosed embodiments also relate to methods of treating diseases, disorders, and conditions of the central and/or peripheral nervous systems (CNS and PNS, respectively) by administering a compound of Formula I, optionally in combination with another mGluR2 and/or mGluR3 agent and/or another agent (CNS, neurogenic, anti-astrogenic, anti-nausea, etc). The amount of the compound of Formula I, optionally in combination with another agent, may be any that results in a measurable relief of a disease condition like those described herein. As a non-limiting example, an improvement in the Hamilton depression scale (HAM-D) score for depression may be used to determine (such as quantitatively) or detect (such as qualitatively) a measurable level of improvement in the depression of a subject.

Non-limiting examples of symptoms that may be treated with the compounds, compositions, and methods described herein include abnormal behavior, abnormal movement, hyperactivity, hallucinations, acute delusions, combativeness, hostility, negativism, withdrawal, seclusion, memory defects, sensory defects, cognitive defects, pain and tension. Non-limiting examples of abnormal behavior include irritability, poor impulse control, distractibility, and aggressiveness.

In some cases, a compound of Formula I, optionally in combination with one or more other agents, results in improved efficacy, fewer side effects, lower effective dosages, less frequent dosing, and/or other desirable effects relative to use of the neurogenesis modulating agents individually (such as at higher doses), due, e.g., to synergistic activities and/or the targeting of molecules and/or activities that are differentially expressed in particular tissues and/or cell-types.

In other embodiments, modulation by an agent or combination of agents is in a region containing neural cells affected by disease or injury, a region containing neural cells associated with disease effects or processes, or a region containing neural cells affected by other events injurious to neural cells. Non-limiting examples of such events include stroke or radiation therapy of the region. In additional embodiments, a neuromodulating combination substantially modulates two or more physiological activities or target molecules, while being substantially inactive against one or more other molecules and/or activities.

Examples of diseases and conditions treatable by the methods described herein include, but are not limited to, neurodegenerative disorders and neural diseases, such as dementias (e.g., senile dementia, memory disturbances/memory loss, dementias caused by neurodegenerative disorders (e.g., Alzheimer's, Parkinson's disease, Parkinson's disorders, Huntington's disease (Huntington's Chorea), Lou Gehrig's disease, multiple sclerosis, Pick's disease, Parkinsonism dementia syndrome), progressive subcortical gliosis, progressive supranuclear palsy, thalmic degeneration syndrome, hereditary aphasia, amyotrophic lateral sclerosis, Shy-Drager syndrome, and Lewy body disease; vascular conditions (e.g., infarcts, hemorrhage, cardiac disorders); mixed vascular and Alzheimer's; bacterial meningitis; Creutzfeld-Jacob Disease; and Cushing's disease.

The disclosed embodiments also provide for the treatment of a nervous system disorder related to neural damage, cellular degeneration, a psychiatric condition, cellular (neurological) trauma and/or injury (e.g., subdural hematoma or traumatic brain injury), toxic chemicals (e.g., heavy metals, alcohol, some medications), CNS hypoxia, or other neurologically related conditions. In practice, the disclosed compounds, compositions and methods may be applied to a subject or patient afflicted with, or diagnosed with, one or more central or peripheral nervous system disorders in any combination. Diagnosis may be performed by a skilled person in the applicable fields using known and routine methodologies which identify and/or distinguish these nervous system disorders from other conditions.

Non-limiting examples of nervous system disorders related to cellular degeneration include neurodegenerative disorders, neural stem cell disorders, neural progenitor cell disorders, degenerative diseases of the retina, and ischemic disorders. In some embodiments, an ischemic disorder comprises an insufficiency, or lack, of oxygen or angiogenesis, and non-limiting example include spinal ischemia, ischemic stroke, cerebral infarction, multi-infarct dementia. While these conditions may be present individually in a subject or patient, the disclosed methods also provide for the treatment of a subject or patient afflicted with, or diagnosed with, more than one of these conditions in any combination.

Non-limiting examples of nervous system disorders related to a psychiatric condition include neuropsychiatric disorders and affective disorders. As used herein, an affective disorder refers to a disorder of mood such as, but not limited to, depression, post-traumatic stress disorder (PTSD), hypomania, panic attacks, excessive elation, bipolar depression, bipolar disorder (manic-depression), and seasonal mood (or affective) disorder. Other non-limiting examples of neuropsychiatric disorders include schizophrenia and other psychoses, lissencephaly syndrome, anxiety syndromes, anxiety disorders, phobias, stress and related syndromes (e.g., panic disorder, phobias, adjustment disorders, migraines), cognitive function disorders, aggression, drug and alcohol abuse, drug addiction, and drug-induced neurological damage, obsessive compulsive behavior syndromes, borderline personality disorder, non-senile dementia, post-pain depression, post-partum depression, and cerebral palsy.

Examples of nervous system disorders related to cellular or tissue trauma and/or injury include, but are not limited to, neurological traumas and injuries, surgery related trauma and/or injury, retinal injury and trauma, injury related to epilepsy, cord injury, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, brain injury related to substance abuse, and spinal cord injury related to environmental toxin.

Non-limiting examples of nervous system disorders related to other neurologically related conditions include learning disorders, memory disorders, age-associated memory impairment (AAMI) or age-related memory loss, autism, learning or attention deficit disorders (ADD or attention deficit hyperactivity disorder, ADHD), narcolepsy, sleep disorders and sleep deprivation (e.g., insomnia, chronic fatigue syndrome), cognitive disorders, epilepsy, injury related to epilepsy, and temporal lobe epilepsy.

Other non-limiting examples of diseases and conditions treatable by the compounds, compositions, and methods described herein include, but are not limited to, hormonal changes (e.g., depression and other mood disorders associated with puberty, pregnancy, or aging (e.g., menopause)); and lack of exercise (e.g., depression or other mental disorders in elderly, paralyzed, or physically handicapped patients); infections (e.g., HIV); genetic abnormalities (Down syndrome); metabolic abnormalities (e.g., vitamin B12 or folate deficiency); hydrocephalus; memory loss separate from dementia, including mild cognitive impairment (MCI), age-related cognitive decline, and memory loss resulting from the use of general anesthetics, chemotherapy, radiation treatment, post-surgical trauma, or therapeutic intervention; and diseases of the of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc.

Additionally, the disclosed methods provide for the application of a compound of Formula I, optionally in combination with another mGluR2 and/or mGluR3 agent and/or another neurogenic agent, to treat a subject or patient for a condition due to the anti-neurogenic effects of an opiate or opioid based analgesic. In some embodiments, the administration of an opiate or opioid based analgesic, such as an opiate like morphine or other opioid receptor agonist, to a subject or patient results in a decrease in, or inhibition of, neurogenesis. The administration of a compound, optionally in combination with another neurogenic agent, with an opiate or opioid based analgesic would reduce the anti-neurogenic effect.

The disclosed embodiments include a method of treating post operative pain in a subject or patient by combining administration of an opiate or opioid based analgesic with a compound, optionally in combination with another mGluR2 and/or mGluR3 agent and/or another neurogenic agent. The analgesic may have been administered before, simultaneously with, or after the compound, alone or in combination with another neurogenic agent. In some cases, the analgesic or opioid receptor agonist is morphine or another opiate.

Compounds and compositions disclosed herein can also be used to treat diseases of the peripheral nervous system (PNS), including but not limited to, PNS neuropathies (e.g., vascular neuropathies, diabetic neuropathies, amyloid neuropathies, and the like), neuralgias, neoplasms and myelin-related diseases as non-limiting examples.

In some embodiments, a compound of this invention, optionally in combination with another agent, used in the methods described herein, is in the form of a composition that includes at least one pharmaceutically acceptable excipient. Suitable pharmaceutical excipients and formulations are known in the art and are described, for example, in Remington's Pharmaceutical Sciences (19th ed.) (Genarro, ed. (1995) Mack Publishing Co., Easton, Pa.). Pharmaceutical carriers may be chosen by a skilled person based upon the intended mode of administration of the compound of the invention. The pharmaceutically acceptable carrier may include, for example, disintegrants, binders, lubricants, glidants, emollients, humectants, thickeners, silicones, flavoring agents, and water.

The compound may be incorporated with excipients to form a pharmaceutical composition and administered in the form of ingestible tablets, buccal tablets, troches, capsules, elixirs, suspensions, syrups, wafers, or any other form known in the pharmaceutical arts. The pharmaceutical compositions may also be formulated in a sustained release form. Sustained release compositions, enteric coatings, and the like are known in the art. Alternatively, the compositions may be a quick release formulation.

In some embodiments, methods of treatment disclosed herein comprise the step of administering to the subject or patient the compound or pharmaceutical composition thereof, optionally in combination with another agent, for a time and at a concentration sufficient to treat the condition targeted for treatment. The disclosed methods can be applied to individuals having, or who are likely to develop, disorders relating to neural degeneration, neural damage and/or neural demyelination. In some embodiments, a method comprises selecting a population or sub-population of patients, or selecting an individual patient, that is more amenable to treatment and/or less susceptible to side effects than other patients having the same disease or condition. For example, in some embodiments, a sub-population of patients is identified as being more amenable to neurogenesis by taking a cell or tissue sample from prospective patients, isolating and culturing neural cells from the sample, and determining the effect of a compound, optionally in combination with a neurogenic agent, on the degree or nature of neurogenesis, thereby allowing selection of patients for which the compound or combination has a substantial effect on neurogenesis. Advantageously, the selection step(s) results in more effective treatment for the disease or condition that known methods using the same or similar compounds.

Methods described herein may comprise administering to the subject an effective amount of a compound of Formula I, optionally in combination with another agent, or pharmaceutical composition comprising the compound. An effective amount of a composition may vary based on a variety of factors, including but not limited to, the activity of the active compound(s), the physiological characteristics of the subject, the nature of the condition to be treated, and the route and/or method of administration. The disclosed methods typically involve the administration in a dosage range of 0.001 mg/kg/day to 4000 mg/kg/day or in a dosage range of 0.05 to 500 mg/kg/day. Advantageously, methods described herein allow treatment of indications with reductions in side effects, dosage levels, dosage frequency, treatment duration, tolerability, and/or other factors.

Depending on the desired clinical result, the disclosed compounds or pharmaceutical compositions are administered by any means suitable for achieving a desired effect. Various delivery methods are known in the art and can be used to deliver an agent to a subject or patient or within a tissue of interest of said subject or patient. The delivery method will depend on factors such as the tissue of interest, the nature of the compound (e.g., its stability and ability to cross the blood-brain barrier), and the duration of the treatment, among other factors. For example, an osmotic minipump can be implanted into a region, such as the lateral ventricle. Alternatively, compounds can be administered by direct injection into the cerebrospinal fluid of the brain or spinal column, or into the eye.

Compounds can also be administered into the periphery (such as by intravenous or subcutaneous injection, oral or nasal delivery), and subsequently cross the blood-brain bather.

In various embodiments, the disclosed compounds or pharmaceutical compositions are administered in a manner that allows them to cross the blood-brain barrier and in a non-limiting embodiment, reach the desired site for intervention such as the subventricular zone (SVZ) of the lateral ventricles, the dentate gyms of the hippocampus or various sites within the spinal cord. Examples of routes of administration include parenteral, e.g., intravenous, intradermal, subcutaneous, oral (e.g., inhalation), transdermal (topical), transmucosal, spinal and rectal administration. Intranasal administration generally includes, but is not limited to, inhalation of aerosol suspensions for delivery of compositions to the nasal mucosa, trachea and bronchioli.

In some embodiments, a compound of Formula I is administered so as to either pass through or by-pass the blood-brain bather. Methods for allowing these compounds to pass through the blood-brain barrier are known in the art, and include minimizing the size of the compound, providing hydrophobic factors which facilitate passage, and conjugating the compound to a carrier molecule that has substantial permeability across the blood brain barrier. In some instances, a compound of Formula I can be administered by a surgical procedure implanting a catheter coupled to a pump device. The pump device can also be implanted or be extracorporally positioned. Administration of the compound can be in intermittent pulses or as a continuous infusion. Devices for injection to discrete areas of the brain are known in the art. In certain embodiments, the compound is administered locally to the ventricle of the brain, substantia nigra, striatum, locus ceruleous, nucleus basalis Meynert, pedunculopontine nucleus, cerebral cortex, and/or spinal cord by, e.g., injection. Methods, compositions, and devices for delivering therapeutics, including therapeutics for the treatment of diseases and conditions of the CNS and PNS, are known in the art.

In some embodiments, the delivery or targeting of a compound of Formula I or composition thereof, may be to a specific site, thus enhancing the efficacy and reducing the side effects of the compound or composition. As a non-limiting example the specific site may be the dentate gyms or the subventricular zone of the hippocampus using known methods for the administration of the compound or composition.

In embodiments to treat subjects and patients, the methods include identifying a patient suffering from one or more disease, disorders, or conditions, or a symptom thereof, and administering to the subject or patient at least one compound of Formula I or composition as described herein. The identification of a subject or patient as having one or more disease, disorder or condition, or a symptom thereof, may be made by a skilled practitioner using any appropriate means known in the field.

In further embodiments, the methods may be used to treat a cell, tissue, or subject which is exhibiting decreased neurogenesis or increased neurodegeneration. In some cases, the cell, tissue, or subject is, or has been, subjected to, or contacted with, an agent that decreases or inhibits neurogenesis. One non-limiting example is a human subject that has been administered morphine or other agent which decreases or inhibits neurogenesis. Non-limiting examples of other agents include opiates and opioid receptor agonists, such as mu receptor subtype agonists, that inhibit or decrease neurogenesis.

In additional embodiments, the methods may be used to treat subjects having, or diagnosed with, depression or other withdrawal symptoms from morphine or other agents which decrease or inhibit neurogenesis. This is distinct from the treatment of subjects having, or diagnosed with, depression independent of an opiate, such as that of a psychiatric nature, as disclosed herein. In further embodiments, the methods may be used to treat a subject with one or more chemical addiction or dependency, such as with morphine or other opiates, where the addiction or dependency is ameliorated or alleviated by an increase in neurogenesis.

In a preferred embodiment the compound for Formula I or a composition thereof may be used to treat a subject or patient with treatment resistant depression (TRD). The subject or patient may demonstrate little or no improvement under standard care with antidepressant therapy.

In some embodiments, such as those for treating depression and other neurological diseases and conditions, the methods may optionally further comprise use of one or more agents reported as anti-depressant agents. Thus, a method may include treatment with a compound and one or more reported anti-depressant agents as known to the skilled person. Non-limiting examples of such agents include an SSRI (selective serotonin reuptake inhibitor), such as fluoxetine (Prozac®), citalopram (Celexa), escitalopram (Lexapro), fluvoxamine or fluvoxamine maleate (CAS RN: 61718-82-9) and Luvox®, paroxetine (Paxil®), or sertraline (Zoloft®); the compound nefazodone (Serozone®); a selective norepinephrine reuptake inhibitor (SNRI) such as reboxetine (Edronax®) or atomoxetine (Strattera®); a selective serotonin & norepinephrine reuptake inhibitor (SSNRI) such as venlafaxine (Effexor), and its reported metabolite desvenlafaxine, or duloxetine (Cymbalta); a serotonin, noradrenaline, and dopamine "triple uptake inhibitor", such as DOV 102,677 (see Popik et al. "Pharmacological Profile of the "Triple" Monoamine Neurotransmitter Uptake Inhibitor, DOV 102,677." *Cell Mol Neurobiol.* 2006 Apr. 25; Epub ahead of print), DOV 216,303 (see Beer et al. "DOV 216,303, a "triple" reuptake inhibitor: safety, tolerability, and pharmacokinetic profile." *J Clin Pharmacol.* 2004 44(12):1360-7), DOV 21,947 ((+)-1-(3,4-dichlorophenyl)-3-azabicyclo-(3.1.0)hexane hydrochloride), see Skolnick et al. "Antidepressant-like actions of DOV 21,947: a "triple" reuptake inhibitor." *Eur J Pharmacol.* 2003 461(2-3):99-104), NS-2330 or tesofensine (CAS RN 402856-42-2), or NS 2359 (CAS RN 843660-54-8); and agents like dehydroepiandrosterone (DHEA), and DHEA sulfate (DHEAS), CP-122,721 (CAS RN 145742-28-5).

Additional non-limiting examples of such agents include a tricyclic compound such as amitriptyline, desipramine, doxepin, imipramine, or nortriptyline; a psychostimulant such as dextroamphetamine and methylphenidate; an MAO inhibitor such as selegiline (Emsam®); an ampakine such as CX516 (or Ampalex, CAS RN: 154235-83-3), CX546 (or 1-(1,4-benzodioxan-6-ylcarbonyl)piperidine), and CX614 (CAS RN 191744-13-5) from Cortex Pharmaceuticals; a V1b antagonist such as SSR149415 ((2S,4R)-1-[5-Chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2- pyrrolidine carboxamide); a melatonin receptor agonist such as melatonin, agomelatin, tasmelatonin, TIK-301 or BCI-952.

Additional agents capable of being used in combination with the compounds of the present invention include muscarinic/acetylcholine receptor modulators, PDE inhibitors, angiotensin modulators, GABA receptor modulators, 5HT receptor modulators, PPAR modulators including the secondary agents referenced in U.S. Publication Nos. 2007/0049576, 2007/0208029, 2007/0112017, 2007/0270449, 2008/0167291 and 2008/0103165.

Methods of Making Compounds

According to Scheme 1, compounds of Formula I,

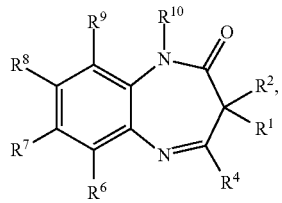

or Formula XII, in which $R^{10}$=H are described below and can be prepared from compounds of Formula V via the following reaction scheme:

can be alternatively used in place of the BOC group. Reduction of the nitro group of compound VI with a metal such as zinc or stannous chloride, containing an aqueous acid such as ammonium chloride or hydrogen chloride, in an organic solvent such as ethanol, at temperatures between 20° C. and 100° C., produces compound VII. Alternative methods of reduction of the nitro group using hydrogen gas in the presence of a suitable catalyst like Raney Nickel or palladium on carbon can be utilized. Treatment of a pyridazine of formula VIII with the anion of IX resulting from the reaction of a base such as LDA, and compound IX in solvent such as THF gives rise to compounds of formula X. When compound X is treated with compound VII in an inert organic solvent such as xylene, or toluene, at elevated temperatures between 80° C. and 160° C. compound XI is formed. The deprotection-cyclization step can be carried out by treatment of compound XI with trifluoracetic acid (TFA) in an inert solvent such as methylene chloride (DCM), to yield compounds of formula XII. The reaction is preferably carried out at temperatures between 0° C. and 50° C.

The synthesis of compound XVII (formula I, $R^{10}$=methyl) can be accomplished by the reactions illustrated in Scheme 2. When compound V is treated with paraformaldehyde and an organic acid for example acetic acid, in an inert solvent such as toluene at elevated temperatures between 80° C. and 160° C., followed by reduction of the intermediate species with a

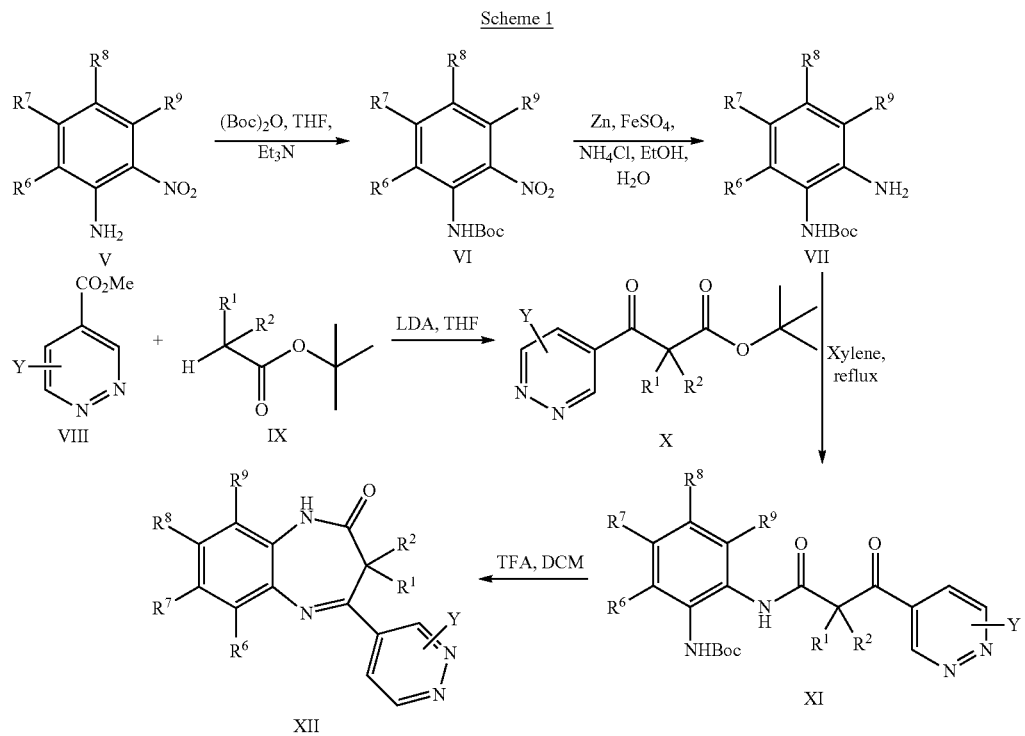

Reaction of compounds of formula V with Di-tert-butyl dicarbonate in a solvent such as THF containing an amine base such as triethylamine, gives rise to compounds of formula VI. Any suitable amino protecting group, such as 9-fluorenylmethoxycarbonyl (FMOC) or benzyloxycarbonyl (Z), reducing agent such as sodium borohydride in an organic solvent such as methanol, compound XIII is produced. Following the procedures described above in Scheme 1, compound XIII can be elaborated to the N-methyl-dihydrobenzo[b][1,4]diazepin-2-one compound XVII.

Scheme 2

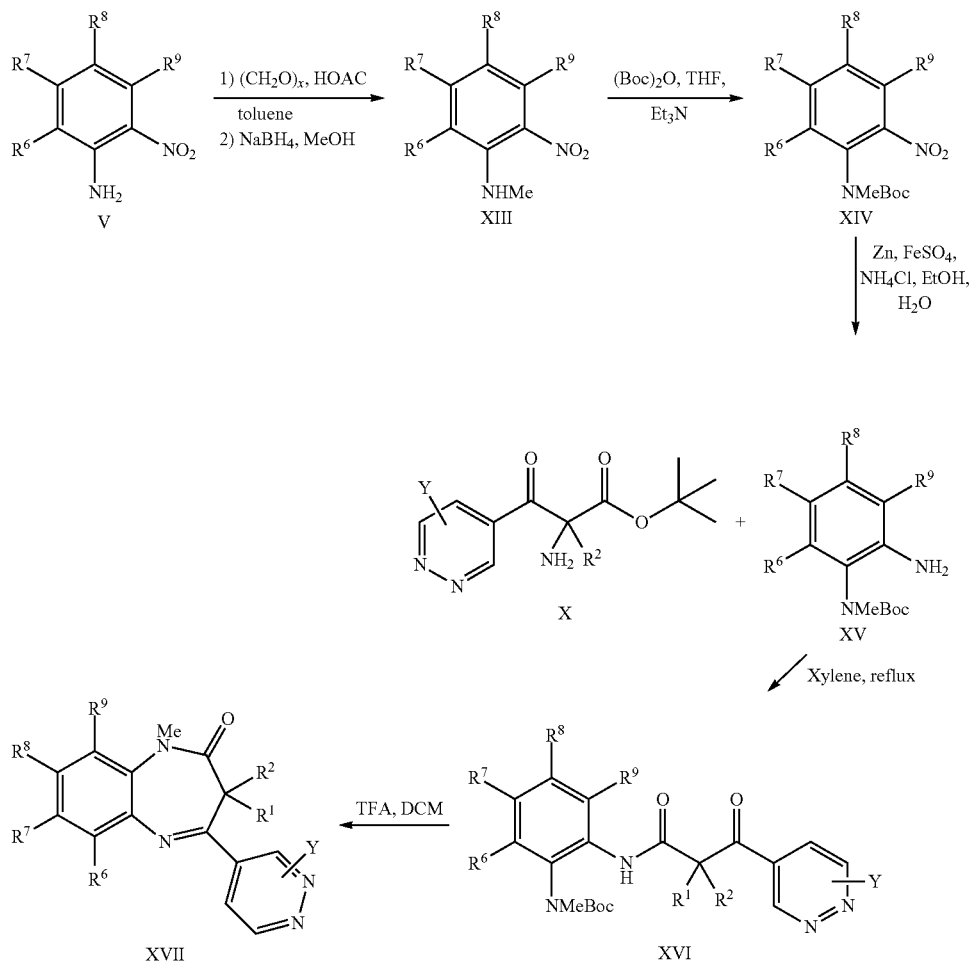

An alternative method of synthesis of compound XVII is illustrated in Scheme 3. When compound XVIII is treated with an organic base such as potassium tert-butoxide in an organic solvent such as THF followed by treatment with $R^{10}$—I (where $R^{10}$ cannot be hydrogen), gives rise to compound XIX. (European Patent Application 0 487 155 A1).

Subsequently additional substituents can be introduced at C-3 position by the treatment of compound XIX with potassium tert-butoxide in an organic solvent such as THF followed by treatment with $R^1$—I (where $R^1$ cannot be hydrogen). Compound XXI is formed when compound XX is treated with potassium tert-butoxide in an organic solvent such as DMF followed by treatment with $R^2$—I (where $R^2$ cannot be hydrogen).

Scheme 3

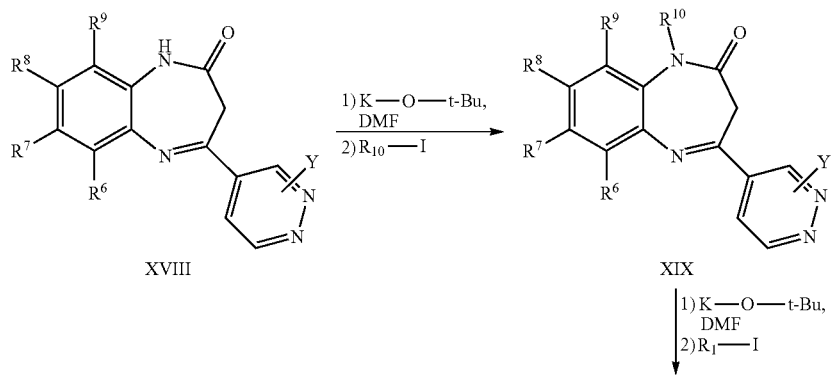

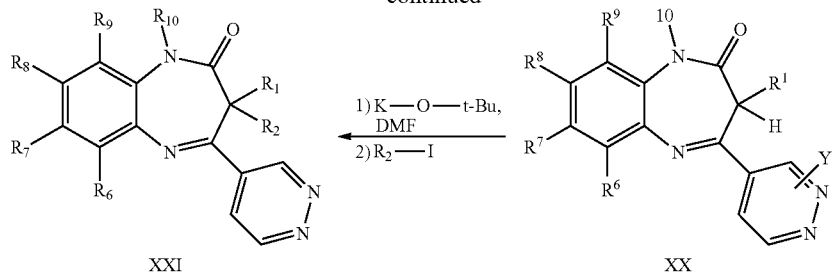

In Scheme 4 and Scheme 5, palladium-mediated coupling reactions are illustrated. Compound XXII is treated with a palladium reagent, for example tetrakis-triphenyl phosphine palladium (O) and a boronic acid (or other suitable coupling partner such as an alkyne, or a tin reagent) in the presence of a base, such as sodium carbonate and organic solvent/solvents, ethanol and toluene. The reaction is carried out at elevated temperatures between 40° C. and 160° C. Compound XXIII and Compound XXV are prepared according to this method. $R^{15}$ encompasses any boronic acid molecule.

Compounds of type XXVII can be synthesized from compound XXVI using the Buchwald-Hardwig reaction conditions illustrated in Scheme 6. This reaction involves the coupling between an aryl halide or triflate XXVI and any amine, represented by $NHR^{16}R^{17}$, in the presence of a base, for example potassium tert-butoxide, and a palladium catalyst ($ML_n$) for example tris(dibenzylideneacetone)dipalladium (0).

Having now generally described the invention, the same will be more readily understood through reference to the following examples which are provided by way of illustration, and are not intended to be limiting of the present invention, unless specified.

EXAMPLES

General Procedure A

Preparation of the 2-nitro-phenyl carbamic acid tert-butyl esters from 2-nitroanilines.

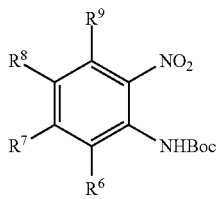

To a solution of the 2-nitroaniline (5.0 g, 23 mmol) and DMAP (0.12 g, 1 mmol) in THF (100 mL) at 0° C., was drop wise added a solution of Li[N(Si(CH$_3$)$_3$)$_2$] (50 mL, 1M in THF) and a solution of Boc$_2$O (6.0 g, 28 mmol) in THF (30 mL). Stirring was continued overnight, until TLC indicated complete conversion. The entire mixture was evaporated to dryness and dried at high vacuum to leave a yellow to dark brown solid. This material was dissolved in dichloromethane (100 mL), poured into sat. NH$_4$Cl solution, extracted with dichloromethane (2×100 mL), washed with brine and dried over MgSO$_4$, removal of the solvent in vacuum left a yellow solid which was adsorbed on silica gel and purified by silica gel column chromatography with hexane/acetone to give the 2-nitro-phenyl-)-carbamic acid tert-butyl ester as a yellow solid.

Example A1

Tert-butyl 4-bromo-2-nitrophenylcarbamate

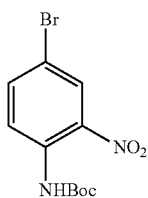

The title compound was prepared from the commercially available 4-bromo-2-nitroaniline [CAS-No. 875-51-4] (5.0 g, 23 mmol) and Boc$_2$O (6.0 g, 28 mmol) according to the general procedure A. Obtained as a yellow solid (5.4 g, 74%), MS (EI) 317 [(M+1)$^+$] and 261 {[(M-C(CH$_3$)$_3$]$^+$}.

Example A2

Tert-butyl 4-trifluoromethyl-2-nitrophenylcarbamate

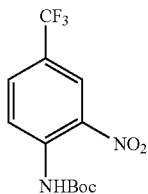

The title compound was prepared from the commercially available 4-trifluoromethyl-2-nitroaniline [CAS-No. 400-98-6] (2.0 g, 10 mmol) and Boc$_2$O (2.5 g, 11 mmol) according to the general procedure A. Obtained as a yellow solid (1.8 g, 60%), MS (EI) 307 [(M+1)$^+$] and 251{[(M-C(CH$_3$)$_3$]$^+$}.

Example A3

Tert-butyl 4-iodo-2-nitrophenylcarbamate

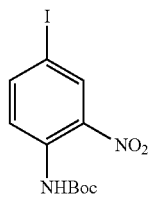

The title compound was prepared from the commercially available 4-iodo-2-nitroaniline [CAS-No. 20691-72-9] (2.0 g, 8 mmol) and Boc$_2$O (2.0 g, 9 mmol) according to the general procedure A. Obtained as a yellow solid (1.5 g, 50%), MS (EI) 365 [(M+1)$^+$] and 309 {[(M-C(CH$_3$)$_3$]$^+$}.

Example A4

Methyl 4-((tert-butoxycarbonyl)amino)-3-nitrobenzoate

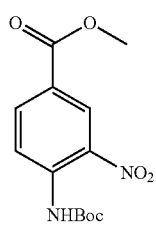 [SMILES: COC(=O)c1ccc(NC(=O)OC(C)(C)C)c([N+](=O)[O-])c1]

The title compound was prepared from the methyl 4-amino-3-nitrobenzoate (prepared by esterification of commercially available 4-amino-3-nitrobenzoic acid [CAS-No. 1588-83-6] (2.4 g, 12 mmol) and Boc$_2$O (3.0 g, 14 mmol) according to the general procedure A. Obtained as a yellow solid (2.5 g, 69%), MS (EI) 300 [(M+1)$^+$] and 227{[(M-C(CH$_3$)$_3$]$^+$}.

Example A5

Tert-butyl 4-chloro-2-nitrophenylcarbamate

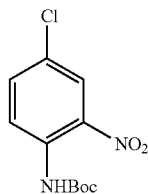

The title compound was prepared from the commercially available 4-chloro-2-nitroaniline [CAS-No. 89-63-4] (2.5 g, 10 mmol) and Boc$_2$O (2.5 g, 12 mmol) according to the general procedure A. Obtained as a yellow solid (2.5 g, 67%), MS (EI) 373 [(M+1)$^+$] and 217 {[(M-C(CH$_3$)$_3$]$^+$}.

Example A6

Tert-butyl 4-Fluoro-2-nitrophenylcarbamate

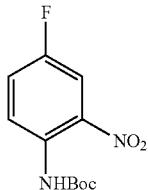

The title compound was prepared from the commercially available 4-fluoro-2-nitroaniline [CAS-No. 364-78-3] (1.8 g, 12 mmol) and Boc$_2$O (3.0 g, 14 mmol) according to the general procedure A. Obtained as a yellow solid (2.2 g, 73%), MS (EI) 257 [(M+1)$^+$] and 200{[(M-C(CH$_3$)$_3$]$^+$}.

Example A7

Tert-butyl 4,5-dimethyl-2-nitrophenylcarbamate

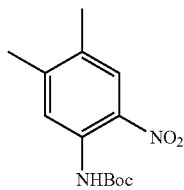

The title compound was prepared from the commercially available 4,5-dimethyl-2-nitroaniline [CAS-No. 6972-71-0] (1.2 g, 7 mmol) and Boc$_2$O (1.9 g, 9 mmol) according to the general procedure A. Obtained as a yellow solid (1.2 g, 63%), MS (EI) 267 [(M+1)$^+$] and 210{[(M-C(CH$_3$)$_3$]$^+$}

General Procedure B

Preparation of the 2-amino-phenyl carbamic acid tert-butyl esters by reduction of 2-nitro-phenyl carbamic acid tert-butyl esters:

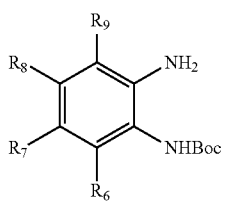

To a mixture of the nitro compound (10 mmol) in ethanol/water (5:1, 60 mL) was added ammonium chloride (80 mmol) and iron sulfate heptahydrate (30 mmol) with efficient stirring. Then zinc metal (30 mmol, 20 mesh) was added to the reaction mixture. The reaction mixture was heated to 50° C. and stirred for an additional 3 hours or overnight until HPLC indicated complete conversion of the starting material. The reaction was then cooled to room temperature and filtered over a pad of Celite with suction. The filter cake was washed with ethanol (70 mL), and the filtrate was concentrated under reduced pressure to give a residue, which—if necessary—can be purified by silica gel column chromatography with hexane/acetone.

Example B1

Tert-butyl 2-amino-4-bromophenylcarbamate

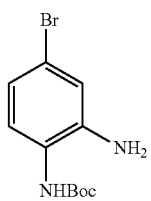 [SMILES: CC(C)(C)OC(=O)Nc1ccc(Br)cc1N]

The title compound was prepared from the tert-butyl 4-bromo-2-nitrophenylcarbamate (Example A1; 3 mmol) by reduction with zinc according to the general procedure B. Obtained as a yellow solid (58%), MS (EI) 287 [(M+1)$^+$].

Example B2

Tert-butyl 2-amino-4-trifluorophenylcarbamate

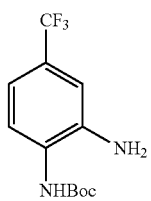 [SMILES: CC(C)(C)OC(=O)Nc1ccc(C(F)(F)F)cc1N]

The title compound was prepared from the tert-butyl 4-trifluoromethyl-2-nitrophenylcarbamate (Example A2; 3 mmol) by reduction with zinc according to the general procedure B. Obtained as a yellow solid (66%), MS (EI) 277 [(M+1)$^+$].

Example B3

Tert-butyl 2-amino-4-iodophenylcarbamate

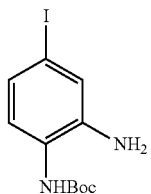 [SMILES: CC(C)(C)OC(=O)Nc1ccc(I)cc1N]

The title compound was prepared from the tert-butyl 4-iodo-2-nitrophenylcarbamate (Example A3; 3 mmol) by reduction with zinc according to the general procedure B. Obtained as a yellow solid (44%), MS (EI) 335 [(M+1)$^+$].

Example B4

Methyl 3-amino-4-((tert-butoxycarbonyl)amino)benzoate

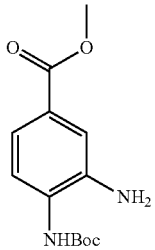

The title compound was prepared from the methyl 3-nitro-4-((tert-butoxycarbonyl)amino)benzoate (Example A4; 3 mmol) by reduction with zinc according to the general procedure B. Obtained as a yellow solid (71%), MS (EI) 267 [(M+1)$^+$].

Example B5

Tert-butyl 2-amino-4-chlorophenylcarbamate

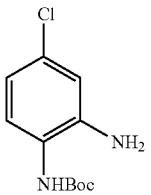

The title compound was prepared from the tert-butyl 4-chloro-2-nitrophenylcarbamate (Example A5; 3 mmol) by reduction with zinc according to the general procedure B. Obtained as a yellow solid (85%), MS (EI) 243 [(M+1)$^+$].

Example B6

Tert-butyl 2-amino-4-fluorophenylcarbamate

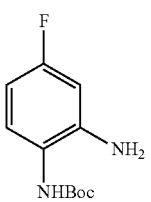

The title compound was prepared from the tert-butyl 4-fluoro-2-nitrophenylcarbamate (Example A6; 3 mmol) by reduction with zinc according to the general procedure B. Obtained as a yellow solid (66%), MS (EI) 227 [(M+1)$^+$].

Example B7

Tert-butyl 2-amino-4,5-dimethylphenylcarbamate

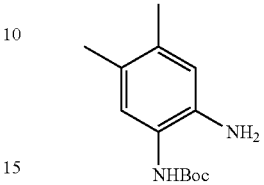

The title compound was prepared from the tert-butyl 4,5-dimethyl-2-nitrophenylcarbamate (Example A7; 3 mmol) by reduction with zinc according to the general procedure B. Obtained as a yellow solid (56%), MS (EI) 237 [(M+1)$^+$].

General Procedure C

Preparation of ethyl or tert-butyl 3-aryl/heteroaryl-3-oxo-propionates:

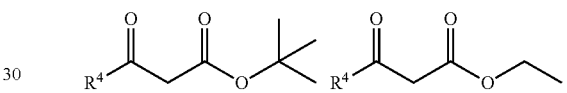

The ethyl or tert-butyl 3-aryl-3-oxo-propionates or ethyl or tert-butyl 3-heteroaryl-3-oxo-propionates were prepared from corresponding methyl or ethyl aryl/heteroaryl esters according to the procedure discussed in *Synthesis* 1985, 45.

Example C1

Tert-butyl 3-oxo-3-(pyridazin-4-yl)propanoate

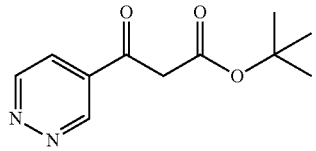 [SMILES: CC(C)(C)OC(=O)CC(=O)c1ccnnc1]

The title compound was prepared from the reaction of 3-pyridazine methyl carboxylate (1 mmol) with the lithium anion of t-butylacetate according to the general procedure C. Obtained as a yellow solid (45%), MS (EI) 223 [(M+1)$^+$].

Example C2

Tert-butyl 3-oxo-3-(pyrimidin-3-yl)propanoate

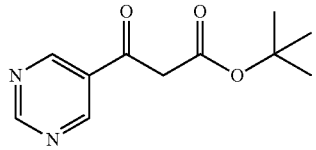 [SMILES: CC(C)(C)OC(=O)CC(=O)c1cncnc1]

The title compound was prepared from the reaction of 3-pyrimidine methyl carboxylate (1 mmol) with the lithium anion of t-butylacetate according to the general procedure C. Obtained as a yellow solid (65%), MS (EI) 223 [(M+1)⁺].

Example C3

Tert-butyl 3-oxo-3-(pyrazin-2-yl)propanoate

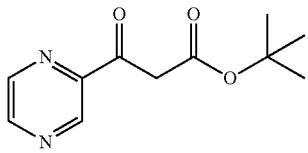 [SMILES: CC(C)(C)OC(=O)CC(=O)c1cnccn1]

The title compound was prepared from the reaction of 2-pyrazine methyl carboxylate (1 mmol) with the lithium anion of t-butylacetate according to the general procedure C. Obtained as a yellow solid (58%), MS (EI) 223 [(M+1)⁺].

Example C4

Tert-butyl 3-oxo-3-(5-methylpyridazin-2-yl)propanoate

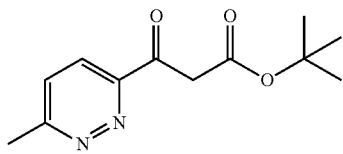 [SMILES: Cc1ccc(C(=O)CC(=O)OC(C)(C)C)nn1]

The title compound was prepared from the reaction of 5-methyl-2-pyridazine methyl carboxylate (1 mmol) with the lithium anion of t-butylacetate according to the general procedure C. Obtained as a yellow solid (55%), MS (EI) 237 [(M+1)⁺].

Example C5

Tert-butyl 3-oxo-3-(5-chloropyridazin-2-yl)propanoate

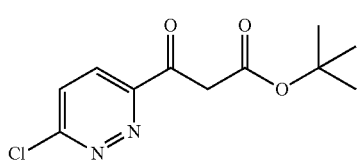 [SMILES: CC(C)(C)OC(=O)CC(=O)c1ccc(Cl)nn1]

The title compound was prepared from the reaction of 5-chloro-2-pyridazine methyl carboxylate (1 mmol) with the lithium anion of t-butylacetate according to the general procedure C. Obtained as a yellow solid (53%), MS (EI) 257 [(M+1)⁺].

Example C6

Tert-butyl 3-oxo-3-(5-hydroxypyridazin-4-yl)propanoate

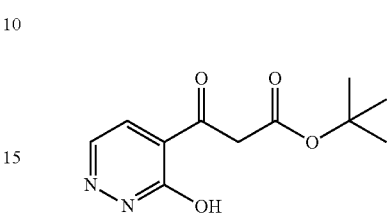

The title compound was prepared from the reaction of 2-hydroxy-3-pyridazine methyl carboxylate (1 mmol) with the lithium anion of t-butylacetate according to the general procedure C. Obtained as a yellow solid (38%), MS (EI) 239 [(M+1)⁺].

Example C7

Methyl 3-(3-cyanophenyl)-3-oxopropanoate

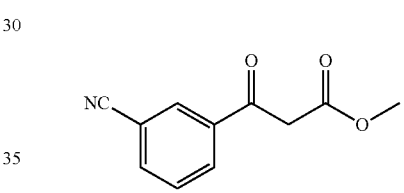

Into a three-necked flask equipped with an argon inlet and a condenser were placed sodium hydride (60%, 689.5 mg, 17.23 mmol), dimethyl carbonate (1.55 g, 17.23 mmol) and 15 mL of toluene. The mixture was stirred under reflux and a solution of 3-acetylbenzonitrile (1.0 g, 6.19 mmol) in toluene (15 mL) was added drop wise. The reaction mixture was stirred at 100° C. for 2 h. The reaction mixture was monitored by LCMS and purified by column chromatography on silica gel eluted with 0-10% of ethyl acetate in petroleum ether to give the product (1.2 g, 86%).

General Procedure D

Preparation of {2-[3-ary-3-oxo-propionylamino-]-phenyl}-carbamic acid tert-butyl esters by reaction of (2-aminophenyl)-carbamic acid tert-butyl esters with ethyl or tert-butyl 3-aryl/heteroaryl-3-oxo-propionates:

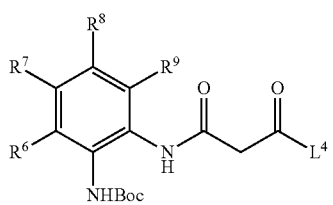

A mixture of the (2-amino-phenyl)-carbamic acid tert-butyl esters (1.0-1.2 mmol) and (1.0-1.5 mmol) of the ethyl or tert-butyl 3-aryl/heteroaryl-3-oxo-propionates was heated in toluene or xylene (4-8 mL) from 90° C. to 150° C., until HPLC indicated complete consumption of the minor component. The solution was allowed to cool to room temperature; the reaction mixture was directly subjected to silica gel column chromatography and eluted with DCM:EtOAc to give the {2-[3-ary-3-oxo-propionylamino-]-phenyl}-carbamic acid tert-butyl esters.

Example D1

Tert-butyl 4-bromo-2-(3-oxo-3-(pyridazin-4-yl)propanamido)phenylcarbamate

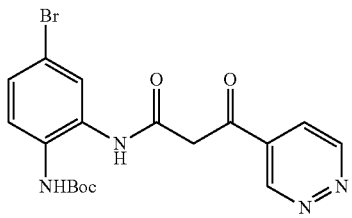 [SMILES: CC(C)(C)OC(=O)Nc1ccc(Br)cc1NC(=O)CC(=O)c1ccnnc1]

The title compound was prepared from the reaction of tert-butyl 2-amino-4-bromophenylcarbamate (Example B1; 1 mmol) and tert-butyl 3-oxo-3-(pyridazin-4-yl)propanoate (Example C1; 1 mmol) according to the general procedure D. Obtained as a yellow solid (89%), MS (EI) 435 [(M+1)$^+$].

Example D2

Tert-butyl 4-trifluoromethyl-2-(3-oxo-3-(pyridazin-4-yl)propanamido)phenylcarbamate

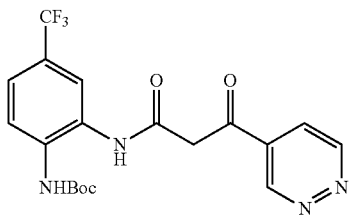 [SMILES: CC(C)(C)OC(=O)Nc1ccc(C(F)(F)F)cc1NC(=O)CC(=O)c1ccnnc1]

The title compound was prepared from the reaction of tert-butyl 2-amino-4-trifluoromethyl phenylcarbamate (Example B2; 1 mmol) and tert-butyl 3-oxo-3-(pyridazin-4-yl) propanoate (Example C1; 1 mmol) according to the general procedure D. Obtained as a yellow solid (85%), MS (EI) 425 [(M+1)$^+$].

Example D3

Tert-butyl 4-iodo-2-(3-oxo-3-(pyridazin-4-yl)propanamido)phenylcarbamate

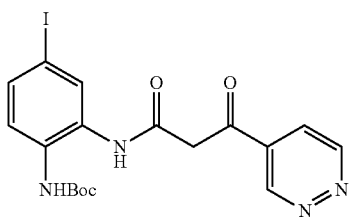 [SMILES: CC(C)(C)OC(=O)Nc1ccc(I)cc1NC(=O)CC(=O)c1ccnnc1]

The title compound was prepared from the reaction of tert-butyl 2-amino-4-iodophenylcarbamate (Example B3; 1 mmol) and tert-butyl 3-oxo-3-(pyridazin-4-yl)propanoate (Example C1; 1 mmol) according to the general procedure D. Obtained as a yellow solid (87%), MS (EI) 483 [(M+1)$^+$].

Example D4

Methyl 4-((tert-butoxycarbonylamino)-3-(3-oxo-3-(pyridazin-4-yl)propanamido)benzoate

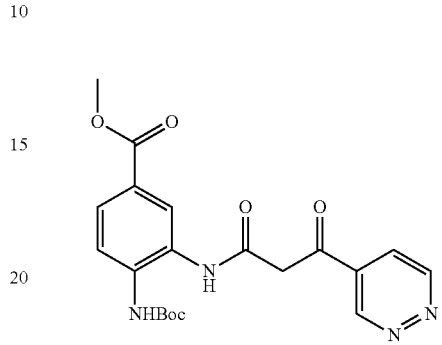

The title compound was prepared from the reaction of Methyl 3-amino-4-((tert-butoxycarbonyl)amino)benzoate (Example B4; 1 mmol) and tert-butyl 3-oxo-3-(pyridazin-4-yl) propanoate (Example C1; 1 mmol) according to the general procedure D. Obtained as a yellow solid (88%), MS (EI) 415 [(M+1)$^+$].

Example D5

Tert-butyl 4-chloro-2-(3-oxo-3-(pyridazin-4-yl)propanamido)phenylcarbamate

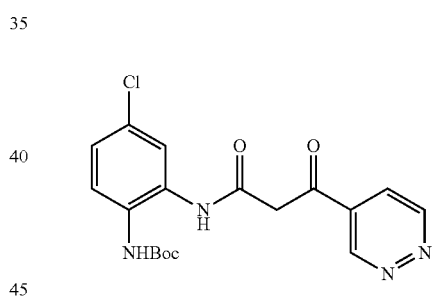

The title compound was prepared from the reaction of tert-butyl 2-amino-4-chlorophenylcarbamate (Example B5; 1 mmol) and tert-butyl 3-oxo-3-(pyridazin-4-yl)propanoate (Example C1; 1 mmol) according to the general procedure D. Obtained as a yellow solid (83%), MS (EI) 391 [(M+1)$^+$].

Example D6

Tert-butyl 4-fluoro-2-(3-oxo-3-(pyridazin-4-yl)propanamido)phenylcarbamate

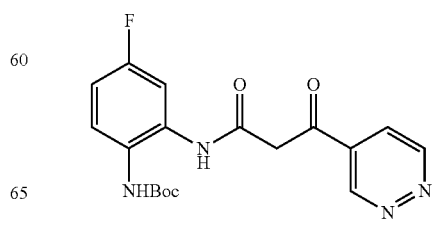

The title compound was prepared from the reaction of tert-butyl 2-amino-4-fluorophenylcarbamate (Example B6; 1 mmol) and tert-butyl 3-oxo-3-(pyridazin-4-yl) propanoate (Example C1; 1 mmol) according to the general procedure D. Obtained as a yellow solid (92%), MS (EI) 375 [(M+1)$^+$].

Example D7

Tert-butyl 4-bromo-2-(3-oxo-3-(pyrimidin-3-yl)propanamido)phenylcarbamate

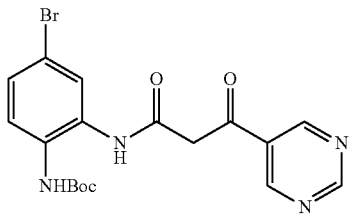 [SMILES: CC(C)(C)OC(=O)Nc1ccc(Br)cc1NC(=O)CC(=O)c1cncnc1]

The title compound was prepared from the reaction of tert-butyl 2-amino-4-bromophenylcarbamate (Example B1; 1 mmol) and tert-butyl 3-oxo-3-(pyrimidin-3-yl) propanoate (Example C2; 1 mmol) according to the general procedure D. Obtained as a yellow solid (84%), MS (EI) 435 [(M+1)$^+$].

Example D8

Tert-butyl 4-bromo-2-(3-oxo-3-(pyrazin-2-yl)propanamido)phenylcarbamate

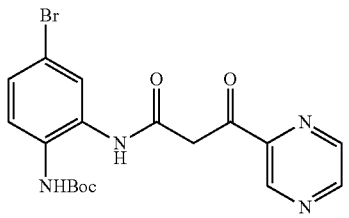 [SMILES: CC(C)(C)OC(=O)Nc1ccc(Br)cc1NC(=O)CC(=O)c1cnccn1]

The title compound was prepared from the reaction of tert-butyl 2-amino-4-bromophenylcarbamate (Example B1; 1 mmol) and tert-butyl 3-oxo-3-(pyrazin-2-yl)propanoate (Example C3; 1 mmol) according to the general procedure D. Obtained as a yellow solid (81%), MS (EI) 435 [(M+1)$^+$].

Example D9

Tert-butyl 4-bromo-2-(3-oxo-3-(5-methylpyridazin-2-yl)propanamido)phenylcarbamate

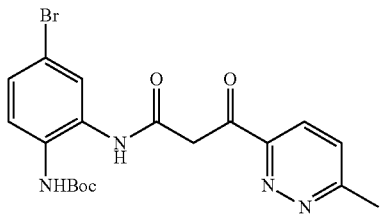 [SMILES: Cc1ccc(C(=O)CC(=O)Nc2cc(Br)ccc2NC(=O)OC(C)(C)C)nn1]

The title compound was prepared from the reaction of tert-butyl 2-amino-4-bromophenylcarbamate (Example B1; 1 mmol) and tert-butyl 3-oxo-3-(5-methylpyridazin-2-yl) propanoate (Example C4; 1 mmol) according to the general procedure D. Obtained as a yellow solid (85%), MS (EI) 449 [(M+1)$^+$].

Example D10

Tert-butyl 4-bromo-2-(3-oxo-3-(5-chloropyridazin-2-yl)propanamido)phenylcarbamate

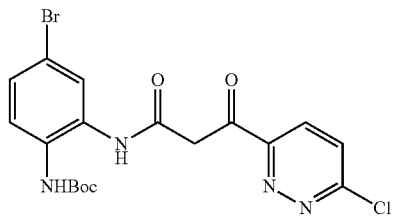 [SMILES: CC(C)(C)OC(=O)Nc1ccc(Br)cc1NC(=O)CC(=O)c1ccc(Cl)nn1]

The title compound was prepared from the reaction of tert-butyl 2-amino-4-bromophenylcarbamate (Example B1)(1 mmol) and tert-butyl 3-oxo-3-(5-chloropyridazin-2-yl) propanoate (Example C1) (1 mmol) according to the general procedure D. Obtained as a yellow solid (76%), MS (EI) 469 [(M+1)$^+$].

Example D11

Tert-butyl 4-bromo-2-(3-oxo-3-(5-hydroxypyridazin-4-yl)propanamido)phenylcarbamate

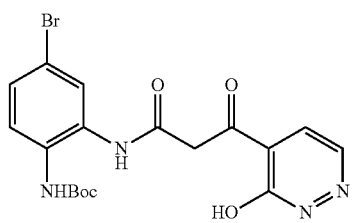 [SMILES: CC(C)(C)OC(=O)Nc1ccc(Br)cc1NC(=O)CC(=O)c1ccnnc1O]

The title compound was prepared from the reaction of tert-butyl 2-amino-4-bromophenylcarbamate (Example B1; 1 mmol) and tert-butyl 3-oxo-3-(5-hydroxypyridazin-4-yl) propanoate (Example C1; 1 mmol) according to the general procedure D. Obtained as a yellow solid (76%), MS (EI) 451 [(M+1)$^+$].

Example D12

4-((tert-butoxycarbonyl)amino)-3-(3-oxo-3-(pyridazin-4-yl) propanamido)benzoic acid

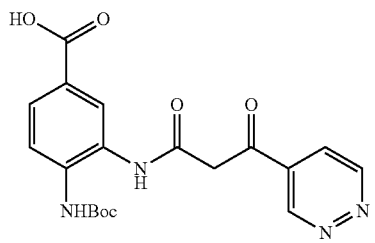 [SMILES: CC(C)(C)OC(=O)Nc1ccc(C(=O)O)cc1NC(=O)CC(=O)c1ccnnc1]

The title compound was prepared from the saponification of methyl 4-((tert-butoxycarbonyl)amino)-3-(3-oxo-3-(pyridazin-4-yl)propanamido)benzoate (Example D4; 1 mmol). Obtained as a yellow solid (100%), MS (EI) 401 [(M+1)⁺].

Example D13

Tert-butyl 4,5-dimethyl-2-(3-oxo-3-(pyridazin-4-yl)propanamido)phenylcarbamate

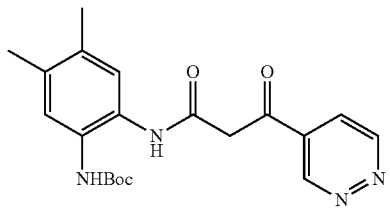 [SMILES: Cc1cc(NC(=O)CC(=O)c2ccnnc2)c(NC(=O)OC(C)(C)C)cc1C]

The title compound was prepared from the reaction of tert-butyl 2-amino-4,5-dimethylphenyl-carbamate (Example B7; 1 mmol) and tert-butyl 3-oxo-3-(pyridazin-4-yl) propanoate (Example C1; 1 mmol) according to the general procedure D. Obtained as a yellow solid (72%), MS (EI) 385 [(M+1)⁺].

Example D14

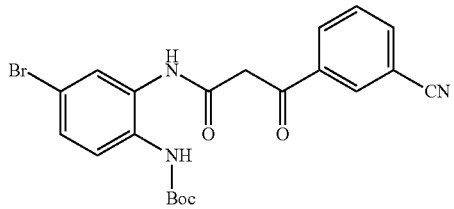 [SMILES: CC(C)(C)OC(=O)Nc1ccc(Br)cc1NC(=O)CC(=O)c1cccc(C#N)c1]

A mixture of compound B1 (3.83 g, 13.3 mmol) and compound C7 (2.98 g, 14.63 mmol) in toluene (60 mL) was stirred at 120° C. for 2 days. After cooling to room temperature, the mixture was filtered to give the solid product (4.0 g, 65%).

General Procedure E

Preparation of 4-(pyridazin-4-yl)-benzo[β][1,4]diazepin-2(3H)-ones:

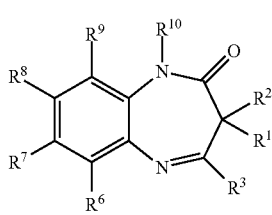

A solution of the {2-[3-ary-3-oxo-propionylamino-]-phenyl}-carbamic acid tert-butyl esters (1.0 mmol) in dichloromethane (5 mL) was treated with TFA (1-5 mL) at room temperature and stiffing was continued until HPLC indicated complete consumption of the starting material. The solvent was removed in vacuum; the residue was purified by preparative HPLC C18 (MeOH:H₂O containing 0.05% formic acid) to give the title compound.

Example E1

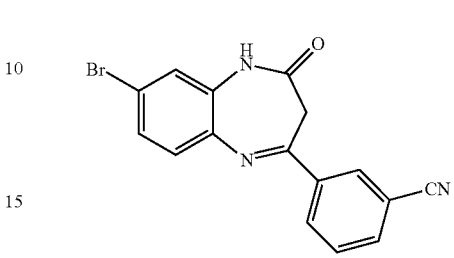

To a solution of compound D14 (300 mg, 0.65 mmol) in DCM (10 mL) was added TFA (3 mL). The reaction mixture was stirred at room temperature for 1 h. The solvent was removed and the residue was washed with MeOH (20 mL×2) to give the product (200 mg, 90%).

Example 1

8-bromo-4-(pyridazin-4-yl)-1H-benzo[β][1,4]diazepin-2(3H)-one (Compound 1)

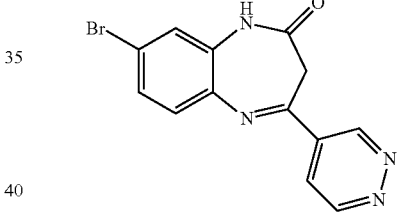

The title compound was prepared from tert-butyl 4-bromo-2-(3-oxo-3-(pyridazin-4-yl) propanamido)phenylcarbamate (Example D1; 1 mmol) according to the general procedure E. Obtained as a yellow solid (100%), MS (EI) 317 [(M+1)⁺].

Example 2

8-trifluoromethyl-4-(pyridazin-4-yl)-1H-benzo[b][1,4]diazepin-2(3H)-one (Compound 2)

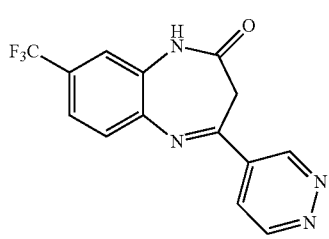 [SMILES: O=C1CC(c2ccnnc2)=Nc2ccc(C(F)(F)F)cc2N1]

The title compound was prepared from tert-butyl 4-trifluoromethyl-2-(3-oxo-3-(pyridazin-4-yl)propanamido)phenylcarbamate (Example D2; 1 mmol) according to the general procedure E. Obtained as a yellow solid (100%), MS (EI) 307 [(M+1)⁺].

Example 3

8-iodo-4-(pyridazin-4-yl)-1H-benzo[b][1,4]diazepin-2(3H)-one (Compound 3)

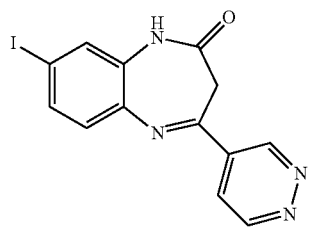 [SMILES: O=C1CC(c2ccnnc2)=Nc2ccc(I)cc2N1]

The title compound was prepared from tert-butyl 4-iodo-2-(3-oxo-3-(pyridazin-4-yl) propanamido)phenylcarbamate (Example D3; 1 mmol) according to the general procedure E. Obtained as a yellow solid (100%), MS (EI) 365 [(M+1)⁺].

Example 4

Methyl 2-oxo-4-(pyridazin-4-yl)-2,3-dihydro-1H-benzo[b][1,4]diazepine-8-carboxylate (Compound 4)

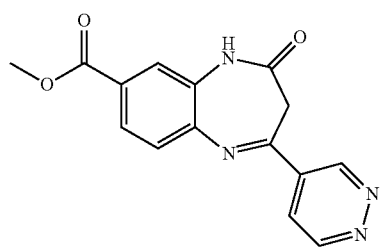 [SMILES: COC(=O)c1ccc2c(c1)NC(=O)CC(c1ccnnc1)=N2]

The title compound was prepared from methyl 4-((tert-butoxycarbonyl)amino)-3-(3-oxo-3-(pyridazin-4-yl)propanamido)benzoate (Example D4; 1 mmol) according to the general procedure E. Obtained as a yellow solid (100%), MS (EI) 297 [(M+1)⁺].

Example 5

8-chloro-4-(pyridazin-4-yl)-1H-benzo[b][1,4]diazepin-2(3H)-one (Compound 5)

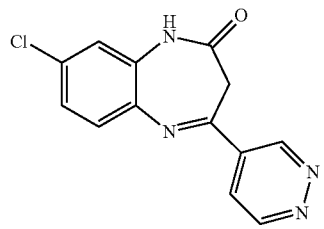 [SMILES: O=C1CC(c2ccnnc2)=Nc2ccc(Cl)cc2N1]

The title compound was prepared from tert-butyl 4-chloro-2-(3-oxo-3-(pyridazin-4-yl) propanamido)phenylcarbamate (Example D5; 1 mmol) according to the general procedure E. Obtained as a yellow solid (100%), MS (EI) 273 [(M+1)⁺].

Example 6

8-fluoro-4-(pyridazin-4-yl)-1H-benzo[b][1,4]diazepin-2(3H)-one (Compound 6)

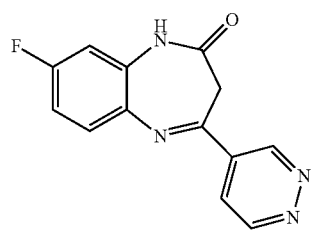 [SMILES: O=C1CC(c2ccnnc2)=Nc2ccc(F)cc2N1]

The title compound was prepared from tert-butyl 4-fluoro-2-(3-oxo-3-(pyridazin-4-yl) propanamido)phenylcarbamate (Example D6; 1 mmol) according to the general procedure E. Obtained as a yellow solid (100%), MS (EI) 257 [(M+1)⁺].

Example 7

8-Bromo-4-(pyrimidin-3-yl)-1H-benzo[b][1,4]diazepin-2(3H)-one (Compound 7)

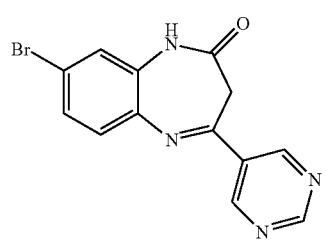 [SMILES: O=C1CC(c2cncnc2)=Nc2ccc(Br)cc2N1]

The title compound was prepared from tert-butyl 4-bromo-2-(3-oxo-3-(pyrimidin-3-yl) propanamido)phenylcarbamate (Example D7; 1 mmol) according to the general procedure E. Obtained as a yellow solid (100%), MS (EI) 317 [(M+1)⁺].

Example 8

8-Bromo-4-(pyrazin-2-yl)-1H-benzo[b][1,4]diazepin-2(3H)-one (Compound 8)

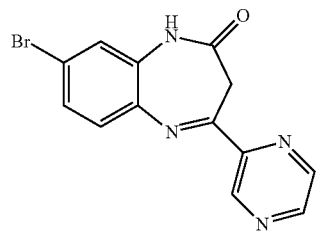 [SMILES: O=C1CC(c2cnccn2)=Nc2ccc(Br)cc2N1]

The title compound was prepared from tert-butyl 4-bromo-2-(3-oxo-3-(pyrazin-2-yl) propanamido)phenylcarbamate (Example D8; 1 mmol) according to the general procedure E. Obtained as a yellow solid (100%), MS (EI) 317 [(M+1)$^+$].

Example 9

8-bromo-4-(5-methylpyridazin-2-yl)-1H-benzo[b][1,4]diazepin-2(3H)-one (Compound 9)

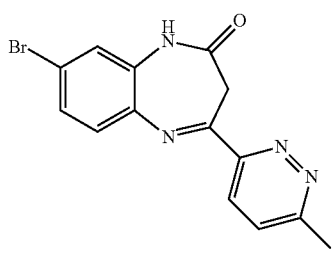 [SMILES: Cc1ccc(C2=Nc3ccc(Br)cc3NC(=O)C2)nn1]

The title compound was prepared from tert-butyl 4-bromo-2-(3-oxo-3-(5-methylpyridazin-2-yl)propanamido)phenyl-carbamate (Example D9; 1 mmol) according to the general procedure E. Obtained as a yellow solid (100%), MS (EI) 331 [(M+1)$^+$].

Example 10

8-bromo-4-(5-chloropyridazin-2-yl)-1H-benzo[b][1,4]diazepin-2(3H)-one (Compound 10)

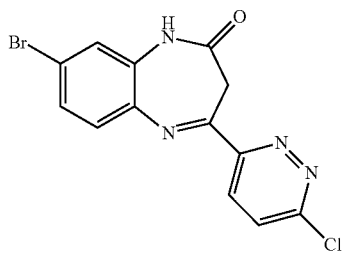 [SMILES: O=C1CC(c2ccc(Cl)nn2)=Nc2ccc(Br)cc2N1]

The title compound was prepared from tert-butyl 4-bromo-2-(3-oxo-3-(5-chloropyridazin-2-yl)propanamido)phenyl-carbamate (Example D10; 1 mmol) according to the general procedure E. Obtained as a yellow solid (100%), MS (EI) 351 [(M+1)$^+$].

Example 11

8-bromo-4-(5-hydroxypyridazin-4-yl)-1H-benzo[b][1,4]diazepin-2(3H)-one (Compound 11)

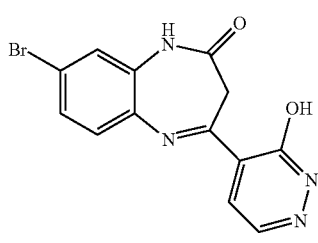 [SMILES: O=C1CC(c2ccnnc2O)=Nc2ccc(Br)cc2N1]

The title compound was prepared from tert-butyl 4-bromo-2-(3-oxo-3-(5-hydroxypyridazin-4-yl)propanamido)phenyl-carbamate (Example D11; 1 mmol) according to the general procedure E. Obtained as a yellow solid (100%), MS (EI) 333 [(M+1)$^+$].

Example 12

2-oxo-4-(pyridazin-4-yl)-2,3-dihydro-1H-benzo[b][1,4]diazepine-8-carboxylic acid (Compound 12)

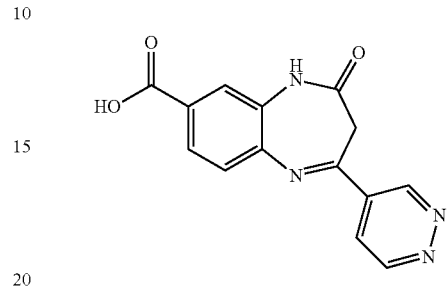

The title compound was prepared from 4-((tert-butoxycar-bonyl)amino)-3-(3-oxo-3-(pyridazin-4-yl)propanamido) benzoic acid (Example D12; 1 mmol) according to the general procedure E. Obtained as a yellow solid (100%), MS (EI) 283 [(M+1)$^+$].

Example 13

8,9-Dimethyl-4-(pyridazin-4-yl)-1H-benzo[b][1,4]diazepin-2(3H)-one (Compound 13)

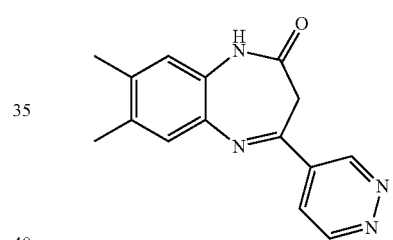

The title compound was prepared from tert-butyl 4,5-dim-ethyl-2-(3-oxo-3-(pyridazin-4-yl)propanamido)phenylcar-bamate (Example D13; 1 mmol) according to the general procedure E. Obtained as a yellow solid (100%), MS (EI) 267 [(M+1)$^+$].

General Procedure F

Preparation of 1-methyl-4-(pyridazin-4yl)-benzo[b][1,4]diazepin-2-ones or 1,3-dimethyl-4-(pyridazin-4yl)-benzo[b][1,4]diazepin-2-ones:

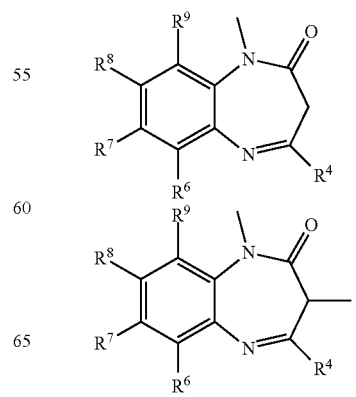

To a solution of the {2-[3-ary-3-oxo-propionylamino-]-phenyl}-carbamic acid tert-butyl esters (10 mmol) in anhydrous THF (50 mL) was added powered potassium t-butoxide (12 mmol). The resulting mixture was stirred at room temperature for 10 min. Methyl iodide (12 mmol) was added and the resulting colorless solution was stirred at room temperature for 45 min. The mixture was diluted with saturated ammonium chloride solution (20 mL) and extracted with dichloromethane (2×50 mL). The organic extracts were dried over MgSO₄, filtered, and concentrated. Chromatography of the resulting oil/solid on silica gel gave the 1-methyl-4-(pyridazin-4yl)-benzo[b][1,4]diazepin-2-ones or 1,3-dimethyl-4-(pyridazin-4yl)-benzo[b][1,4]diazepin-2-ones.

Example 14

8-bromo-4-(pyridazin-4-yl)-1H-benzo[b][1,4]diazepin-2(3H)-one (Compound 14)

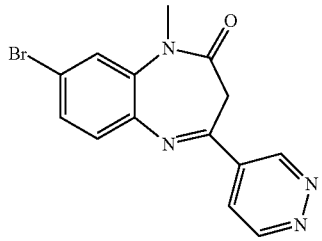 [SMILES: CN1C(=O)CC(c2ccnnc2)=Nc2ccc(Br)cc21]

General Procedure G

Preparation of (4-aryl-2-nitro-phenyl)-carbamic acid tert-butyl esters or 8-aryl-4-(pyridazin-4yl)-1H-benzo[b][1,4]diazepin-2(3H)-one by direct Suzuki-coupling of (4-bromo or iodo-2-nitro-phenyl)-carbamic acid tert-butyl esters or 8-bromol-4-(pyridazin-4yl)-1H-benzo[b][1,4]diazepin-2(3H)-one:

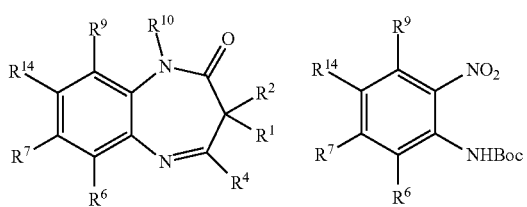

A mixture of the 4-bromo or iodo-2-nitro-phenyl)-carbamic acid tert-butyl esters or 8-bromol-4-(pyridazin-4yl)-1H-benzo[b][1,4]diazepin-2(3H)-one (3.0 mmol), the aryl/heteroarylboronic acid (4.5 mmol) and (Ph₃P)₄Pd (3 mol %) in toluene/sat. Na₂CO₃ solution (1:1, 50 mL) was stirred at 90° C. overnight under nitrogen atmosphere until HPLC indicated complete conversion of the bromide or iodide. The mixture was transferred into a separating funnel, water (20 mL) was added and the product was extracted with dichloromethane (2×50 mL). The combined organic layers were washed with brine (50 mL) and dried over MgSO₄. Removal of the solvent left a yellow brown residue, which was purified by silica gel column chromatography with hexane/acetone or preparative HPLC C18 (MeOH:H₂O containing 0.05% formic acid) to give the title compound.

Example 15

8-(Thiophen-2-yl)-4-(pyridazin-4-yl)-1H-benzo[b][1,4]diazepin-2(3H)-one (Compound 15)

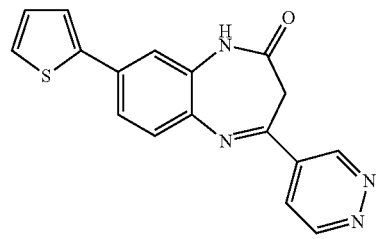 [SMILES: O=C1CC(c2ccnnc2)=Nc2ccc(-c3cccs3)cc2N1]

The title compound was prepared from 8-bromo-4-(pyridazin-4-yl)-1H-benzo[b][1,4]diazepin-2(3H)-one (Example 1; 1 mmol) and commercial available thiophene-2-boronic acid (CAS-No: 6165-68-0)) (1.5 mmol) according to the general procedure G. Obtained as a yellow solid (51%), MS (EI) 321 [(M+1)⁺].

Example 16

8-(2-Fluorophenyl)-4-(pyridazin-4-yl)-1H-benzo[b][1,4]diazepin-2(3H)-one (Compound 16)

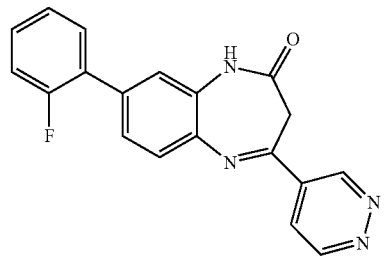 [SMILES: O=C1CC(c2ccnnc2)=Nc2ccc(-c3ccccc3F)cc2N1]

The title compound was prepared from 8-bromo-4-(pyridazin-4-yl)-1H-benzo[b][1,4]diazepin-2(3H)-one (Example 1; 1 mmol) and commercial available 2-fluorophenyl-boronic acid (CAS-No: 1993-03-9; 1.5 mmol) according to the general procedure G. Obtained as a yellow solid (67%), MS (EI) 333 [(M+1)⁺].

Example 17

8-(3,4-Dimethoxyphenyl)-4-(pyridazin-4-yl)-1H-benzo[b][1,4]diazepin-2(3H)-one (Compound 17)

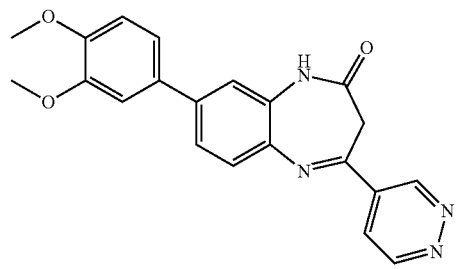 [SMILES: COc1ccc(-c2ccc3c(c2)NC(=O)CC(c2ccnnc2)=N3)cc1OC]

The title compound was prepared from 8-bromo-4-(pyridazin-4-yl)-1H-benzo[b][1,4]diazepin-2(3H)-one (Example 1; 1 mmol) and commercial available 3,4-dimethoxyphenylboronic acid (CAS-No: 122775-35-3; 1.5 mmol) according to the general procedure G. Obtained as a yellow solid (75%), MS (EI) 375 [(M+1)$^+$].

General Procedure H

Preparation of (4-amino-2-nitro-phenyl)-carbamic acid tert-butyl esters or 8-amino-4-(pyridazin-4yl)-1H-benzo[b][1,4]diazepin-2(3H)-one by Buchwald-Hardwig reaction of (4-bromo or iodo-2-nitro-phenyl)-carbamic acid tert-butyl esters or 8-bromo1-4-(pyridazin-4yl)-1H-benzo[b][1,4]diazepin-2(3H)-one:

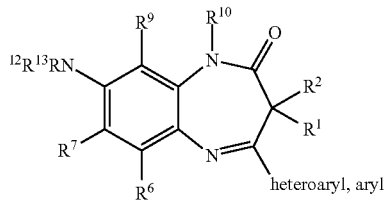

To a solution of the 4-bromo or iodo-2-nitro-phenyl)-carbamic acid tert-butyl esters or 8-bromo1-4-(pyridazin-4yl)-1H-benzo[b][1,4]diazepin-2(3H)-one (3.0 mmol) and the substituted amine (4.5 mmol) in toluene (50 mL) was added sodium tert-butoxide (4.5 mmol), (±)BNAP (5 mol %) and Pd2(dba)3 (10 mol %). The resulting mixture was stirred at 90° C. overnight under nitrogen atmosphere until HPLC indicated complete conversion of the bromide or iodide. The mixture was transferred into a separating funnel, water (20 mL) was added and the product was extracted with dichloromethane (2×50 mL). The combined organic layers were washed with brine (50 mL) and dried over MgSO$_4$. Removal of the solvent left a yellow brown residue, which was purified by silica gel column chromatography with hexane/acetone or by preparative HPLC C18 (MeOH:H$_2$O containing 0.05% formic acid) to give the title compound.

Example 18

The compounds showing mass spectrometry data in the following table were prepared.

TABLE 1

| Compound | R$^X$ | R$^Y$ | R$^Z$ | M + H found |
|---|---|---|---|---|
| Compound 18 | 8-cyano | Pyridazin-4-yl | H | 264.04 |
| Compound 19 | 8-benzoyl | Pyridazin-4-yl | H | 343.10 |
| Compound 20 | 8-bromo-6-methyl | Pyridazin-4-yl | H | 331.01 |
| Compound 21 | 8-bromo-7-chloro | Pyridazin-4-yl | H | 350.95 |
| Compound 22 | 8-bromo-6-trifluoromethyl | Pyridazin-4-yl | H | 384.99 |
| Compound 23 | 8-bromo-6-iodo | Pyridazin-4-yl | H | ND |
| Compound 24 | 7,8-dibromo | Pyridazin-4-yl | H | 394.88 |
| Compound 25 | 8-bromo-7-methoxy | Pyridazin-4-yl | H | 347.01 |
| Compound 26 | 8-bromo-7-trifluoromethyl | Pyridazin-4-yl | H | 384.99 |
| Compound 27 | 8-bromo-7-hydroxy | Pyridazin-4-yl | H | 334.99 |
| Compound 28 | 7-bromo | Pyridazin-4-yl | H | 316.98 |
| Compound 29 | 8-bromo-7-methyl | Pyridazin-4-yl | H | 330.96 |
| Compound 30 | 8-phenyl | Pyridazin-4-yl | H | 315.12 |
| Compound 31 | 8-(3,5-difluorophenyl) | Pyridazin-4-yl | H | 351.09 |
| Compound 32 | 8-bromo | 5-Methyl-pyrazin-2-yl | H | 331.14 |
| Compound 33 | 8-bromo | 6-Hydroxy-pyridazin-3-yl | H | 333.01 |
| Compound 34 | 8-bromo | Imidazo[1,2-a]pyridine-3-yl | H | 356.98 |
| Compound 35 | 8-bromo | 2-Oxo-2,3-dihydrobenzo[d]thiazol-6-yl | H | 389.9 |
| Compound 36 | 8-(2-fluorophenylalkynyl) | 2-Oxo-2,3-dihydrobenzo[d]thiazol-6-yl | H | 428.1 |
| Compound 37 | 8-(imidazol-1-yl) | Pyridazin-4-yl | H | ND |
| Compound 38 | 8-bromo-6-fluoro | Pyridazin-4-yl | H | 334.99 |
| Compound 39 | 3,4,5-trifluorophenyl | Pyridazin-4-yl | H | 369.13 |
| Compound 40 | 8-carboxy | 3-cyanophenyl | H | 306.0 |
| Compound 41 | 8-(2-carboxyphenyl) | 3-cyanophenyl | H | 382.1 |
| Compound 42 | 8-methoxycarbonyl | 3-cyanophenyl | H | 319.9 |
| Compound 43 | 8-(4-carboxyphenyl) | 3-cyanophenyl | H | 382.0 |
| Compound 44 | 8-propylcarbamoyl | 3-cyanophenyl | H | 347.1 |
| Compound 45 | 8-benzylcarbamoyl | 3-cyanophenyl | H | 395.1 |
| Compound 46 | 8-(3-carboxyphenyl) | 3-cyanophenyl | H | 382.0 |
| Compound 47 | 8-methylcarbamoyl | 3-cyanophenyl | H | 318.9 |
| Compound 48 | 8-dimethylcarbamoyl | 3-cyanophenyl | H | 332.9 |

TABLE 1-continued

[Structure: benzodiazepinone scaffold with $R^X$ on benzene ring, $R^Z$ on N, and $R^Y$ on the C=N carbon]

| Compound | $R^X$ | $R^Y$ | $R^Z$ | M + H found |
|---|---|---|---|---|
| Compound 49 | 8-(prop-2-yn-1-ylcarbamoyl) | 3-cyanophenyl | H | 342.9 |
| Compound 50 | 8-(3-methoxy-carbonylphenyl) | 3-cyanophenyl | H | 396.1 |
| Compound 51 | 8-(4-methoxy-carbonylphenyl) | 3-cyanophenyl | H | 396.0 |
| Compound 52 | 8-allylcarbamoyl | 3-cyanophenyl | H | 344.9 |
| Compound 53 | 8-(3-methoxy-3-oxoprop-1-en-1-yl) | 3-cyanophenyl | H | 346.1 |
| Compound 54 | 8-carbamoyl | 3-cyanophenyl | H | 304.8 |
| Compound 55 | 8-(2-methoxy-2-oxoethyl)carbamoyl | 3-cyanophenyl | H | 377.0 |
| Compound 56 | 8-((carboxymethyl)carbamoyl) | 3-cyanophenyl | H | 362.8 |
| Compound 57 | 8-methylsulfonyl | 3-cyanophenyl | H | ND |
| Compound 58 | 8-(2-carboxyvinyl) | 3-cyanophenyl | H | 332.0 |
| Compound 59 | 8-amino | 3-cyanophenyl | H | 277.0 |
| Compound 60 | 8-acetamido | 3-cyanophenyl | H | 319.0 |
| Compound 61 | 8-phenylcarbamoyl | 3-cyanophenyl | H | 381.0 |
| Compound 62 | 8-methylsulfonamido | 3-cyanophenyl | H | 354.9 |
| Compound 63 | 8-pivalamido | 3-cyanophenyl | H | 377.0 |
| Compound 65 | 8-carboxy | 2-chloropyridin-4-yl | H | 316.0 |
| Compound 66 | 8-carboxy | 2-cyanopyridin-4-yl | H | 307.0 |
| Compound 67 | 8-propylcarbamoyl | 2-chloropyridin-4-yl | H | 357.0 |
| Compound 68 | 8-propylcarbamoyl | 2-cyanopyridin-4-yl | H | |
| Compound 69 | 8-(prop-2-yn-1-ylcarbamoyl) | 2-chloropyridin-4-yl | H | 352.9 |
| Compound 70 | 8-(prop-2-yn-1-ylcarbamoyl) | 2-cyanopyridin-4-yl | H | |
| Compound 71 | 8-boronic acid | 3-cyanophenyl | H | 305.8 |
| Compound 72 | 8-($H_2N$—C(=NH)—) | 3-cyanophenyl | H | |
| Compound 73 | 8-(AcHN—C(=NH)—) | 3-cyanophenyl | H | |
| Compound 74 | 8-carboxamide | Pyridazin-4-yl | H | |
| Compound 75 | 8-propylcarbamoyl | Pyridazin-4-yl | H | |
| Compound 76 | 8-allylcarbamoyl | Pyridazin-4-yl | H | |
| Compound 77 | 8-N-(methylsulfonyl)carboxamide | Pyridazin-4-yl | H | |
| Compound 78 | 8-carboxy | Pyridazin-4-yl | Me | |
| Compound 79 | 8-(2-carboxyphenyl) | Pyridazin-4-yl | H | |
| Compound 82 | 8-((benzyloxy)carbonyl)amino | 3-bromophenyl | H | 466 |
| Compound 83 | 8-((phenoxy)carbonyl)amino | 3-bromophenyl | H | 450 |
| Compound 84 | 8-((phenoxy)carbonyl)amino | 3-cyanophenyl | H | 397.4 |
| Compound 85 | 8-((benzyloxy)carbonyl)amino | 3-cyanophenyl | H | 411 |
| Compound 86 | 8-((phenoxy)carbonyl)amino | 3-(2,6-dimethylpyridin-4-yl)phenyl | H | 477.2 |
| Compound 87 | 8-((benzyloxy)carbonyl)amino | 3-(phenoxy)phenyl | H | 478.3 |
| Compound 88 | 8-((benzyloxy)carbonyl)amino | 3-(2,6-dimethylpyridin-4-yl)phenyl | H | 491.4 |
| Compound 89 | 8-(3-phenylureido) | 3-bromophenyl | H | 449 |
| Compound 90 | 8-(3-benzylureido) | 3-bromophenyl | H | 463.1 |
| Compound 91 | 8-(3-phenylureido) | 3-(2,6-dimethylpyridin-4-yl)phenyl | H | 476 |
| Compound 92 | 8-(3-benzylureido) | 3-(2,6-dimethylpyridin-4-yl)phenyl | H | 490 |
| Compound 93 | 8-(3-benzylureido) | 3-cyanophenyl | H | 410 |
| Compound 94 | 8-(3-phenylureido) | 3-cyanophenyl | H | 396 |
| Compound 95 | 8-(3-benzyl-2-cyanoguanidino) | 3-cyanophenyl | H | 434.3 |
| Compound 96 | 8-(3-benzyl-2-cyanoguanidino) | 3-bromophenyl | H | |

TABLE 1-continued

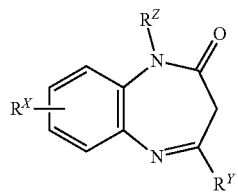

| Compound | $R^X$ | $R^Y$ | $R^Z$ | M + H found |
|---|---|---|---|---|
| Compound 97 | 8-(3-benzyl-2-cyanoguanidino) | 3-(2,6-dimethylpyridin-4-yl)phenyl | H | |
| Compound 98 | 8-(3-benzyl-2-cyanoguanidino) | 2-cyanopyridin-4-yl | H | |
| Compound 99 | 8-(3-benzyl-2-cyanoguanidino) | 2-chloropyridin-4-yl | H | |
| Compound 100 | 8-(3-phenyl-2-cyanoguanidino) | 3-cyanophenyl | H | |
| Compound 101 | 8-(3-phenyl-2-cyanoguanidino) | 3-bromophenyl | H | |
| Compound 102 | 8-(3-phenyl-2-cyanoguanidino) | 3-(2,6-dimethylpyridin-4-yl)phenyl | H | |
| Compound 103 | 8-(3-phenyl-2-cyanoguanidino) | 2-cyanopyridin-4-yl | H | |
| Compound 104 | 8-(3-phenyl-2-cyanoguanidino) | 2-chloropyridin-4-yl | H | |
| Compound 105 | 8-((1-(benzylamino)-2-nitrovinyl)amino | 3-cyanophenyl | H | |
| Compound 106 | 8-((1-(benzylamino)-2-nitrovinyl)amino | 3-bromophenyl | H | |
| Compound 107 | 8-((1-(benzylamino)-2-nitrovinyl)amino | 3-(2,6-dimethylpyridin-4-yl)phenyl | H | |
| Compound 108 | 8-((1-(benzylamino)-2-nitrovinyl)amino | 2-cyanopyridin-4-yl | H | |
| Compound 109 | 8-((1-(benzylamino)-2-nitrovinyl)amino | 2-chloropyridin-4-yl | H | |

Also 8-bromo-4-(pyridazin-4-yl)-4,5-dihydro-1H-benzo[b][1,4]diazepin-2(3H)-one [M+H]$^+$=318.99 (Compound 64); and 2-(3-cyanophenyl)-4-oxo-2,3,4,5-tetrahydro-1H-benzo[b][1,4]diazepine-7-carboxylic acid [M+H]$^+$=308.1 (Compound 81).

Example 19
Synthesis of benzyl(4-(3-bromophenyl)-2-oxo-2,3-dihydro-1H-benzo[b][1,4]diazepin-8-yl)carbamate (Compound 82)

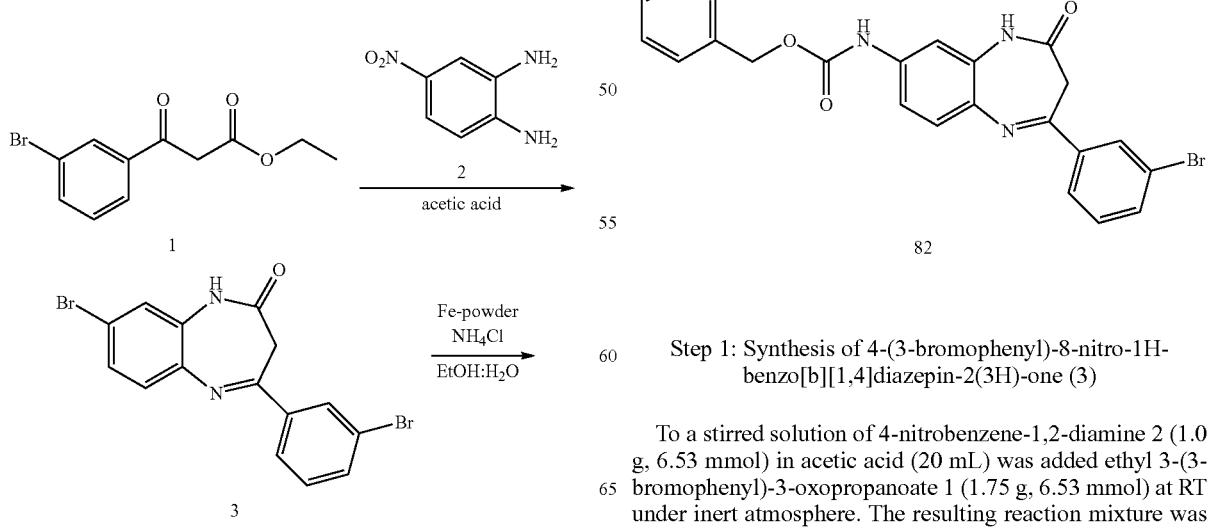

Step 1: Synthesis of 4-(3-bromophenyl)-8-nitro-1H-benzo[b][1,4]diazepin-2(3H)-one (3)

To a stirred solution of 4-nitrobenzene-1,2-diamine 2 (1.0 g, 6.53 mmol) in acetic acid (20 mL) was added ethyl 3-(3-bromophenyl)-3-oxopropanoate 1 (1.75 g, 6.53 mmol) at RT under inert atmosphere. The resulting reaction mixture was heated to 110° C. and stirred for 12 h. After complete consumption of the starting material (by TLC), the reaction mixture was cooled to RT and diluted with water (100 mL) and extracted with EtOAc (3×50 mL). The combined organic extracts were dried over anhydrous Na$_2$SO$_4$ and concentrated under reduced pressure and the obtained crude was purified by silica gel column chromatography (eluent: 25% EtOAc/Hexane) to afford compound 3 (0.91 g, 39.5%) as yellow solid. $^1$H NMR (500 MHz, DMSO-d$_6$): δ 10.91 (bs, 1H), 8.25 (s, 1H), 8.09-8.01 (m, 3H), 7.82 (d, J=6.4 Hz, 1H), 7.68 (d, J=7.6 Hz, 1H), 7.57-7.48 (m, 1H), 3.67 (s, 2H). MS (ESI): 361 [M+1]$^+$ Step 2: Synthesis of 8-amino-4-(3-bromophenyl)-1H-benzo[b][1,4]diazepin-2(3H)-one (4)

To a stirred solution of compound 3 (0.1 g, 0.27 mmol) in EtOH:H$_2$O (10 mL, 6:3) was added Fe-powder (0.076 g, 1.39 mmol) followed by NH$_4$Cl (0.037 g, 0.70 mmol) at RT. The resulting reaction mixture was heated to 90° C. and stirred for 1 h; progress of the reaction was monitored by TLC. The reaction mixture was then cooled to RT; the reaction mixture was filtered and the obtained filtrate was concentrated under reduced pressure. The residue was diluted with water (10 mL) and then extracted with EtOAc (2×10 mL). The combined organic extracts were dried over anhydrous Na$_2$SO$_4$ and concentrated under reduced pressure to afford 4 (35 mg, 38%) as yellow solid. $^1$H NMR (400 MHz, DMSO-d$_6$): δ 10.32 (bs, 1H), 8.15-8.13 (m, 1H), 7.97 (d, J=7.6 Hz, 1H), 7.69 (d, J=7.2 Hz, 1H), 7.48 (d, J=7.6 Hz, 1H), 7.12 (d, J=8.8 Hz, 1H), 6.52 (d, J=8.4 Hz, 1H), 6.32 (s, 1H), 5.48 (bs, 2H), 3.42 (s, 2H). Mass: m/z 331 [M+1]$^+$ Step 3: Synthesis of benzyl(4-(3-bromophenyl)-2-oxo-2,3-dihydro-1H-benzo[b][1,4]diazepin-8-yl)carbamate (82)

To a stirred solution of 4 (50 mg, 0.15 mmol) in THF (5 mL) was added Et$_3$N (0.031 mL, 0.22 mmol) followed by benzyl chloroformate (1.06 mL, 0.18 mmol) at 0° C. under inert atmosphere. The resulting reaction mixture was allowed to warm to RT and stirred for 12 h. After consumption of the starting material (by TLC), the reaction mixture was diluted with water and extracted with EtOAc. The combined organic extracts were washed with water, dried over anhydrous Na$_2$SO$_4$ and concentrated under reduced pressure. The obtained crude material was purified by silica gel column chromatography [eluent: 35% EtOAc/hexane] to afford the title compound 82 (15 mg, 21.4%) as an off-white solid. $^1$H NMR (400 MHz, DMSO-d$_6$): δ 10.60 (bs, 1H), 10.00 (bs, 1H), 8.18 (s, 1H), 8.02 (d, J=7.6 Hz, 1H), 7.74 (d, J=7.6 Hz, 1H), 7.51-7.28 (m, 9H), 5.18 (s, 2H), 3.49 (s, 2H). MS (ESI): 466 [M+1]$^+$ Example 20

Synthesis of 1-(4-(3-bromophenyl)-2-oxo-2,3-dihydro-1H-benzo[β][1,4]diazepin-8-yl)-3-phenylurea (Compound 89)

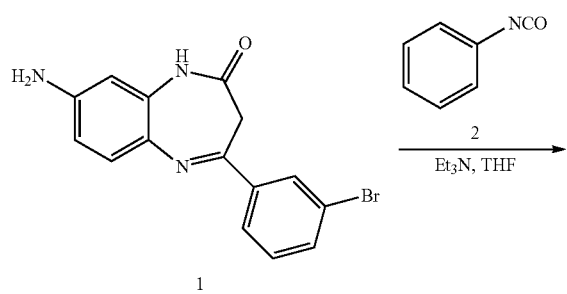

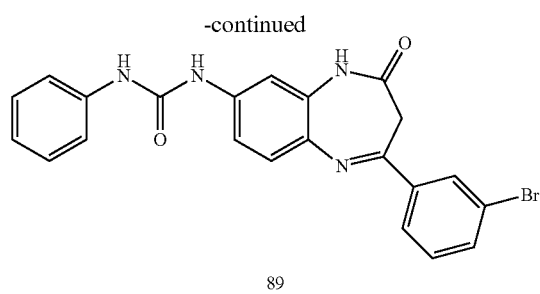

To a stirred solution of compound 1 (Example 19, Step 2; 120 mg, 0.36 mmol) in THF (20 mL) was added Et$_3$N (36.83 mg, 0.36 mmol) followed by phenylisocyanate (2) (43.40 mg, 0.36 mmol) at 0° C. under inert atmosphere. The resulting reaction mixture was allowed warm to RT and stirred for 1 h; progress of the reaction was monitored by TLC. The precipitated solid was filtered and concentrated under reduced pressure to afford the title compound 89 (50 mg, 30.59%) as yellow solid. $^1$H NMR (400 MHz, DMSO-d$_6$): δ 10.58 (bs, 1H), 8.90 (bs, 1H), 8.67 (bs, 1H), 8.19 (s, 1H), 8.18-8.01 (m, 1H), 7.75-7.72 (m, 1H), 7.51-7.00 (m, 8H), 6.96 (t, J=9.0 Hz, 1H), 3.49 (s, 2H). MS (ESI): m/z 449 [M+1]$^+$ Example 21

Synthesis of phenyl(4-(3-bromophenyl)-2-oxo-2,3-dihydro-1H-benzo[b][1,4]diazepin-8-yl)carbamate (Compound 83)

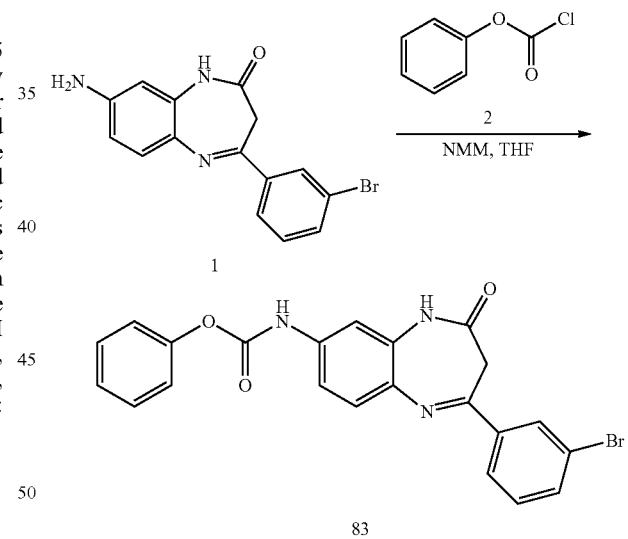

To a stirred solution of compound 1 (Example 19, Step 2; 200 mg, 0.60 mmol) in THF (10 mL) was added NMM (67.53 mg, 0.66 mmol) followed by phenylchloroformate (2) (113.79 mg, 0.72 mmol) at 0° C. under inert atmosphere. The resulting reaction mixture was allowed warm to RT and stirred for 2 h; progress of the reaction was monitored by TLC. The reaction mixture was diluted with water (20 mL) and extracted with EtOAc (3×20 mL). The combined organic extracts were dried over anhydrous Na$_2$SO$_4$ and concentrated under reduced pressure. The crude material was purified by silica gel column chromatography [eluent: 1% MeOH/CH$_2$Cl$_2$] to afford the title compound 83 (150 mg, 55%) as yellow solid. $^1$H NMR (500 MHz, DMSO-d$_6$): δ 10.65 (bs, 1H), 10.45 (bs, 1H), 8.19 (s, 1H), 8.03 (d, J=8.0 Hz, 1H), 7.74

(d, J=7.5 Hz, 1H), 7.50-7.40 (m, 6H), 7.39-7.23 (m, 3H), 3.50 (s, 2H). MS (ESI): m/z 450 [M+1]$^+$

Example 22

Synthesis of 1-benzyl-3-(4-(3-bromophenyl)-2-oxo-2,3-dihydro-1H-benzo[b][1,4]diazepin-8-yl)urea (Compound 90)

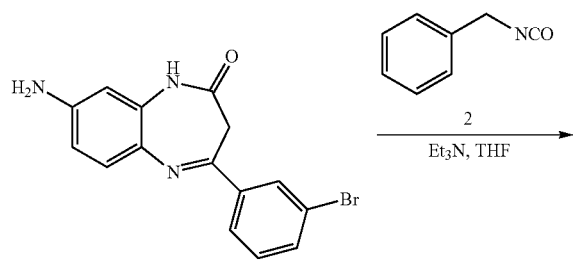

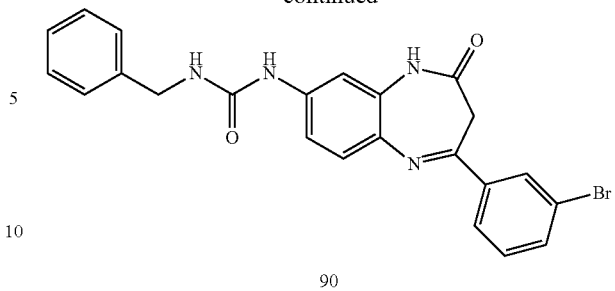

To a stirred solution of compound 1 (Example 19, Step 2; 200 mg, 0.60 mmol) in THF (10 mL) was added Et$_3$N (61.39 mg, 0.60 mmol) followed by benzylisocyanate (2) (80.85 mg, 0.60 mmol) at 0° C. under inert atmosphere. The resulting reaction mixture was allowed to warm to RT and stirred for 12 h; progress of the reaction was monitored by TLC. The precipitated solid was filtered and washed with diisopropylether (2×10 mL) to afford the title compound 90 (120 mg, 43%) as pale-green solid. $^1$H NMR (400 MHz, DMSO-d$_6$): δ□□□□52 (bs, 1H), 8.81 (s, 1H), 8.17 (s, 1H), 8.01 (d, J=8.0 Hz, 1H), 7.72 (d, J=7.6 Hz, 1H), 7.48 (t, J=8.0 Hz, 1H), 7.38-7.24 (m, 8H), 6.66-6.64 (m, 1H), 4.32 (d, J=5.2 Hz, 2H), 3.46 (s, 2H). MS (ESI): m/z 463.1 [M+1]$^+$

Example 23

Synthesis of 1-(4-(3-(2,6-dimethylpyridin-4-yl)phenyl)-2-oxo-2,3-dihydro-1H-benzo[b][1,4]diazepin-8-yl)-3-phenylurea (Compound 91)

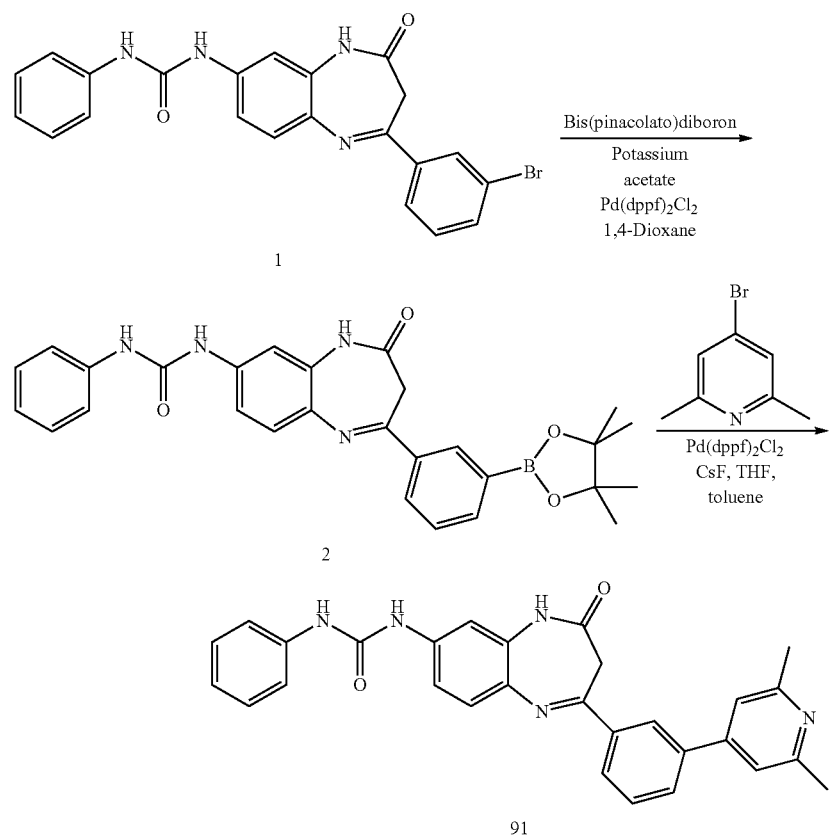

Step 1: Synthesis of 1-(2-oxo-4-(3-(4,4,5,5-tetramethyl-1,3,2-dioxaborolan-2-yl)phenyl)-2,3-dihydro-1H-benzo[b][1,4]diazepin-8-yl)-3-phenylurea (1)

To a stirred solution of compound 1 (Example 20; 150 mg, 0.33 mmol) in 1,4-dioxane (15 mL) were added bis(pinacolato)diboron (102 mg, 0.40 mmol) and potassium acetate (118.9 mg, 1.00 mmol) at RT under inert atmosphere and degassed for 15 min in argon atmosphere. To the resulting solution was added Pd(dppf)$_2$Cl$_2$ (24.47 mg, 0.03 mmol) at RT and again degassed for another 10 min. The resulting reaction mixture was heated to 100° C. and stirred for 12 h; progress of the reaction was monitored by TLC. The reaction mixture was allowed to cool to RT and concentrated under reduced pressure to obtain the crude. The crude material was purified by silica gel column chromatography (eluent: 5% MeOH/CH$_2$Cl$_2$) to afford 2 (70 mg, 42%) as an off-white solid. $^1$H NMR (500 MHz, DMSO-d$_6$): δ 10.54 (bs, 1H), 8.88 (s, 1H), 8.66 (s, 1H), 8.31 (s, 1H), 8.16 (d, J=8.0 Hz, 1H), 7.80 (d, J=7.5 Hz, 1H), 7.54 (t, J=7.5 Hz, 1H), 7.46 (d, J=7.5 Hz, 2H), 7.39 (s, 1H), 7.35-7.30 (m, 4H), 6.97 (t, J=7.0 Hz, 1H), 3.48 (s, 2H), 1.32 (s, 12H). MS (ESI): m/z 497 [M+1]$^+$ Step 2: Synthesis of 1-(4-(3-(2,6-dimethylpyridin-4-yl)phenyl)-2-oxo-2,3-dihydro-1H-benzo[b][1,4]diazepin-8-yl)-3-phenylurea (91)

To a stirred solution of 2 (70 mg, 0.14 mmol) in THF:toluene (10 mL, 1:1) were added 4-bromo-2,6-dimethylpyridine (26.25 mg, 0.14 mmol) and CsF (63.88 mg, 0.42 mmol) at RT under inert atmosphere and degassed for 15 min in argon atmosphere. To the resulting solution was added Pd(dppf)$_2$Cl$_2$ (10.31 mg, 0.014 mmol) at RT and again degassed for another 10 min. The resulting reaction mixture was heated to 80° C. and stirred for 12 h; progress of the reaction was monitored by TLC. The reaction mixture was allowed to cool to RT and concentrated under reduced pressure to obtain the crude. The crude material was purified by silica gel column chromatography (eluent: 5% MeOH/CH$_2$Cl$_2$) to afford the title compound 91 (4.2 mg, 6.26%) as pale-brown solid. $^1$H NMR (400 MHz, DMSO-d$_6$): δ 10.57 (bs, 1H), 8.90 (a, 1H), 8.68 (s, 1H), 8.33 (s, 1H), 8.11 (d, J=8.0 Hz, 1H), 7.90 (d, J=7.6 Hz, 1H), 7.65 (t, J=7.6 Hz, 1H), 7.58-7.42 (m, 5H), 7.38-7.29 (m, 4H), 6.98 (t, J=7.0 Hz, 1H), 3.58 (s, 2H), 2.50 (s, 6H). MS (ESI): m/z 476 [M+1]$^+$ Example 24

Synthesis of 1-benzyl-3-(4-(3-(2,6-dimethylpyridin-4-yl)phenyl)-2-oxo-2,3-dihydro-1H-benzo[b][1,4]diazepin-8-yl)urea (Compound 92)

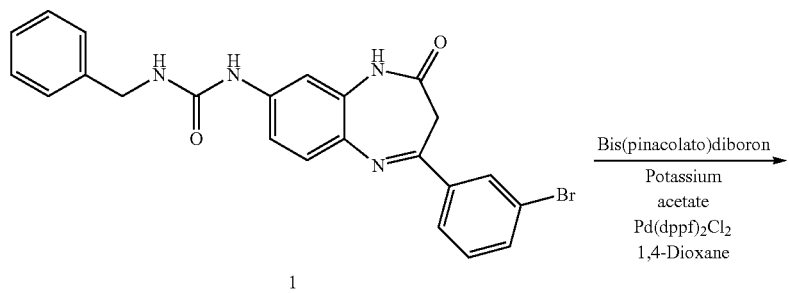

1

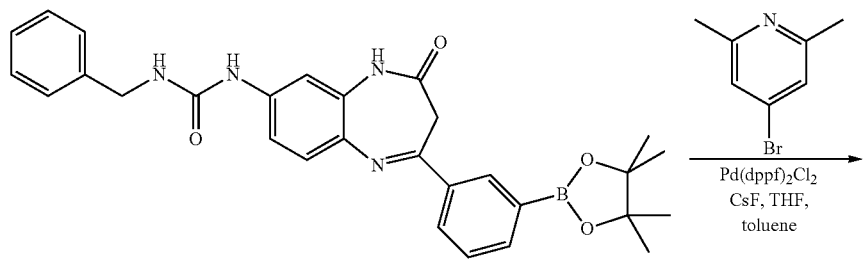

2

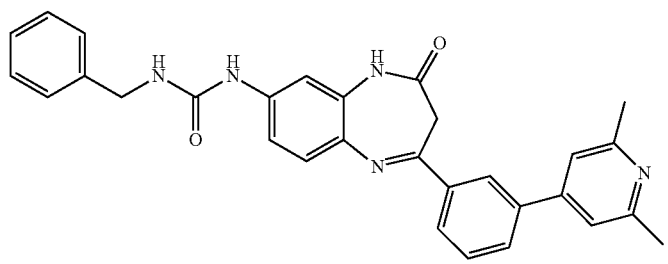

92

Step 1: Synthesis of 1-benzyl-3-(2-oxo-4-(3-(4,4,5,5-tetramethyl-1,3,2-dioxaborolan-2-yl)phenyl)-2,3-dihydro-1H-benzo[b][1,4]diazepin-8-yl)urea (2)

To a stirred solution of compound 1 (Example 22; 102 mg, 0.22 mmol) in 1,4-dioxane (15 mL) were added bis(pinacolato)diboron (67 mg, 0.26 mmol) and potassium acetate (78 mg, 0.66 mmol) at RT under inert atmosphere and degassed for 15 min in argon atmosphere. To the resulting solution was added Pd(dppf)$_2$Cl$_2$ (16 mg, 0.02 mmol) at RT and again degassed for another 10 min. The resulting reaction mixture was heated to 100° C. and stirred for 12 h; progress of the reaction was monitored by TLC. The reaction mixture was allowed to cool to RT and concentrated under reduced pressure to obtain the crude. The crude material was purified by silica gel column chromatography (eluent: 5% MeOH/CH$_2$Cl$_2$) to afford 1 (60 mg, 53.57%) as pale-green solid. $^1$H NMR (500 MHz, DMSO-d$_6$): δ 10.48 (bs, 1H), 8.77 (s, 1H), 8.30 (s, 1H), 8.15 (d, J=8.0 Hz, 1H), 7.79 (d, J=7.0 Hz, 1H), 7.53 (t, J=7.5 Hz, 1H), 7.36-7.31 (m, 8H), 6.63 (t, J=5.5 Hz, 1H), 4.31 (d, J=6.0 Hz, 2H), 3.90 (s, 2H), 1.31 (s, 12H).

Step 2: Synthesis of 1-benzyl-3-(4-(3-(2,6-dimethylpyridin-4-yl)phenyl)-2-oxo-2,3-dihydro-1H-benzo[b][1,4]diazepin-8-yl)urea (92)

To a stirred solution of 1 (60 mg, 0.12 mmol) in THF:toluene (10 mL, 1:1) were added 4-bromo-2,6-dimethylpyridine (22 mg, 0.12 mmol) and CsF (54 mg, 0.36 mmol) at RT under inert atmosphere and degassed for 15 min in argon atmosphere. To the resulting solution was added Pd(dppf)$_2$Cl$_2$ (8.0 mg, 0.012 mmol) at RT and again degassed for another 10 min. The resulting reaction mixture was heated to 80° C. and stirred for 12 h; progress of the reaction was monitored by TLC. The reaction mixture was allowed to cool to RT and concentrated under reduced pressure to obtain the crude. The crude material was purified by silica gel column chromatography (eluent: 5% MeOH/CH$_2$Cl$_2$) to afford the title compound 92 (6.0 mg, 10.16%) as yellow solid. $^1$H NMR (500 MHz, DMSO-d$_6$): δ 10.50 (bs, 1H), 9.64 (bs, 1H), 8.78 (bs, 1H), 8.31 (s, 1H), 8.09 (d, J=8.0 Hz, 1H), 7.88 (d, J=7.5 Hz, 1H), 7.63 (t, J=8.0 Hz, 1H), 7.42 (s, 2H), 7.38-7.31 (m, 3H), 7.25-7.23 (m, 5H), 6.64 (t, J=6.0 Hz, 1H), 4.31 (d, J=6.0 Hz, 2H), 3.56 (s, 2H), 2.49 (s, 6H). LCMS: m/z 490 [M+1]$^+$ Example 25

Synthesis of benzyl(4-(3-cyanophenyl)-2-oxo-2,3-dihydro-1H-benzo[b][1,4]diazepin-8-yl)carbamate (Compound 85)

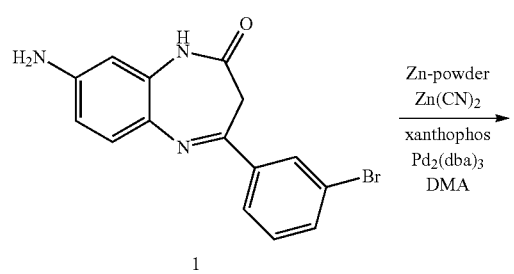

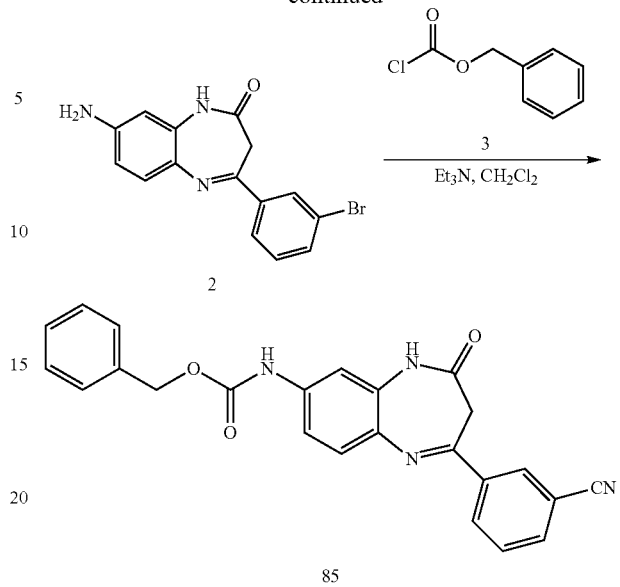

Step 1: Synthesis of 3-(8-amino-2-oxo-2,3-dihydro-1H-benzo[b][1,4]diazepin-4-yl)benzonitrile (2)

To a stirred solution of compound 1 (Example 19, Step 2; 1.0 g, 3.03 mmol) in DMA (20 mL) were added Zn-powder (39.5 mg, 0.60 mmol), Zn(CN)$_2$ (533 mg, 4.51 mmol) and xanthophos (630 mg, 1.12 mmol) at RT under N$_2$ atmosphere. The reaction mixture was degassed with argon for 15 min and then Pd$_2$(dba)$_3$ (556 mg, 0.60 mmol) was added and again degassed for another 15 min. The resulting reaction mixture was heated to 110° C. and stirred for 12 h; progress of the reaction was monitored by TLC. The reaction mixture was cooled to RT; diluted with water (20 mL) and extracted with EtOAc (2×20 mL). The combined organic extracts were dried over anhydrous Na$_2$SO$_4$ and concentrated under reduced pressure to obtain the crude. The crude material was purified by silica gel column chromatography eluting with 70% EtOAc/Hexane to afford compound 2 (520 mg, 62%). $^1$H NMR (400 MHz, DMSO-d$_6$): δ 10.34 (bs, 1H), 8.36 (s, 1H), 8.29 (d, J=8.0 Hz, 1H), 7.94 (d, J=7.6 Hz, 1H), 7.70 (t, J=7.6 Hz, 1H), 7.12 (d, J=8.4 Hz, 1H), 6.53-6.50 (m, 1H), 6.32 (d, J=2.4 Hz, 1H), 5.50 (s, 2H), 3.47 (s, 2H). MS (ESI): m/z 277 [M+1]$^+$ Step 2: Synthesis of benzyl(4-(3-cyanophenyl)-2-oxo-2,3-dihydro-1H-benzo[b][1,4]diazepin-8-yl)carbamate (85)

To a stirred solution of compound 2 (80 mg, 0.28 mmol) in CH$_2$Cl$_2$ (10 mL) was added Et$_3$N (0.2 mL, 1.15 mmol) followed by benzyl chloroformate (3) (0.1 mL, 0.86 mmol) at 0° C. under inert atmosphere. The resulting reaction mixture was allowed to warm to RT and stirred for 48 h; progress of the reaction was monitored by TLC. The reaction mixture was diluted with water (20 mL) and extracted with CH$_2$Cl$_2$ (2×20 mL). The combined organic extracts were dried over anhydrous Na$_2$SO$_4$ and concentrated under reduced pressure to obtain the crude. The crude material was purified by silica gel column chromatography eluting with 20% EtOAc/Hexane and then further purified by preparative HPLC to afford the title compound 85 (8 mg) as yellow solid. $^1$H NMR (400

MHz, DMSO-d$_6$): δ☐☐☐6☐ (bs, 1H), 10.02 (bs, 1H), 8.42 (s, 1H), 8.34 (d, J=8.0 Hz, 1H), 8.00 (d, J=7.6 Hz, 1H), 7.73 (t, J=7.6 Hz, 1H), 7.49-7.29 (m, 8H), 5.18 (s, 2H), 3.54 (s, 2H). MS (ESI): m/z 411 [M+1]$^+$

Example 26

Synthesis of phenyl(4-(3-cyanophenyl)-2-oxo-2,3-dihydro-1H-benzo[b][1,4]diazepin-8-yl)carbamate (Compound 84)

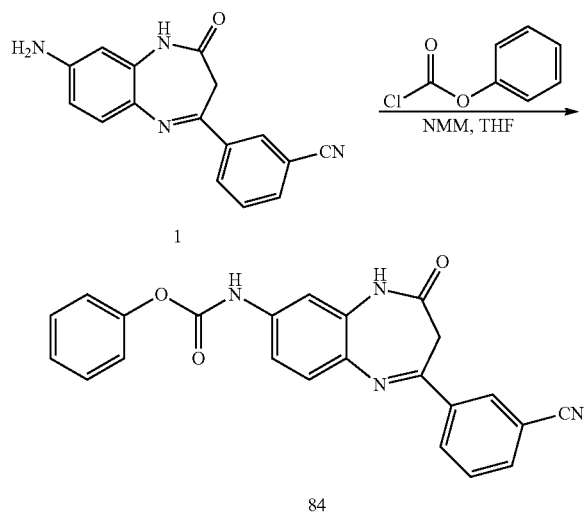

To a stirred solution of compound 1 (Example 25, Step 1; 40 mg, 0.14 mmol) in THF (5 mL) was added NMM (15 mg, 0.17 mmol) followed by phenyl chloroformate (27 mg, 0.17 mmol) at 0° C. under inert atmosphere. The resulting reaction mixture was allowed to warm to RT and stirred for 4 h; progress of the reaction was monitored by TLC. The reaction mixture was diluted with water (8 mL) and extracted with EtOAc (2×10 mL). The combined organic extracts were dried over anhydrous Na$_2$SO$_4$ and concentrated under reduced pressure. The crude material was purified by silica gel column chromatography eluting with 30% EtOAc/Hexane to afford the title compound 84 (12 mg, 21%) as yellow solid. $^1$H NMR (400 MHz, DMSO-d$_6$): δ 10.68 (bs, 1H), 10.47 (bs, 1H), 8.48 (s, 1H), 8.36 (d, J=8.0 Hz, 1H), 8.01 (d, J=7.6 Hz, 1H), 7.75 (t, J=7.6 Hz, 1H), 7.52 (s, 1H), 7.47-7.36 (m, 4H), 7.30-7.24 (m, 3H), 3.57 (s, 2H). MS (ESI): m/z 397.4 [M+1]+

Example 27

Synthesis of 1-benzyl-3-(4-(3-cyanophenyl)-2-oxo-2,3-dihydro-1H-benzo[b][1,4]diazepin-8-yl)urea (Compound 93)

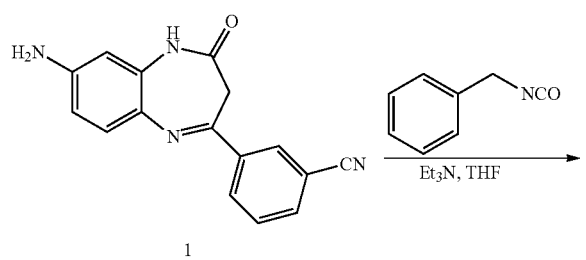

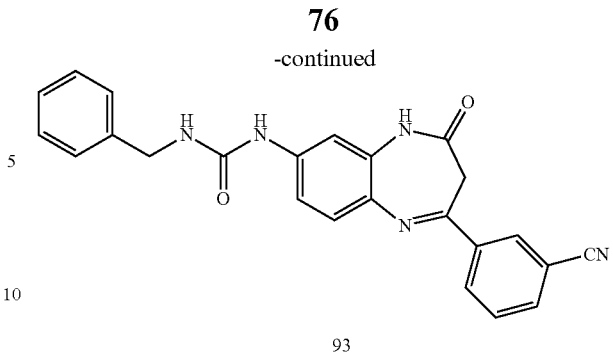

To a stirred solution of compound 1 (Example 25, Step 1; 40 mg, 0.14 mmol) in THF (5 mL) was added Et$_3$N (14 mg, 0.14 mmol) followed by benzyl isocyanate (19 mg, 0.14 mmol) at 0° C. under inert atmosphere. The resulting reaction mixture was allowed to warm to RT and stirred for 12 h; progress of the reaction was monitored by TLC. The reaction mixture was diluted with water (8 mL) and extracted with EtOAc (2×10 mL). The combined organic extracts were dried over anhydrous Na$_2$SO$_4$ and concentrated under reduced pressure. The crude material was purified by silica gel column chromatography eluting with 70% EtOAc/Hexane and then further purified by preparative HPLC to afford the title compound 93 (9 mg, 15%) as yellow solid. $^1$H NMR (400 MHz, DMSO-d$_6$): δ 10.54 (bs, 1H), 8.82 (s, 1H), 8.41 (s, 1H), 8.33 (d, J=8.0 Hz, 1H), 7.99 (d, J=7.6 Hz, 1H), 7.73 (t, J=8.0 Hz, 1H), 7.40 (d, J=2.0 Hz, 1H), 7.36-7.23 (m, 7H), 6.66-6.64 (m, 1H), 4.32 (d, J=6.0 Hz, 2H), 3.53 (s, 2H). MS (ESI): m/z 410 [M+1]$^+$ Example 28

Synthesis of 1-(4-(3-cyanophenyl)-2-oxo-2,3-dihydro-1H-benzo[b][1,4]diazepin-8-14)-3-phenylurea (Compound 94)

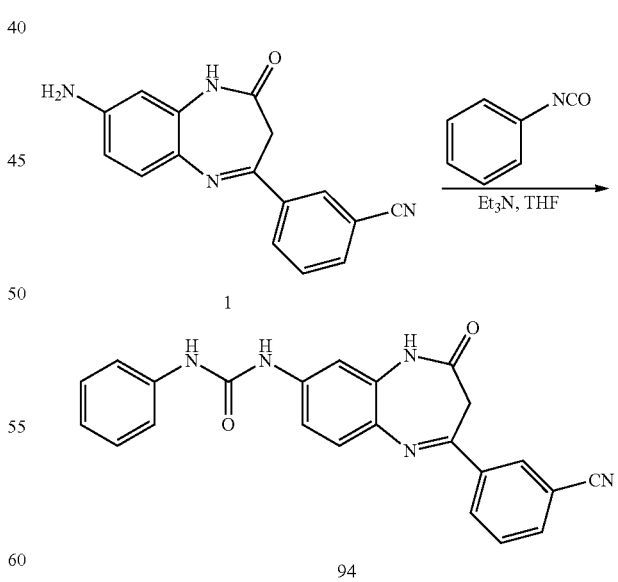

To a stirred solution of compound 1 (Example 25, Step 1; 40 mg, 0.14 mmol) in THF (5 mL) was added Et$_3$N (14 mg, 0.14 mmol) followed by phenylisocyanate (17 mg, 0.14 mmol) at 0° C. under inert atmosphere. The resulting reaction mixture was allowed to warm to RT and stirred for 2 h;

progress of the reaction was monitored by TLC. The reaction mixture was diluted with water (8 mL) and extracted with EtOAc (2×10 mL). The combined organic extracts were dried over anhydrous $Na_2SO_4$ and concentrated under reduced pressure. The crude material was purified by silica gel column chromatography eluting with 50% EtOAc/Hexane and then further purified by preparative HPLC to afford the title compound 94 (8 mg, 14%) as yellow solid. $^1$H NMR (400 MHz, DMSO-$d_6$): δ 10.61 (bs, 1H), 8.92 (s, 1H), 8.69 (s, 1H), 8.43 (s, 1H), 8.35 (d, J=8.0 Hz, 1H), 8.00 (d, J=8.0 Hz, 1H), 7.74 (t, J=7.6 Hz, 1H), 7.47-7.43 (m, 4H), 7.38-7.27 (m, 3H), 7.12 (t, J=7.6 Hz, 1H), 3.56 (s, 2H). MS (ESI): m/z 396 [M+1]$^+$ Example 29

Synthesis of 6-(8-bromo-2-oxo-2,3-dihydro-1H-benzo[b][1,4]diazepin-4-yl)benzo[d]thiazol-2(3H)-one (Compound 35)

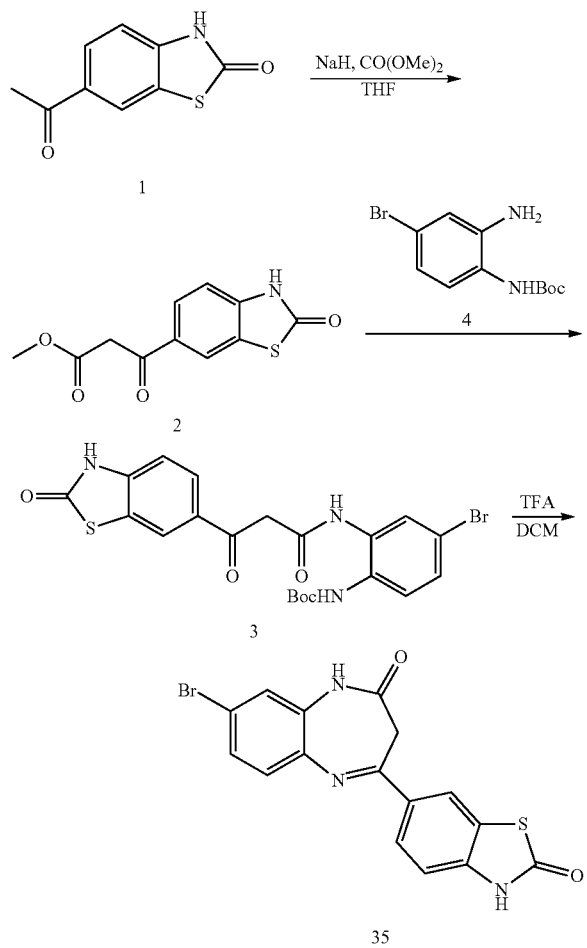

Step 1: Synthesis of methyl 3-oxo-3-(2-oxo-2,3-dihydrobenzo[d]thiazol-6-yl) propanoate (2)

A mixture of dimethyl carbonate (1.17 g, 13.0 mmol) and sodium hydride (60%, 520 mg, 13.0 mmol) in dry THF (30 mL) was stirred under reflux and compound 1 (1.0 g, 5.18 mmol) in dry THF (20 mL) was added drop wise. The reaction mixture was stirred under reflux for 12 h. The reaction mixture was washed with aq. $NH_4Cl$ (40 mL) and then extracted with ethyl acetate (40 mL×3). The organic layer was dried and concentrated to give the crude product which was purified by column chromatography on silica gel eluted with 0-30% of ethyl acetate in petroleum ether to give compound 2 (1.0 g, 77%).

Step 2: Synthesis of tert-butyl(4-bromo-2-(3-oxo-3-(2-oxo-2,3-dihydrobenzo[d]thiazol-6-yl) propanamido)phenyl)carbamate (3)

A mixture of compound 2 (1.0 g, 3.98 mmol) and compound 4 (1.14 g, 3.98 mmol) in toluene (50 mL) was stirred at 90° C. for 2 days. The reaction mixture was monitored by LC/MS. The mixture was purified by column chromatography on silica gel eluted with 0 to 30% of ethyl acetate in petroleum ether to give compound 3 (1.7 g, 85%).

Step 3: Synthesis of 6-(8-bromo-2-oxo-2,3-dihydro-1H-benzo[b][1,4]diazepin-4-yl)benzo[δ]thiazol-2(3H)-one (35)

To a solution of compound 3 (500 mg, 0.985 mmol) in DCM (20 mL) was added TFA (5 mL). The reaction mixture was stirred at room temperature for 2 h. The solvent was removed and the residue was purified by prep-HPLC to give the title compound 35 (50 mg, 13%). $^1$H NMR (400 MHz, DMSO-$d_6$) δ 12.22 (s, 1H), 10.65 (s, 1H), 8.32 (s, 1H), 8.03-8.00 (m, 1H), 7.43-7.31 (m, 3H), 7.24 (d, J=8.4 Hz, 1H), 3.54 (s, 2H). LC/MS: 387.9 (M+1), 389.9 (M+2)

Example 30

Synthesis of 6-(8-((2-fluorophenyl)ethynyl)-2-oxo-2,3-dihydro-1H-benzo[b][1,4]diazepin-4-yl)benzo[d]thiazol-2(3H)-one (Compound 36)

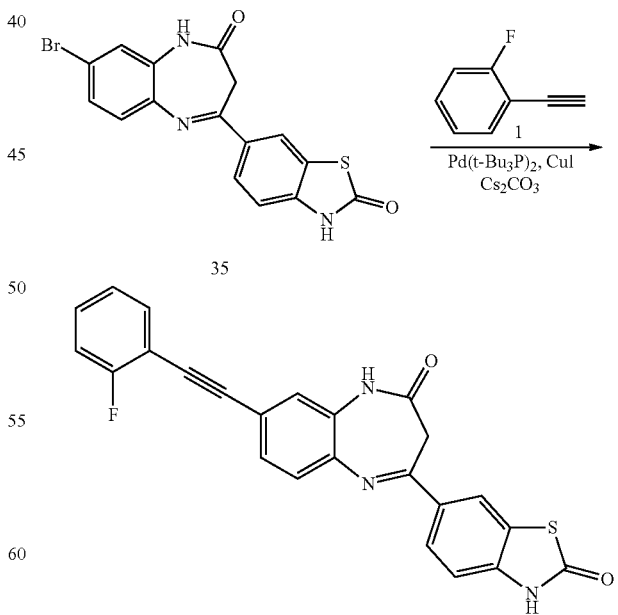

A mixture of compound 35 (Example 29; 200 mg, 0.52 mmol), compound 1 (188 mg, 1.56 mmol) $Cs_2CO_3$ (300 mg, 1.56 mmol), Pd(t-Bu₃P)₂ (20 mg) and CuI (20 mg) in DMF (10 mL) was stirred under N₂ at 80° C. for 2 h. The mixture was filtered and purified by column to give the crude product which was recrystallized with ethyl acetate to give the title compound 36 (40 mg, 18%). $^1$H NMR (400 MHz, DMSO-d₆) δ 12.37-12.06 (br, 1H), 10.65 (s, 1H), 8.34 (s, 1H), 8.04 (d, J=8.4 Hz, 1H), 7.68-7.61 (m, 1H), 7.52-7.47 (m, 1H), 7.46-7.33 (m, 4H), 7.32-7.21 (m, 2H), 3.57 (s, 2H). LC/MS: 428.1 (M+1)

Example 31

Synthesis of methyl 4-(3-cyanophenyl)-2-oxo-2,3-dihydro-1H-benzo[b][1,4]diazepine-8-carboxylate (Compound 42)

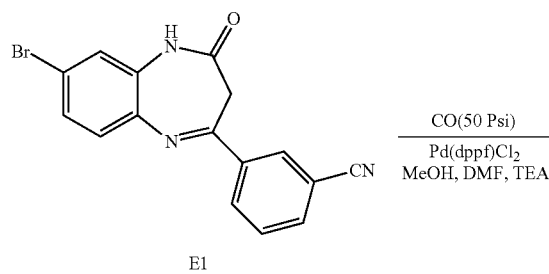

To the solution of compound E1 (1.2 g, 3.5 mmol) in DMF (15 mL) and MeOH (5 mL) was added Pd(dppf)Cl₂ (127 mg, 0.18 mmol) and TEA (5 mL). The mixture was heated at 80° C. under the atmosphere of CO (50 Psi) for 24 hrs. After removal of the solvent, the residue was extracted by EtOAc/H₂O (200 mL). The organic layer was dried over Na₂SO₄, concentrated and purified by prep-HPLC under formic acid to give the title compound 42 (600 mg, yield: 53.6%). $^1$H NMR (400 MHz, DMSO-d₆) δ 8.50 (s, 1H), 8.39 (d, J=8.4 Hz, 1H), 8.06 (d, J=7.6 Hz, 1H), 7.85 (s, 1H), 7.75-7.80 (m, 2H), 7.55 (d, J=8.8 Hz, 1H), 3.88 (s, 3H), 3.64 (s, 2H). LC/MS: 319.9 (M+1)

Example 32

Synthesis of 4-(3-cyanophenyl)-2-oxo-2,3-dihydro-1H-benzo[b][1,4]diazepine-8-carboxylic acid (Compound 40)

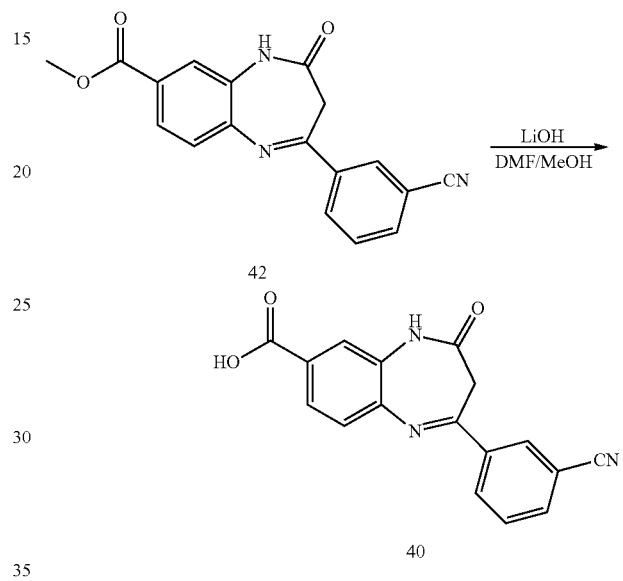

To the solution of compound 42 (Example 31; 100 mg, 0.31 mmol) in DMF/MeOH (1:1, 5 mL) was added LiOH (30 mg, 1.24 mmol) in H₂O (1 mL). The mixture was stirred at 50° C. for 4 hrs. After removal of the solvent, the residue was purified by prep-HPLC under formic acid to give the title compound 40 (29 mg, yield: 26.4%). $^1$H NMR (400 MHz, DMSO-d₆) δ 10.78 (s, 1H), 8.49 (s, 1H), 8.40 (d, J=8.4 Hz, 1H), 8.06 (d, J=7.6 Hz, 1H), 7.82 (s, 1H), 7.75-7.79 (m, 2H), 7.51 (d, J=8.4 Hz, 1H), 3.63 (s, 2H). LC/MS: 305.0 (M+1)

Example 33

Synthesis of 4-(3-cyanophenyl)-2-oxo-2,3-dihydro-1H-benzo[b][1,4]diazepine-8-carboxamide (Compound 54)

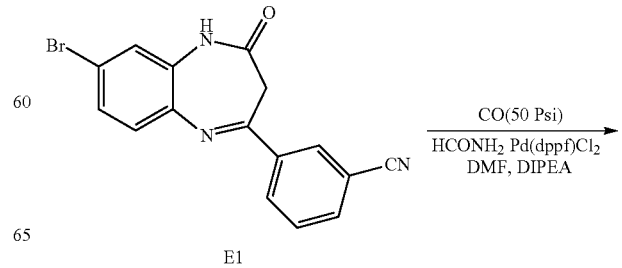

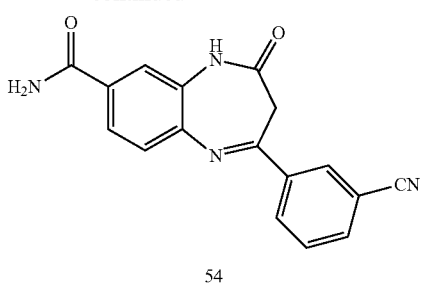

54

To the solution of compound E1 (400 mg, 1.18 mmol) in DMF (10 mL) was added Pd(dppf)Cl$_2$ (43.9 mg, 0.06 mmol), HCONH$_2$ (5 mL) and DIPEA (3 mL). The mixture was heated under the atmosphere of CO (50 Psi) at 80° C. for 1 day. After removal of the solvent, the residue was extracted by EtOAc/H$_2$O (200 mL). The organic layer was dried over Na$_2$SO$_4$, concentrated and purified by pre-HPLC under formic acid to give the title compound 54 (56 mg, yield: 15.6%). $^1$H NMR (400 MHz, DMSO-d$_6$) δ 10.76 (s, 1H), 8.49 (s, 1H), 8.38 (d, J=6.0 Hz, 1H), 8.04-8.06 (m, 2H), 7.73-7.79 (m, 3H), 7.49-7.50 (m, 2H), 3.61 (s, 2H). LC/MS: 304.8 (M+1)

Example 34

General Procedure for Preparation of Amides of Compound 40

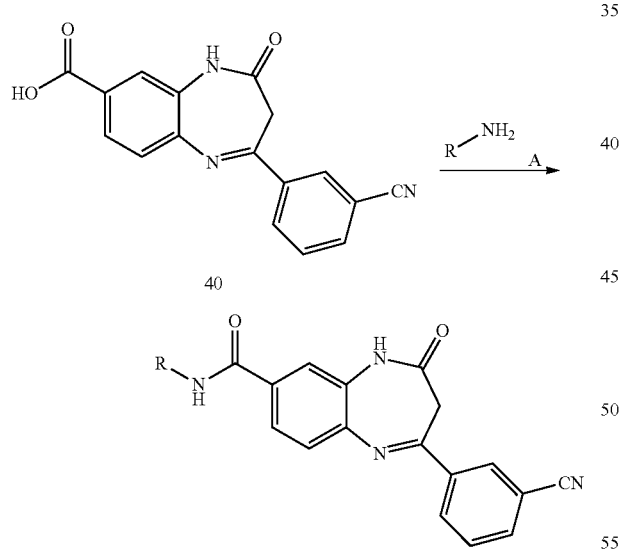

Procedure A1

To the solution of 40 (100 mg, 0.33 mmol) in DMF (5 mL) was added HATU (251 mg, 0.66 mmol), amine A (1.32 mmol) and TEA (0.5 mL). The mixture was stirred at 25° C. for 2 hrs. After removal of the solvent, the residue was purified by prep-HPLC under formic acid to give the desired compound.

Procedure B1

To the solution of 40 (100 mg, 0.33 mmol) in DMF (5 mL) was added TEA (0.5 mL). Propyl chloroformate (162 mg, 1.32 mmol) was added to the mixture at 0° C. and stirred at 0° C. for 30 min. Then, amine A (1.32 mmol) was added and stirred for another 2 hrs. After removal of the solvent, the residue was purified by prep-HPLC under formic acid to give the desired compound.

Example 35

Synthesis of 4-(3-cyanophenyl)-N-methyl-2-oxo-2,3-dihydro-1H-benzo[b][1,4]diazepine-8-carboxamide (Compound 47)

47

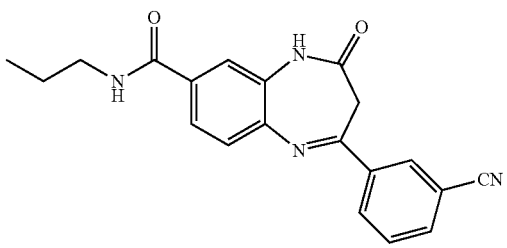

Using the method described for Procedure A1 the title compound 47 was obtained. $^1$H NMR (400 MHz, DMSO-d$_6$) δ 10.77 (s, 1H), 8.52 (d, J=4.8 Hz, 1H), 8.49 (s, 1H), 8.38 (d, J=6.8 Hz, 1H), 8.05 (d, J=6.4 Hz, 1H), 7.75-7.79 (m, 1H), 7.67-7.71 (m, 2H), 7.50 (d, J=8.4 Hz, 1H), 3.61 (s, 2H), 2.79 (d, J=4.8 Hz, 3H). LC/MS: 318.9 (M+1)

Example 36

Synthesis of 4-(3-cyanophenyl)-2-oxo-N-propyl-2,3-dihydro-1H-benzo[b][1,4]diazepine-8-carboxamide (Compound 44)

44

Using the method described for Procedure B1 the title compound 44 was obtained. $^1$H NMR (400 MHz, DMSO-d$_6$) δ 10.74 (s, 1H), 8.53-8.56 (m, 1H), 8.49 (s, 1H), 8.39 (d, J=8.0 Hz, 1H), 8.05 (d, J=6.8 Hz, 1H), 7.77-7.79 (m, 1H), 7.70-7.75

(m, 2H), 7.50 (d, J=5.2 Hz, 1H), 3.61 (s, 2H), 3.21-3.26 (m, 2H), 1.52-1.57 (m, 2H), 0.86-0.92 (m, 3H). LC/MS: 347.1 (M+1)

Example 37

Synthesis of N-allyl-4-(3-cyanophenyl)-2-oxo-2,3-dihydro-1H-benzo[b][1,4]diazepine-8-carboxamide (Compound 52)

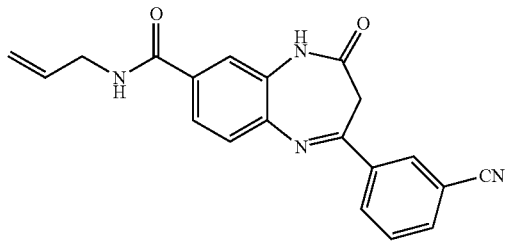

52

Using the method described for Procedure B1 the title compound 52 was obtained. $^1$H NMR (400 MHz, DMSO-$d_6$) δ 10.75 (s, 1H), 8.74-8.77 (m, 1H), 8.49 (s, 1H), 8.39 (d, J=6.0 Hz, 1H), 8.04-8.06 (m, 1H), 7.73-7.79 (m, 3H), 7.51 (d, J=8.8 Hz, 1H), 5.87-5.94 (m, 1H), 5.09-5.21 (m, 2H), 3.92-3.93 (m, 2H), 3.62 (s, 2H). LC/MS: 344.9 (M+1)

Example 38

Synthesis of 4-(3-cyanophenyl)-2-oxo-N-(prop-2-yn-1-yl)-2,3-dihydro-1H-benzo[b][1,4]diazepine-8-carboxamide (Compound 49)

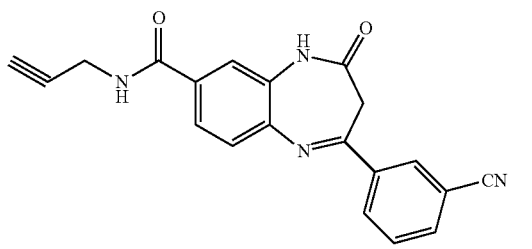

49

Using the method described for Procedure B1 the title compound 49 was obtained. $^1$H NMR (400 MHz, DMSO-$d_6$) δ 10.78 (s, 1H), 9.04-9.02 (m, 1H), 8.49 (s, 1H), 8.39 (d, J=6.8 Hz, 1H), 8.05 (d, J=7.6 Hz, 1H), 7.79-7.66 (m, 3H), 7.51 (d, J=8.8 Hz, 1H), 4.08-4.05 (m, 2H), 3.62 (s, 2H), 3.15-3.13 (m, 1H). LC/MS: 342.9 (M+1)

Example 39

Synthesis of 4-(3-cyanophenyl)-N,N-dimethyl-2-oxo-2,3-dihydro-1H-benzo[b][1,4]diazepine-8-carboxamide (Compound 48)

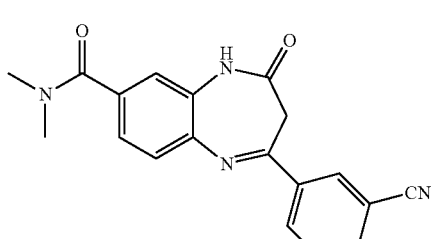

48

Using the method described for Procedure A1 the title compound 48 was obtained. $^1$H NMR (400 MHz, DMSO-$d_6$) δ 10.74 (s, 1H), 8.48 (s, 1H), 8.37 (d, J=7.2 Hz, 1H), 8.05-8.03 (m, 1H), 7.78-7.73 (m, 1H), 7.47 (d, J=8.4 Hz, 1H), 7.27 (d, J=8.0 Hz, 1H), 7.22 (s, 1H), 3.62 (s, 2H), 2.98-2.92 (m, 6H). LC/MS: 332.9 (M+1)

Example 40

Synthesis of 4-(3-cyanophenyl)-2-oxo-N-phenyl-2,3-dihydro-1H-benzo[b][1,4]diazepine-8-carboxamide (Compound 61)

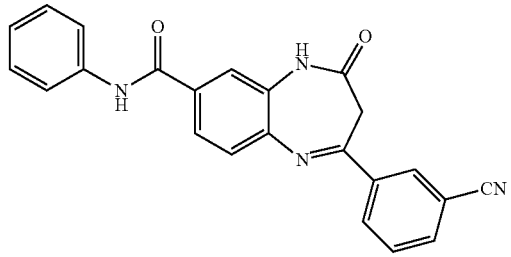

61

Using the method described for Procedure B1 the title compound 61 was obtained. $^1$H NMR (400 MHz, DMSO-$d_6$) δ 10.82 (s, 1H), 10.34 (s, 1H), 8.51 (s, 1H), 8.40 (d, J=8.0 Hz, 1H), 8.06 (d, J=8.0 Hz, 1H), 7.87 (d, J=2.0 Hz, 1H), 7.81-7.75 (m, 4H), 7.58 (d, J=8.0 Hz, 1H), 7.40-7.34 (m, 2H), 7.13-7.09 (m, 1H), 3.64 (s, 2H). LC/MS: 381.0 (M+1)

Example 41

Synthesis of N-benzyl-4-(3-cyanophenyl)-2-oxo-2,3-dihydro-1H-benzo[b][1,4]diazepine-8-carboxamide (Compound 45)

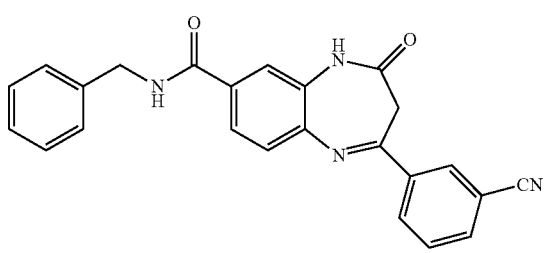

45

Using the method described for Procedure A1 the title compound 45 was obtained. $^1$H NMR (400 MHz, DMSO-$d_6$) δ 10.77 (s, 1H), 9.15 (t, J=6 Hz, 1H), 8.50 (s, 1H), 8.40 (d, J=8.0 Hz, 1H), 8.05 (d, J=6.8 Hz, 1H), 7.79-7.75 (m, 3H), 7.52 (d, J=8.8 Hz, 1H), 7.35-7.30 (m, 4H), 7.27-7.21 (m, 1H), 4.50 (d, J=6.0 Hz, 2H), 3.62 (s, 2H). LC/MS: 395.1 (M+1)

Example 42

Synthesis of methyl 2-(4-(3-cyanophenyl)-2-oxo-2,3-dihydro-1H-benzo[b][1,4]diazepine-8-carboxamido)acetate (Compound 55)

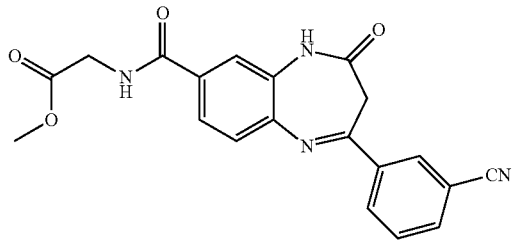

55

Using the method described for Procedure A1 the title compound 55 was obtained. $^1$H NMR (400 MHz, DMSO-$d_6$) δ 10.79 (s, 1H), 9.05 (t, J=6.0 Hz, 1H), 8.50 (s, 1H), 8.41-8.39 (m, 1H), 8.07-8.04 (m, 1H), 7.79-7.73 (m, 3H), 7.53 (d, J=8.8 Hz, 1H), 4.04-4.02 (d, J=6 Hz, 1H), 3.67 (s, 3H), 3.63 (s, 2H). LC/MS: 377.0 (M+1)

Example 43

Synthesis of 2-(4-(3-cyanophenyl)-2-oxo-2,3-dihydro-1H-benzo[b][1,4]diazepine-8-carboxamido)acetic acid (Compound 56)

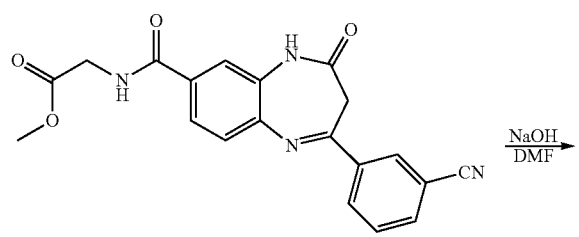

56

To the solution of 55 (Example 38; 87 mg, 0.23 mmol) in DMF (4 mL) was added NaOH (36.8 mg, 0.92 mmol) in H$_2$O (1 mL). The mixture was stirred at 25° C. for 1 hrs. After removal of the solvent, the residue was purified by prep-HPLC under formic acid to give the title compound 56 (27 mg, yield: 32.2%). $^1$H NMR (400 MHz, DMSO-$d_6$) δ 10.80 (s, 1H), 8.94 (t, J=5.0 Hz, 1H), 8.50 (s, 1H), 8.40 (d, J=8.0 Hz, 1H), 8.06 (d, J=8.0 Hz, 1H), 7.73-7.80 (m, 3H), 7.54 (d, J=9.2 Hz, 1H), 3.94 (d, J=5.2 Hz, 2H), 3.63 (s, 2H). LC/MS: 304.8 (M+1)

Example 44

Synthesis of tert-butyl(4-(3-cyanophenyl)-2-oxo-2,3-dihydro-1H-benzo[b][1,4]diazepin-8-yl)carbamate (Compound 63)

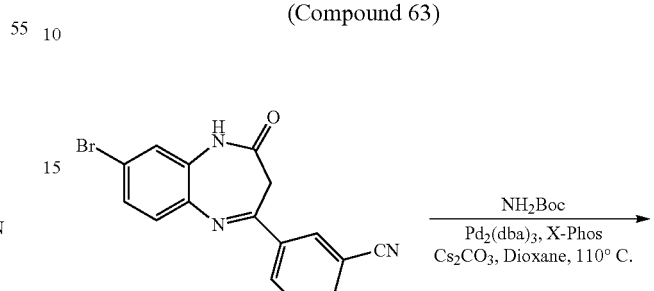

E1

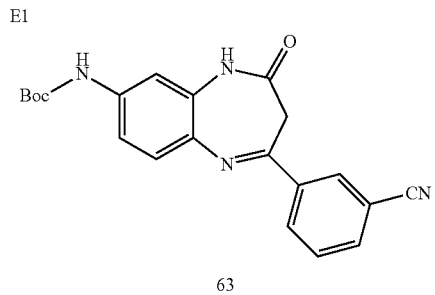

63

To the solution of compound E1 (400 mg, 1.18 mmol) in Dioxane (15 mL) was added NH$_2$Boc (277 mg, 2.36 mmol), X-phos (95 mg, 0.2 mmol), Pd$_2$(dba)$_3$ (161 mg, 0.2 mmol) and Cs$_2$CO$_3$ (769 mg, 2.36 mmol). The mixture was heated under the atmosphere of N$_2$ at 100° C. for 5 hrs. After removal of the solvent, the residue was extracted by EtOAc/H$_2$O (200 mL). The organic layer was dried over Na$_2$SO$_4$, concentrated and purified by prep-HPLC under formic acid to give the title compound 63 (200 mg, yield: 45.0%). $^1$H NMR (400 MHz, DMSO-$d_6$) δ 10.58 (s, 1H), 9.62 (s, 1H), 8.43 (t, J=1.7 Hz, 1H), 8.34 (d, J=8.1 Hz, 1H), 8.01 (d, J=7.7 Hz, 1H), 7.74 (t, J=7.9 Hz, 1H), 7.52 (d, J=2.2 Hz, 1H), 7.33 (d, J=8.8 Hz, 1H), 7.26 (dd, J=2.3, 8.8 Hz, 1H), 3.54 (s, 2H), 1.50 (s, 9H). LC/MS: 377.0 (M+1)

Example 45

Synthesis of 3-(8-amino-2-oxo-2,3-dihydro-1H-benzo[b][1,4]diazepin-4-yl)benzonitrile (Compound 59)

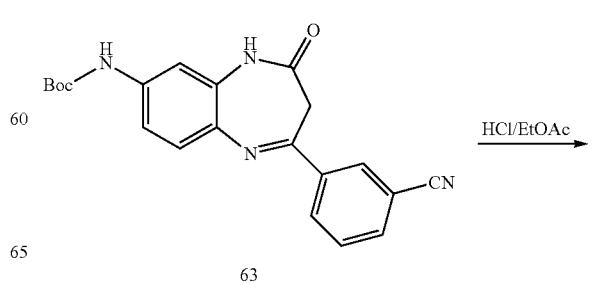

63

-continued

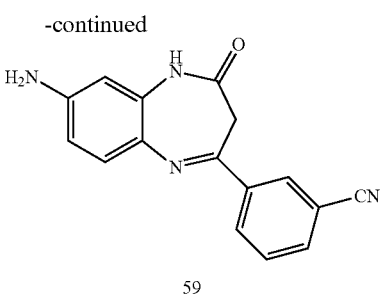

59

To the solution of compound 63 (Example 44; 200 mg, 0.53 mmol) in EtOAc (5 mL) was added HCl/EtOAc (5 mL). It was stirred at 25° C. for 24 hrs. After removal of the solvent, the residue was extracted by EtOAc/H$_2$O (200 mL). The organic layer was dried over Na$_2$SO$_4$, concentrated and purified by pre-HPLC under formic acid to give the title compound 59 (140 mg, yield: 95.9%). $^1$H NMR (400 MHz, DMSO-d$_6$) δ 10.35 (s, 1H), 8.35 (s, 1H), 8.28 (d, J=7.6 Hz, 1H), 7.93 (d, J=7.6 Hz, 1H), 7.69 (t, J=6 Hz, 1H), 7.11 (d, J=8.4 Hz, 1H), 6.49 (d, J=8.4 Hz, 1H), 6.30 (d, J=6.4 Hz, 1H), 5.51 (s, 2H), 3.46 (s, 2H). LC/MS: 277.0 (M+1)

Example 46

Synthesis of N-(4-(3-cyanophenyl)-2-oxo-2,3-dihydro-1H-benzo[b][1,4]diazepin-8-yl)acetamide (Compound 60)

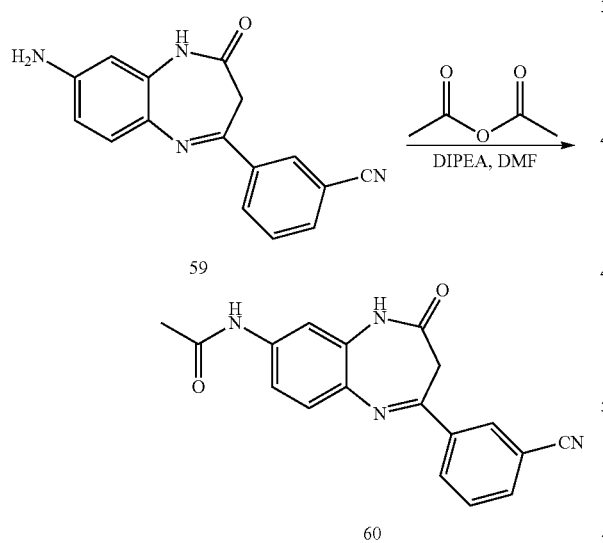

To the solution of compound 59 (Example 45; 70 mg, 0.25 mmol) in DMF (5 mL) was added DIPEA (0.5 mL). (MeCO)$_2$O (102 mg, 1.0 mmol) was added to the mixture below 0° C. The mixture was stirred at 0° C. for 3 hrs. After removal of the solvent, the residue was extracted by EtOAc/H$_2$O (200 mL). The organic layer was dried over Na$_2$SO$_4$, concentrated and purified by prep-HPLC under formic acid to give the title compound 60 (25 mg, yield: 31.4%). $^1$H NMR (400 MHz, DMSO-d$_6$) δ 10.65 (s, 1H), 10.65 (s, 1H), 8.44 (s, 1H), 8.34 (d, J=6.0 Hz, 1H), 8.01 (d, J=7.6 Hz, 1H), 7.74 (t, J=8.0 Hz, 1H), 7.61 (d, J=2.0 Hz, 1H), 7.39 (d, J=2.0 Hz, 1H), 7.36 (d, J=8.8 Hz, 1H), 3.55 (s, 2H), 2.07 (s, 3H). LC/MS: 319.0 (M+1)

Example 47

Synthesis of N-(4-(3-cyanophenyl)-2-oxo-2,3-dihydro-1H-benzo[b][1,4]diazepin-8-yl)methanesulfonamide (Compound 62)

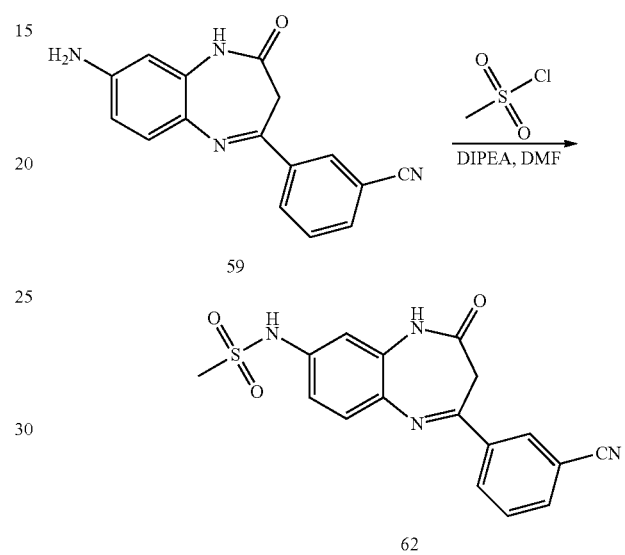

To the solution of compound 59 (Example 41; 70 mg, 0.25 mmol) in DMF (5 mL) was added with DIPEA (0.5 mL). MeSO$_2$Cl (112 mg, 1.0 mmol) was added to the mixture below 0° C. It was stirred at 0° C. for 3 hrs. After removal of the solvent, the residue was extracted by EtOAc/H$_2$O (200 mL). The organic layer was dried over Na$_2$SO$_4$, concentrated and purified by prep-HPLC under formic acid to give the title compound 62 (7 mg, yield: 8.0%). $^1$H NMR (400 MHz, DMSO-d$_6$) δ 10.64 (s, 1H), 10.65 (s, 1H), 8.43 (t, J=2.0 Hz, 1H), 8.34 (d, J=8.0 Hz, 1H), 8.00 (d, J=8.8 Hz, 1H), 7.74 (t, J=8.0 Hz, 1H), 7.39 (d, J=8.4 Hz, 1H), 7.10-7.06 (m, 2H), 3.57 (s, 2H), 3.05 (s, 3H). LC/MS: 354.9 (M+1)

General Procedure for Preparation of Compounds Via Displacement

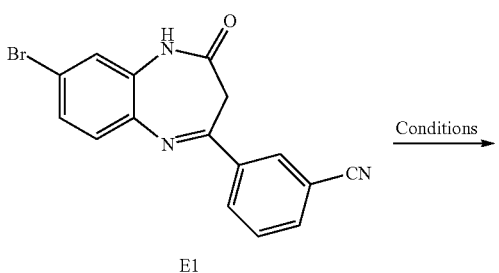

E1

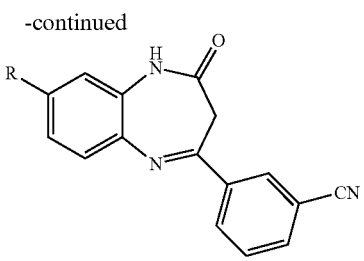

Procedure A2 (Suzuki Coupling).

A mixture of compound E1 (200 mg, 0.59 mmol), boric acid (245 mg, 1.48 mmol), Pd(dppf)Cl$_2$ (42 mg, 0.06 mmol), and Cs$_2$CO$_3$ (341 mg, 1.77 mmol) in a mixed solution (DMF: 5 mL, water: 3 mL). The reaction mixture was heated with microwave at 150° C. for 3 h. The reaction mixture was filtered and purified by Prep-HPLC to give the product.

Procedure B2 (Suzuki Coupling):

To a solution of compound E1 (150 mg, 0.44 mmol), boric acid (198 mg, 1.10 mmol), and Et$_3$N (111 mg, 1.10 mmol) in DMF: (5 mL) was added Pd(t-Bu$_3$P)$_2$ (15 mg). The reaction mixture was stirred at 80° C. for 3 h. Water (10 mL) was added and filtered to give the solid product.

Example 48

Synthesis of 2-(4-(3-cyanophenyl)-2-oxo-2,3-dihydro-1H-benzo[b][1,4]diazepin-8-yl)benzoic acid (Compound 41)

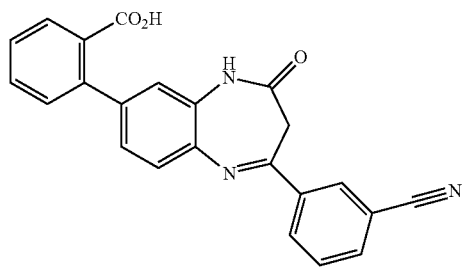 [SMILES: N#Cc1cccc(C2=Nc3ccc(-c4ccccc4C(=O)O)cc3NC(=O)C2)c1]

Using the method described for Procedure A2 the title compound 41 was obtained. $^1$H NMR (400 MHz, DMSO-d$_6$) δ 13.20-12.60 (br, 1H), 10.76 (s, 1H), 8.51 (s, 1H), 8.49 (d, J=1.2 Hz, 1H), 8.06 (d, J=0.9 Hz, 1H), 7.82-7.73 (m, 2H), 7.66-7.57 (m, 1H), 7.53-7.43 (m, 3H), 7.23-7.15 (m, 2H), 3.62 (s, 2H). LC/MS: 382.1 (M+1)

Example 49

Synthesis of methyl 3-(4-(3-cyanophenyl)-2-oxo-2,3-dihydro-1H-benzo[b][1,4]diazepin-8-yl)benzoate (Compound 50)

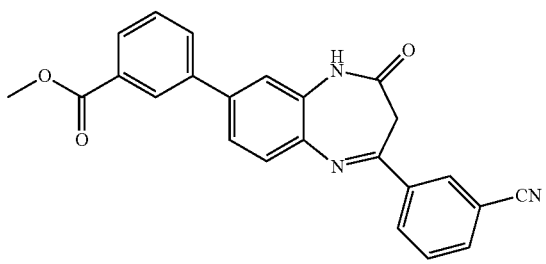 [SMILES: COC(=O)c1cccc(-c2ccc3c(c2)NC(=O)CC(c2cccc(C#N)c2)=N3)c1]

Using the method described for Procedure B2 the title compound 50 was obtained. $^1$H NMR (400 MHz, DMSO-d$_6$) δ 10.72 (s, 1H), 8.50 (s, 1H), 8.40 (d, J=7.6 Hz, 1H), 8.24 (s, 1H), 8.05 (d, J=7.2 Hz, 1H), 8.00-7.96 (m, 2H), 7.79-7.71 (m, 1H), 7.69-7.60 (m, 2H), 7.59-7.53 (m, 2H), 3.91 (s, 3H), 3.65 (s, 2H). LC/MS: 396.1 (M+1)

Example 50

Synthesis of 3-(4-(3-cyanophenyl)-2-oxo-2,3-dihydro-1H-benzo[b][1,4]diazepin-8-yl)benzoic acid (Compound 46)

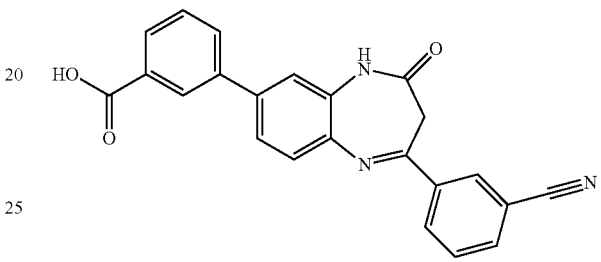

Using the method described for Procedure A2 the title compound 46 was obtained. $^1$H NMR (400 MHz, DMSO-d$_6$) δ 13.20-13.00 (br, 1H), 10.68 (s, 1H), 8.47 (s, 1H), 8.37 (d, J=8.0 Hz, 1H), 8.20 (s, 1H), 8.01 (d, J=8.0 Hz, 1H), 8.96-8.91 (m, 2H), 7.78-7.71 (m, 1H), 7.63-7.54 (m, 2H), 7.55-7.50 (m, 2H), 3.62 (s, 2H). LC/MS: 382.0 (M+1)

Example 51

Synthesis of methyl 4-(4-(3-cyanophenyl)-2-oxo-2,3-dihydro-1H-benzo[b][1,4]diazepin-8-yl)benzoate (Compound 51)

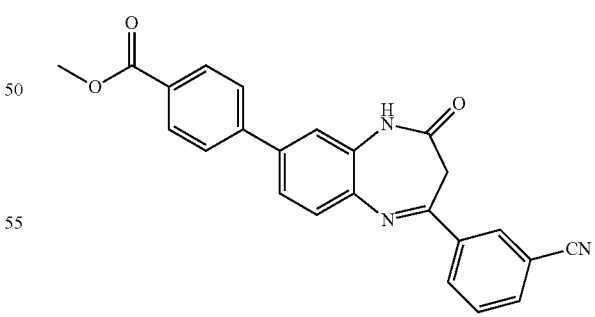

Using the method described for Procedure B2 the title compound 51 was obtained. $^1$H NMR (400 MHz, DMSO-d$_6$) δ 10.74 (s, 1H), 8.49 (s, 1H), 8.09 (d, J=8.4 Hz, 1H), 8.05 (d, J=7.6 Hz, 3H), 7.85 (d, J=8.4 Hz, 2H), 7.80-7.73 (m, 1H), 7.68-7.62 (m, 1H), 7.59-7.53 (m, 2H), 3.98 (s, 3H), 3.65 (s, 2H). LC/MS: 396.0 (M+1)

Example 52

Synthesis of 4-(4-(3-cyanophenyl)-2-oxo-2,3-dihydro-1H-benzo[b][1,4]diazepin-8-yl)benzoic acid (Compound 43)

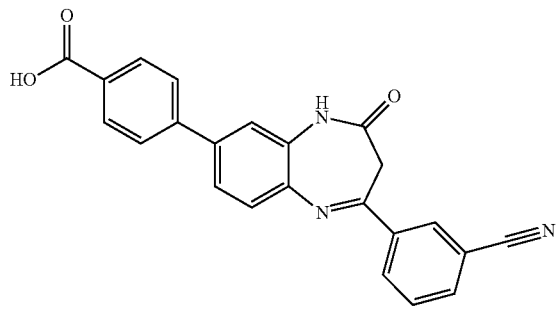 [SMILES: N#Cc1cccc(C2=Nc3ccc(-c4ccc(C(=O)O)cc4)cc3NC(=O)C2)c1]

Using the method described for Procedure A2 the title compound 43 was obtained. ¹H NMR (400 MHz, DMSO-d₆) δ 10.71 (s, 1H), 8.46 (s, 1H), 8.37 (d, J=8.4 Hz, 1H), 8.01 (d, J=8.0 Hz, 1H), 7.97 (d, J=8.4 Hz, 2H), 7.78-7.71 (m, 1H), 7.67 (d, J=8.4 Hz, 2H), 7.61-7.56 (m, 1H), 7.53-7.48 (m, 2H), 3.62 (s, 2H). LC/MS: 382.0 (M+1)

Example 53

Synthesis of (E)-methyl 3-(4-(3-cyanophenyl)-2-oxo-2,3-dihydro-1H-benzo[b][1,4]diazepin-8-yl)acrylate (Compound 53)

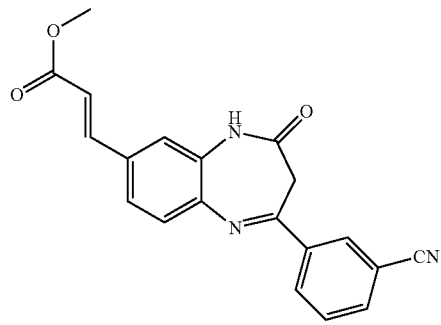 [SMILES: COC(=O)/C=C/c1ccc2c(c1)NC(=O)CC(c1cccc(C#N)c1)=N2]

Using the method described for Procedure B2 the title compound 53 was obtained. ¹H NMR (400 MHz, DMSO-d₆) δ 10.69 (s, 1H), 8.45 (s, 1H), 8.35 (d, J=8.0 Hz, 1H), 8.02 (d, J=8.0 Hz, 1H), 7.78-7.71 (m, 1H), 7.68-7.61 (m, 2H), 7.47-7.38 (m, 2H), 6.60 (d, J=16.0 Hz, 1H), 3.71 (s, 3H), 3.59 (s, 2H). LC/MS: 346.1 (M+1)

Example 54

Synthesis of (E)-3-(4-(3-cyanophenyl)-2-oxo-2,3-dihydro-1H-benzo[β][1,4]diazepin-8-yl)acrylic acid (Compound 58)

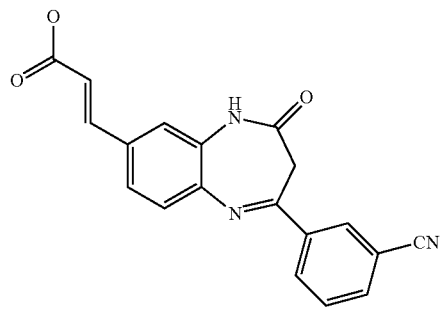 [SMILES: N#Cc1cccc(C2=Nc3ccc(/C=C/C(=O)O)cc3NC(=O)C2)c1]

Using the method described for Procedure B2 the title compound 58 was obtained. ¹H NMR (400 MHz, DMSO-d₆) δ 8.48 (s, 1H), 8.38 (d, J=8.4 Hz, 1H), 8.04 (d, J=7.6 Hz, 1H), 7.80-7.72 (m, 1H), 7.62-7.50 (m, 2H), 7.48-7.41 (m, 2H), 6.52 (d, J=16.0 Hz, 1H), 3.62 (s, 2H). LC/MS: 332.0 (M+1)

Example 55

Effect of 8-bromo-4-(pyridazin-4-yl)-1H-benzo[b][1,4]diazepin-2(3H)-one (Compound 1) on Neuronal Differentiation of Human Neural Stem Cells Human neural stem cells (hNSCs) were isolated and grown in monolayer culture, plated, treated with varying concentrations of 8-bromo-4-(pyridazin-4-yl)-1H-benzo[b][1,4]diazepin-2(3H)-one (Compound 1), and stained with TUJ-1 antibody, as described in U.S. Patent Application Publication No. US2007/0015138. Mitogen-free test media with a positive control for neuronal differentiation was used along with basal media without growth factors as a negative control. Results are shown in FIG. 1, which shows concentration response curves of neuronal differentiation after subtraction of background media values. The data are presented as a percent of neuronal positive control. The data indicate that Compound 1 promoted neuronal differentiation in a concentration dependent manner while DCG-IV did not induce neurogenesis over the dose range tested. The combination of Compound 1 with DCG-IV at equal doses (1:1 ratio) over the same dose range did not induce neurogenesis. This showed the inhibitory effect of DCG-IV, an mGluR2/3 agonist, on the neurogenesis induced by Compound 1.

Non-limiting examples of other compounds of the invention on human neuronal differentiation are shown in Table 2. The same protocol used for exemplary Compound 1 (FIG. 1 and Example 55) was used to test these compounds. LY-354740 (eglumegad) is an agonist of the group II mGlu receptors.

TABLE 2

Neuronal Differentiation of Human Neural Stem Cells

| Compound | Neurogenesis EC$_{50}$ | Inhibition by DCG-IV | Inhibition by LY-354740 |
|---|---|---|---|
| Compound 1 | B | I | ND |
| Compound 2 | B | ND | I |
| Compound 3 | B | ND | I |
| Compound 4 | B | ND | ND |
| Compound 5 | A | ND | ND |
| Compound 6 | B | ND | ND |
| Compound 7 | C | ND | ND |
| Compound 8 | C | ND | ND |
| Compound 9 | B | ND | ND |
| Compound 10 | B | ND | ND |
| Compound 11 | B | ND | ND |
| Compound 12 | A | ND | I |
| Compound 13 | C | ND | ND |
| Compound 15 | B | I | I |
| Compound 16 | C | ND | ND |
| Compound 17 | C | ND | ND |

Neurogenesis EC$_{50}$: A <1.0 μM; B 1-5 μM; C >5 μM.
Inhibition by DCG-IV: I—Inhibition; ND—Not determined.

Example 56

Determination of Synergy

The presence of synergy is determined by use of a combination index (CI). The CI based on the $EC_{50}$ is used to determine whether a pair of compounds have an additive, synergistic (greater than additive), or antagonistic effect when run in combination. The CI is a quantitative measure of the nature of drug interactions, comparing the $EC_{50}$'s of two compounds, when each is assayed alone, to the $EC_{50}$ of each compound when assayed in combination. The combination index (CI) is equal to the following formula:

$$\frac{C1}{IC1} + \frac{C2}{IC2} + \frac{(C1*C2)}{(IC1*IC2)}$$

were C1 and C2 are the concentrations of a first and a second compound, respectively, resulting in 50% activity in neuronal differentiation when assayed in combination; and IC1 and IC2 are the concentrations of each compound resulting in 50% activity when assayed independently.

A CI of less than 1 indicates the presence of synergy; a CI equal to 1 indicates an additive effect; and a CI greater than 1 indicates antagonism between the two compounds.

The above is based on the selection of $EC_{50}$ as the point of comparison for the two compounds. The comparison is not limited by the point used, but rather the same comparison may be made at another point, such as $EC_{20}$, $EC_{30}$, $EC_{40}$, $EC_{60}$, $EC_{70}$, $EC_{80}$, or any other EC value above, below, or between any of those points.

Example 57

Binding Assays

The compounds are further characterized through binding assays known in the art for studying potential mGluR agents. As a non-limiting example, the assay may be conducted as follows. Membranes are prepared and resuspended in cold 50 mM Tris-HCl buffer containing 2 mM $MgCl_2$ (pH 7) (binding buffer). The final concentration of the membranes in the assays is 20-30 µg protein/mL Inhibition experiments are performed with the membranes incubated with 10 nM [$^3$H]-LY354740, DCG-IV or another agonist at room temperature, for 1 hour, in the presence of various concentrations of the compound to be tested. Following the incubation, membranes are filtered onto Whatmann GF/B glass fiber filters and washed 5 times with cold binding buffer. After transfer of the filters into plastic vials containing 10 mL of Ultima-gold scintillation fluid from Perkin-Elmer (Boston, Mass., USA), the radioactivity is measured by liquid scintillation in a Tri-Carb 2500 TR counter (Packard). The inhibition curves are fitted with a four parameter logistic equation giving $IC_{50}$ values.

Example 58

Functional Assay (FLIPR)

The compounds are further characterized through functional assays known in the art for studying potential mGluR agents. As a non-limiting example, the assay may be conducted as follows. Chinese hamster ovary (CHO) cells stably over-expressing either mGluR2 or mGluR3 are seeded into multiwell plates and transiently transfected overnight at 37° C. with a cDNA construct expressing G-protein coupled to intracellular calcium such as Gα16. The following day cells are washed with Hank's balanced salt solution containing calcium and magnesium. Cells are loaded for 1-2 hours with a calcium dye such as Fluo4 at 37° C.

The test compound may be added prior to or concurrent with the loading of the cells with Fluo4. Pre-incubation with compounds can vary from 5 minutes up 2 hours. Pre-incubation is done if the assay is testing for antagonists, positive allosteric modulators or negative allosteric modulators. No pre-incubation is done if the assay is testing for agonist activity. For testing antagonists or negative allosteric modulators an $EC_{80}$ of the endogenous ligand, glutamate, is used. For testing positive allosteric modulators an $EC_{20}$ of the endogenous ligand, glutamate, is used. Cells plates are loaded into a real-time fluorescence reader such as the FLIPR Tetra or the Flexstation 3. A base line is recorded for 15 seconds before cells are stimulated with either glutamate or other agonists. The real-time fluorescent signal is recorded for another 2 minutes. The peak of the fluorescent signal is determined. Data are either expressed as percent of the glutamate response in terms of a single determination or concentration curves are fitted with a four parameter logistic equation giving $EC_{50}$ or $IC_{50}$ values.

Example 59

GIRK Assay

A second functional assay known in the art may be used to verify the activity of potential mGluR agents. As a non-limiting example, the GIRK assay may be conducted as follows. Human embryonic kidney (HEK 293) cells stably expressing both human metabotropic glutamate receptor 2 (mGluR2) and G protein-coupled inwardly-rectifying potassium (GIRK) channel are seeded in poly-D lysine coated multi-well plates overnight at 37° C. The following day the cells are washed three times with a buffer consisting of Hank's balanced salt solution (HBSS) and Hepes. Cells are then loaded with FluoZin-2 dye for 1 hour at room temperature. Cells are again washed three times and the FluoZin-2 dye is replaced with the HBSS/Hepes buffer.

A baseline measurement is made for 3 minutes at 2-second intervals using a real-time fluorescence reader such as the Hamamatsu FDSS7000. Afterwards, the test compounds are added to the cells and incubated at room temperature for 1 hour. A buffer containing thallium sulfate and glutamate (at the $EC_{80}$ concentration) is then added to the cells and fluorescence measurements are recorded for 7 minutes at 1-second intervals. The calculated signal is determined by subtracting the baseline reading and utilizes the AUC from 5-15 seconds after the thallium addition. Data is expressed as percent of glutamate response.

Benzodiazepines

Synthesized Compounds—Representative Functional Data

TABLE 3

| Compound Number | mGluR2 FLIPR | mGluR2 GIRK | mGluR3 FLIPR |
|---|---|---|---|
| 11 | C | E | C |
| 33 | C |  | B |

TABLE 3-continued

| Compound Number | mGluR2 FLIPR | mGluR2 GIRK | mGluR3 FLIPR |
|---|---|---|---|
| 35 | B | E | C |
| 36 | C | E | C |
| 44 | C | E | |
| 47 | C | E | |
| 48 | B | E | |
| 63 | B | E | |
| 71 | C | E | |
| 82 | A | E | |
| 83 | B | B | |
| 86 | | D | |
| 87 | | E | |
| 88 | | D | |
| 92 | B | C | |

A=$IC_{50}$<1 μM; B=inhibition at 101.1M>50%; C=inhibition at 101.1M<50%; D=inhibition at 2 μM>50%; E=inhibition at 2 μM<50%

All references cited herein, including patents, patent applications, and publications, are hereby incorporated by reference in their entireties, whether previously specifically incorporated or not.

Having now fully provided the instant disclosure, it will be appreciated by those skilled in the art that the same can be performed within a wide range of equivalent parameters, concentrations, and conditions without departing from the spirit and scope of the disclosure and without undue experimentation.

While the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

What is claimed is:

1. A compound of Formula (I)

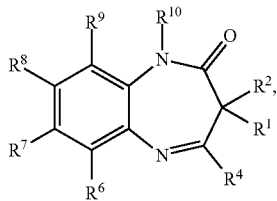

or a pharmaceutically acceptable salt, stereoisomer, or tautomer thereof, wherein:

$R^1$ and $R^2$ are independently H, halogen, $C_1$-$C_8$ alkyl, —$NR^{11}R^{12}$, —$SR^{13}$, $C_3$-$C_6$ heteroalkyl containing 1-4 heteroatoms selected from N and S, aryl or a monocyclic heteroaryl; or $R^1$ and $R^2$ together with the carbon to which they are attached form a $C_3$-$C_8$ cycloalkyl or heterocycloalkyl containing 1-4 heteroatoms selected from Oxygen Nitrogen and Sulfur;

$R^4$ is $L^4$, wherein: $L^4$ is

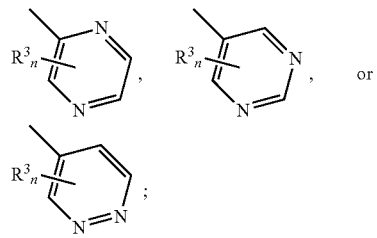

wherein n is 1 or 2;

wherein $R^3$ is H, halogen, —$OR^{11}$, —$NR^{11}R^{12}$, —$SR^{11}$, —$S(O)R^{11}$, —$S(O)_2R^{12}$, —$S(O)_2NR^{11}R^{12}$, $C_1$-$C_8$ haloalkyl, $C_1$-$C_8$ alkyl, $C_1$-$C_8$ alkoxy, cyano, $C_1$-$C_8$ alkylamino, $C_1$-$C_8$ alkoxyamino, aryl, monocyclic heteroaryl containing 1-4 heteroatoms selected from Oxygen Nitrogen and Sulfur or monocyclic heterocycle containing 1-4 heteroatoms selected from Oxygen Nitrogen and Sulfur; and $R^6$ and $R^9$ each are independently selected from H, hydroxy, halogen, cyano, —$SR^{11}$, —$S(O)R^{11}$, —$S(O)_2R^{12}$, —$S(O)_2NR^{11}R^{12}$, $C_1$-$C_8$ haloalkyl, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, aryl, -alkylC(O)—$OR^{12}$, -alkylC(O)$NR^{11}R^{12}$, -alkenylC(O)$OR^{12}$, -alkenylC(O)$NR^{11}R^{12}$, -aryl$(CH_2)_mC(O)OR^{12}$, -aryl$(CH_2)_mC(O)NR^{11}R^{12}$, —$NR^{11}R^{12}$, —$(CH_2)_mC(O)NR^{11}S(O)_2R^{12}$, -aryl$(CH_2)_m$—C(O)NR $^{11}S(O)_2R^{12}$, —$(CH_2)_mS(O)_2NR^{11}C(O)R^{12}$, -aryl$(CH_2)_mS(O)_2NR^{11}C(O)R^{12}$, —XZ, or substituted or unsubstituted monocyclic heterocycle containing 1-4 heteroatoms selected from Oxygen Nitrogen and Sulfur or substituted or unsubstituted monocyclic heteroaryl containing 1-4 heteroatoms selected from Oxygen Nitrogen and Sulfur, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino;

$R^7$ is hydrogen;

$R^8$ is selected from: H, hydroxy, halogen, $CF_3$, cyano, —$SR^{11}$, —$S(O)R^{11}$, —$(CH_2)_mC(O)$—$OR^{12}$, —$(CH_2)_mC(O)NR^{11}R^{12}$—$S(O)_2R^{12}$, —$S(O)_2NR^{11}R^{12}$, —$C(O)OR^{12}$, —$C(O)NR^{11}R^{12}$, —$C(O)R^{12}$, —$NR^{11}C(O)R^{12}$, —$NR^{11}S(O)_2R^{12}$, —$NR^{11}C(O)OR^{12}$, —$C(O)(CH_2)_m$aryl, —$C(=NR^{11})NR^{11}R^{12}$, $NR^{11}C(=NR^{11})NR^{11}R^{12}$, —$C_1$-$C_8$ haloalkyl, —$B(OH)_2$, tetrazole, carboxylic acid biostere, $C_1$-$C_8$ alkyl, $C_3$-$C_8$ cycloalkyl, $C_2$-$C_8$ alkenyl, $C_1$-$C_8$ alkoxy, aryl, -alkylC(O)$OR^{12}$, -alkylC(O)$NR^{11}R^{12}$, -alkenylC(O)$OR^{12}$, -alkenylC(O)$NR^{11}R^{12}$, -aryl$(CH_2)_mC(O)OR^{12}$, -aryl$(CH_2)_mC(O)NR^{11}R^{12}$, —$NR^{11}R^{12}$, —$(CH_2)_mC(O)NR^{11}S(O)_2R^{12}$, -aryl $(CH_2)_m$ $C(O)NR^{11}S(O)_2R^{12}$, —$(CH_2)_mS(O)_2$ $NR^{11}C(O)R^{12}$, -aryl$(CH_2)_mS(O)_2NR^{11}C(O)R^{12}$, —XZ, or alkynyl-phenyl optionally substituted with halogen, or substituted or unsubstituted monocyclic heterocycle or substituted or unsubstituted monocyclic heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino, and X is $C_1$-$C_8$ alkylene, $C_2$-$C_8$ alkenylene, $C_2$-$C_8$ alkynylene, —C(O) or —$S(O)_2$;

Z is H, $CF_3$, —$C_1$-$C_8$ alkyl, $C_3$-$C_8$ cycloalkyl, $C_1$-$C_8$ alkoxy, amino, $C_1$-$C_8$ alkylthio, aryl, or $C_3$-$C_6$ heterocycle or monocyclic heteroaryl, optionally substituted with halogen;

m is 0, 1, 2, 3, or 4;

$R^{10}$ is H, $CF_3$, $C_1$-$C_8$ alkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{11}$, —$NR^{11}R^{12}$, —$SR^{11}$, —$S(O)R^{11}$, —$S(O)_2R^{12}$, or —$S(O)_2NR^{11}R^{12}$;

$R^{11}$, $R^{12}$ and $R^{13}$ are each independently H, $C_1$-$C_8$ alkyl, $C_1$-$C_8$ fluoroalkyl, aryl, benzyl, $C_{2-8}$ alkenyl, $C_{2-8}$ alkynyl, -alkyl-C(O)$OR^{14}$, -alkenyl-C(O)$OR^{14}C(O)R^{14}$, monocylic heteroaryl, or monocylic heterocycle; and $R^{14}$ is H, $C_1$-$C_8$ alkyl, $C_1$-$C_8$ haloalkyl, aryl, or benzyl.

2. A compound according to claim 1, having the structure of Formula (II)

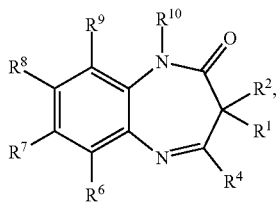

or a pharmaceutically acceptable salt, stereoisomer or tautomer thereof wherein $R^3$ is H, $OR^{11}$, $C_1$-$C_8$ alkylfluoro, $C_1$-$C_8$ alkyl, or $C_1$-$C_8$ alkoxy; $R^1$, $R^2$ and $R^{10}$ are H; $R^3$ is H; m is 0, 1, 2, or 3; wherein $R^6$ and $R^9$ are H; $R^{12}$ is H or $C_1$-$C_6$ alkyl; and $R^8$ is halogen, $CF_3$, cyano, thiophene, imidazole, tetrazole, —$(CH_2)_m$—C(O)—$OR^{12}$, —$(CH_2)_m$—C(O)—$NR^{11}R^{12}$, aryl-$(CH_2)_m$—C(O)—$OR^{12}$, aryl-$(CH_2)_m$—C(O)—$NR^{11}R^{12}$, —$NR^{11}R^{12}$, or phenyl optionally substituted with halogen.

3. A compound according to claim 2, wherein $L^4$ is

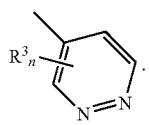

4. A compound according to claim 2, wherein $R^1$, $R^2$, $R^6$, $R^9$ and $R^{10}$ are each hydrogen.

5. A compound according to claim 2, wherein $R^1$, $R^2$ and $R^{10}$ are H; $R^{12}$ is H or $C_1$-$C_6$ alkyl; $R^3$ is H, halogen, $OR^{11}$, $C_1$-$C_8$ alkylfluoro, $C_1$-$C_8$ alkyl, $C_1$-$C_8$ alkoxy, cyano, aryl, monocyclic heteroaryl or monocyclic heterocycle; and m is 0, 1, 2, or 3.

6. The compound of claim 5, wherein $R^6$ and $R^9$ are H; $R^3$ is H, Cl, cyano, aryl, or monocyclic heteroaryl; and $R^8$ is -alkyl-C(O)OH, -alkenylC(O)OH, aryl-$(CH_2)_m$—C(O)OH, -alkyl-C(O)—$NR^{11}R^{12}$, aryl-$(CH_2)_m$—C(O)—$NR^{11}R^{12}$, $B(OH)_2$, tetrazole, or $S(O)_2R^{12}$.

7. A pharmaceutical formulation comprising a compound of claim 1 and a pharmaceutically-acceptable excipient.

8. The pharmaceutical formulation of claim 7, further comprising a CNS agent.

9. The pharmaceutical formulation of claim 7, further comprising an anti-depressant agent.

* * * * *